US007355003B2

(12) United States Patent
Narva et al.

(10) Patent No.: US 7,355,003 B2
(45) Date of Patent: *Apr. 8, 2008

(54) PESTICIDAL PROTEINS

(75) Inventors: Kenneth E. Narva, San Diego, CA (US); H. Ernest Schnepf, San Diego, CA (US); Mark Knuth, Poway, CA (US); Michael R. Pollard, Okemos, MI (US); Guy A. Cardineau, Poway, CA (US); George E. Schwab, Encinitas, CA (US); Tracy Ellis Michaels, Escondido, CA (US)

(73) Assignee: Mycogen Corporation, Indianapolis, IN (US)

( * ) Notice: Subject to any disclaimer, the term of this patent is extended or adjusted under 35 U.S.C. 154(b) by 375 days.

This patent is subject to a terminal disclaimer.

(21) Appl. No.: 11/037,780

(22) Filed: Jan. 18, 2005

(65) Prior Publication Data

US 2005/0155112 A1 Jul. 14, 2005

Related U.S. Application Data

(60) Division of application No. 10/099,278, filed on Mar. 15, 2002, now Pat. No. 6,900,371, which is a continuation of application No. 09/378,088, filed on Aug. 20, 1999, now Pat. No. 6,372,480, which is a continuation-in-part of application No. 08/844,188, filed on Apr. 18, 1997, now Pat. No. 6,127,180, which is a continuation-in-part of application No. 08/633,993, filed on Apr. 19, 1996, now Pat. No. 6,083,499.

(51) Int. Cl.

| | |
|---|---|
| ***C07K 14/325*** | (2006.01) |
| ***A01N 63/02*** | (2006.01) |
| *C12N 15/32* | (2006.01) |

(52) U.S. Cl. ..................... 530/350; 514/12; 536/23.71

(58) Field of Classification Search ..................... None
See application file for complete search history.

(56) References Cited

U.S. PATENT DOCUMENTS

| | | | |
|---|---|---|---|
| 4,849,217 | A | 7/1989 | Soares et al. |
| 5,151,363 | A | 9/1992 | Payne |
| 5,204,100 | A | 4/1993 | Carozzi et al. |
| 5,723,758 | A | 3/1998 | Payne et al. |

FOREIGN PATENT DOCUMENTS

| | | |
|---|---|---|
| EP | 0 359 472 | 3/1990 |
| EP | 0 454 485 | 10/1991 |
| EP | 0 462 721 B1 | 8/2001 |
| WO | WO 94/16079 | 7/1994 |
| WO | WO 95/02694 | 1/1995 |
| WO | WO 97/40162 | 10/1997 |
| WO | WO 00/24904 | 5/2000 |
| WO | WO 00/66742 | 11/2000 |

OTHER PUBLICATIONS

Hofte et al., "Insecticidal Crystal Proteins of *Bacillus thuringiensis*," Microbiological Reviews (1989), pp. 242-255, vol. 53.

*Primary Examiner*—Rebecca Prouty
(74) *Attorney, Agent, or Firm*—Saliwanchik, Lloyd & Saliwanchik

(57) ABSTRACT

The subject invention concerns new classes of pesticidally active proteins and the polynucleotide sequences which encode these proteins. More specifically, in preferred embodiments, pesticidal proteins of approximately 40-50 kDa and of approximately 10-15 kDa are used for controlling corn rootworms. Also described are novel pesticidal isolates of *Bacillus thuringiensis*.

6 Claims, 2 Drawing Sheets

```
            1                                                            50
{149b145k}  ..........  .....GLYAA  TYLSLDDSGV  SLMNKNDDDI  DDYNLKWFLF
{167h245k}  ..........  .......HAA  TYLSLDDSGV  SLMNKNDDDI  DDYNLRWFLF
{80jj145k}  MLDTNKVYEI  SNLANGLYTS  TYLSLDDSGV  SLMSKKDEDI  DDYNLKWELF
Consensus   ----------  ----------  TYLSLDDSGV  SLM-K-D-DI  DDYNL-WELF

            51                                                          100
{149b145k}  PIDDDQYIIT  SYAANNCKVW  NVNNDKINVS  TYSSTNSIQK  WQIKANGSSY
{167h245k}  PIDDNQYIIT  SYAANNCKVW  NVNNDKINVS  TYSSTNSIQK  WQIKANASSY
{80jj145k}  PIDNNQYIIT  SYGANNCKVW  NVKNDKINVS  TYSSTNSVQK  WQIKAKDSSY
Consensus   PID--QYIIT  SY-ANNCKVW  NV-NDKINVS  TYSSTNS-QK  WQIKA--SSY

            101                                                         150
{149b145k}  VIQSDNGKVL  TAGTGQALGL  IRLTDESSNN  PNQQWNLTSV  QTIQLPQKPI
{167h245k}  VIQSNNGKVL  TAGTGQSLGL  IRLTDESPDN  PNQQWNLTPV  QTIQLPPKPT
{80jj145k}  IIQSDNGKVL  TAGVGQSLGI  VRLTDEFPEN  SNQQWNLTPV  QTIQLPQKPK
Consensus   -IQS-NGKVL  TAG-GQ-LG-  -RLTDE---N  -NQQWNLT-V  QTIQLP-KP-

            151                                                         200
{149b145k}  IDTKLKDYPK  YSPTGNIDNG  TSPQLMGWTL  VPCIMVNDPN  IDKNTQIKTT
{167h245k}  IDTKLKDYPK  YSQTGNIDKG  TPPQLMGWTL  IPCIMVNDPN  IDKNTQIKTT
{80jj145k}  IDEKLKDHPE  YSETGNINPK  TTPQLMGWTL  VPCIMVNDSK  IDKNTQIKTT
Consensus   ID-KLKD-P-  YS-TGNI---  T-PQLMGWTL  -PCIMVND--  IDKNTQIKTT

            201                                                         250
{149b145k}  PYYILKKYQY  WQRAVGSNVA  LRPHEKKSYT  YEWGTEIDQK  TTIINTLGFQ
{167h245k}  PYYILKKYQY  WQQAVGSNVA  LRPHEKKSYA  YEWGTEIDQK  TTIINTLGFQ
{80jj145k}  PYYIFKKYKY  WNLAKGSNVS  LLPHQKRSYD  YEWGTEKNQK  TTIINTVGLQ
Consensus   PYYI-KKY-Y  W--A-GSNV-  L-PH-K-SY-  YEWGTE--QK  TTIINT-G-Q

            251                                                         300
{149b145k}  INIDSGMKFD  IPEVGGGTDE  IKTQLNEELK  IEYSHETKIM  EKY.......
{167h245k}  INIDSGMKFD  IPEVGGGTDE  IKTQLNEELK  IEYSRETKIM  EKY.......
{80jj145k}  INIDSGMKFE  VPEVGGGTED  IKTQLTEELK  VEYSTETKIM  TKYQEHSEID
Consensus   INIDSGMKF-  -PEVGGGT--  IKTQL-EELK  -EYS-ETKIM  -KY-------

            301                                                         350
{149b145k}  ..........  ..........  ..........  ..........  ..........
{167h245k}  ..........  ..........  ..........  ..........  ..........
{80jj145k}  NPTNQPMNSI  GLLIYTSLEL  YRYNGTEIKI  MDIETSDHDT  YTLTSYPNHK
Consensus   ----------  ----------  ----------  ----------  ----------

            351                                 386
{149b145k}  ..........  ..........  ..........  ......
{167h245k}  ..........  ..........  ..........  ......
{80jj145k}  EALLLLTNHS  YEEVEEITKI  PKHTLIKLKK  HYFKK.
Consensus   ----------  ----------  ----------  ------
```

FIG. 1

PESTICIDAL PROTEINS

CROSS-REFERENCE TO A RELATED APPLICATION

This application is a divisional of application Ser. No. 10/099,278, filed Mar. 15, 2002, now U.S. Pat. No. 6,900,371, which is a continuation of application Ser. No. 09/378,088, filed Aug. 20, 1999, now U.S. Pat. No. 6,372,480, which is a continuation-in-part of application Ser. No. 08/844,188, filed Apr. 18, 1997, now U.S. Pat. No. 6,127,180; which is a continuation-in-part of Ser. No. 08/633,993, filed Apr. 19, 1996, now U.S. Pat. No. 6,083,499.

INCORPORATION BY REFERENCE

The Sequence Listing for this application is on duplicate compact discs labeled "Copy 1" and "Copy 2." Copy 1 and Copy 2 each contain only one file named "MA-703C2D2.ST25.txt" which was created on Dec. 29, 2004, and is 154 KB. The entire contents of each of the compact discs are incorporated herein by reference in their entireties.

BACKGROUND OF THE INVENTION

Coleopterans are a significant group of agricultural pests which cause extensive damage to crops each year. Examples of coleopteran pests include corn rootworm and alfalfa weevils.

The alfalfa weevil, *Hypera postica*, and the closely related Egyptian alfalfa weevil, *Hypera brunneipennis*, are the most important insect pests of alfalfa grown in the United States, with 2.9 million acres infested in 1984. An annual sum of 20 million dollars is spent to control these pests. The Egyptian alfalfa weevil is the predominant species in the southwestern U.S., where it undergoes aestivation (i.e., hibernation) during the hot summer months. In all other respects, it is identical to the alfalfa weevil, which predominates throughout the rest of the U.S.

The larval stage is the most damaging in the weevil life cycle. By feeding at the alfalfa plant's growing tips, the larvae cause skeletonization of leaves, stunting, reduced plant growth, and, ultimately, reductions in yield. Severe infestations can ruin an entire cutting of hay. The adults, also foliar feeders, cause additional, but less significant, damage.

Approximately 10 million acres of U.S. corn are infested with corn rootworm species complex each year. The corn rootworm species complex includes the northern corn rootworm, *Diabrotica barberi*, the southern corn rootworm, *D. undecimpunctata howardi*, and the western corn rootworm, *D. virgifera virgifera*. The soil-dwelling larvae of these *Diabrotica* species feed on the root of the corn plant, causing lodging. Lodging eventually reduces corn yield and often results in death of the plant. By feeding on cornsilks, the adult beetles reduce pollination and, therefore, detrimentally affect the yield of corn per plant. In addition, adults and larvae of the genus *Diabrotica* attack cucurbit crops (cucumbers, melons, squash, etc.) and many vegetable and field crops in commercial production as well as those being grown in home gardens.

Control of corn rootworm has been partially addressed by cultivation methods, such as crop rotation and the application of high nitrogen levels to stimulate the growth of an adventitious root system. However, chemical insecticides are relied upon most heavily to guarantee the desired level of control. Insecticides are either banded onto or incorporated into the soil. Problems associated with the use of chemical insecticides are environmental contamination and the development of resistance among the treated insect populations.

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and are specific in their toxic activity. Certain *B.t.* toxin genes have been isolated and sequenced, and recombinant DNA-based *B.t.* products have been produced and approved for use. In addition, with the use of genetic engineering techniques, new approaches for delivering these *B.t.* endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] *TIBTECH* 6:S4-S7). Thus, isolated B.t. endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, investigators have discovered *B.t.* pesticides with specificities for a much broader range of pests. For example, other species of B.t., namely *israelensis* and *tenebrionis* (a.k.a. *B.t.* M-7, a.k.a. *B.t. san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245-255). See also Couch, T. L. (1980) "Mosquito Pathogenicity of *Bacillus thuringiensis* var. *israelensis," Developments in Industrial Microbiology* 22:61-76; Beegle, C. C., (1978) "Use of Entomogenous Bacteria in Agroecosystems," *Developments in Industrial Microbiology* 20:97-104. Krieg, A., A. M. Huger, G. A. Langenbruch, W. Schnetter (1983) *Z. ang. Ent.* 96:500-508, describe *Bacillus thuringiensis* var. *tenebrionis*, which is reportedly active against two beetles in the order Coleoptera. These are the Colorado potato beetle, *Leptinotarsa decemlineata*, and *Agelastica alni*.

Recently, new subspecies of *B.t.* have been identified, and genes responsible for active δ-endotoxin proteins have been isolated (Höfte, H., H. R. Whiteley [1989] *Microbiological Reviews* 52(2):242-255). Höfte and Whiteley classified *B.t.* crystal protein genes into 4 major classes. The classes were CryI (Lepidoptera-specific), CryII (*Lepidoptera*- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271-275).

The 1989 nomenclature and classification scheme of Höfte and Whiteley for crystal proteins was based on both the deduced amino acid sequence and the host range of the toxin. That system was adapted to cover 14 different types of toxin genes which were divided into five major classes. As more toxin genes were discovered, that system started to become unworkable, as genes with similar sequences were found to have significantly different is a partial DNA sequence from insecticidal specificities. A revised nomenclature scheme has been proposed which is based solely on amino acid identity (Crickmore et al. [1996] Society for Invertebrate Pathology, 29th Annual Meeting, 3rd International Colloquium on *Bacillus thuringiensis*, University of Cordoba, Cordoba, Spain, September 1-6, abstract). The mnemonic "cry" has been retained for all of the toxin genes except cytA and cytB, which remain a separate class. Roman numerals have been exchanged for Arabic numerals in the primary rank, and the parentheses in the tertiary rank have been removed. Many of the original names have been retained, with the noted exceptions, although a number have been reclassified. See also "Revisions of the Nomenclature for the *Bacillus thuringiensis* Pesticidal Crystal Proteins," N. Crickmore, D. R. Zeigler, J. Feitelson, E. Schnepf, J. Van Rie, D. Lereclus, J. Baum, and D. H. Dean, *Microbiology and Molecular Biology Reviews* (1998) Vol. 62:807-813; and Crickmore, Zeigler, Feitelson, Schnepf, Van Rie, Lereclus, Baum, and Dean, "*Bacillus thuringiensis* toxin nomenclature" (1999) (website at biols.susx.ac.uk/Home/Neil_Crickmore/Bt/index.html). That system uses the freely available software applications CLUSTAL W and PHYLIP. The NEIGHBOR application within the PHYLIP package uses an arithmetic averages (UPGMA) algorithm.

The cloning and expression of a *B.t.* crystal protein gene in *Escherichia coli* has been described in the published literature (Schnepf, H. E., H. R. Whiteley [1981] *Proc. Natl. Acad. Sci. USA* 78:2893-2897). U.S. Pat. No. 4,448,885 and U.S. Pat. No. 4,467,036 both disclose the expression of *B.t.* crystal protein in *E. coli*.

U.S. Pat. Nos. 4,797,276 and 4,853,331 disclose *B. thuringiensis* strain *tenebrionis* (a.k.a. M-7, a.k.a. *B.t. san diego*) which can be used to control coleopteran pests in various environments. U.S. Pat. No. 4,918,006 discloses *B.t.* toxins having activity against Dipterans. U.S. Pat. No. 4,849,217 discloses *B.t.* isolates which have activity against the alfalfa weevil. U.S. Pat. No. 5,208,077 discloses coleopteran-active *Bacillus thuringiensis* isolates. U.S. Pat. No. 5,632,987 discloses a 130 kDa toxin from PS80JJ1 as having activity against corn rootworm. WO 94/40162, which is related to the subject application, describes new classes of proteins that are toxic to corn rootworm. U.S. Pat. No. 5,151,363 and U.S. Pat. No. 4,948,734 disclose certain isolates of B.t. which have activity against nematodes.

As a result of extensive research and investment of resources, other patents have issued for new *B.t.* isolates, toxins, and genes, and to new uses thereof for controlling different pests. However, the discovery of new *B.t.* isolates, toxins, and genes remains an empirical, unpredictable art.

BRIEF SUMMARY OF THE INVENTION

The subject invention concerns novel materials and methods for controlling non-mammalian pests. In a preferred embodiment, the subject invention provides materials and methods for the control of coleopteran pests. In specific embodiments, the materials and methods described herein are used to control corn rootworm and/or alfalfa weevil.

The subject invention advantageously provides two new classes of polynucleotide sequences which encode corresponding novel classes of pesticidal proteins. One novel class of polynucleotide sequences as described herein encodes proteins which have a full-length molecular weight of approximately 40-50 kDa. In a specific embodiment, these proteins have a molecular weight of about 43-47 kDa. A second class of polynucleotides, which encodes pesticidal proteins of about 10-15 kDa, is also provided according to the subject invention. In a specific embodiment, these proteins have a molecular weight of about 13-14 kDa.

In preferred embodiments, a 40-50 kDa protein and a 10-15 kDa protein are used together, with the proteins being pesticidal in combination. Thus, the two classes of proteins of the subject invention can be referred to as "binary toxins." As used herein, the term "toxin" includes either class of these pesticidal proteins.

The subject invention includes polynucleotides which encode either of the 40-50 kDa or the 10-15 kDa toxins, polynucleotides which encode portions or fragments of the full length toxins that retain pesticidal activity when used in combination, and polynucleotide sequences which encode both types of toxins. In a preferred embodiment, these toxins are active against coleopteran pests, more preferably corn rootworm, and most preferably Western corn rootworm.

In some embodiments, *B.t.* toxins useful according to the invention include toxins which can be obtained from the *B.t.* isolates designated as PS80JJ1, PS149B1, and PS167H2. Of these, PS149B1 and PS167H2 are novel isolates. The subject invention also includes the use of variants of the exemplified *B.t.* isolates and toxins which have substantially the same coleopteran-active properties as the specifically exemplified *B.t.* isolates and toxins. Such variant isolates would include, for example, mutants. Procedures for making mutants are well known in the microbiological art. Ultraviolet light and chemical mutagens such as nitrosoguanidine are used extensively toward this end.

In one embodiment of the subject invention, the polynucleotide sequences of the subject invention are used to encode toxins of approximately 43-47 kDa. The genes which encode the 43-47 kDa toxins can be obtained from, for example, PS80JJ1, PS149B1, or PS167H2. In a second embodiment, the polynucleotides of the subject invention are used to encode toxins of approximately 13-14 kDa. The approximately 13-14 kDa toxin, as well as the genes which encode these toxins, can also be obtained from PS80JJ1, PS149B1, or PS167H2. These toxins are then used to control coleopteran pests. In a particularly preferred embodiment, the coleopteran pests are corn rootworms. In a particularly preferred embodiment, a 40-50 kDa protein of the subject invention is used in combination with a 10-15 kDa protein. Thus, the proteins of the subject invention can be used to augment and/or facilitate the activity of other protein toxins.

In a preferred embodiment, the subject invention concerns plants cells transformed with at least one polynucleotide sequence of the subject invention such that the transformed plant cells express pesticidal toxins in tissues consumed by the target pests.

Alternatively, the *B.t.* isolates of the subject invention, or recombinant microbes expressing the toxins described herein, can be used to control pests. In this regard, the invention includes the treatment of substantially intact *B.t.* cells, and/or recombinant cells containing the expressed toxins of the invention, treated to prolong the pesticidal activity when the substantially intact cells are applied to the environment of a target pest. The treated cell acts as a protective coating for the pesticidal toxin.

The toxins of the subject invention are oral intoxicants that affect an insect's midgut cells upon ingestion by the target insect. Thus, by consuming recombinant host cells, for example, that express the toxins, the target insect contacts the proteins of the subject invention, which are toxic to the pest. This results in control of the target pest.

BRIEF DESCRIPTION OF THE DRAWINGS

FIG. 1 shows three specific 43-47 kDa pesticidal toxins of the subject invention as well as a consensus sequence for these pesticidal toxins.

BRIEF DESCRIPTION OF THE SEQUENCES

Figure 2:
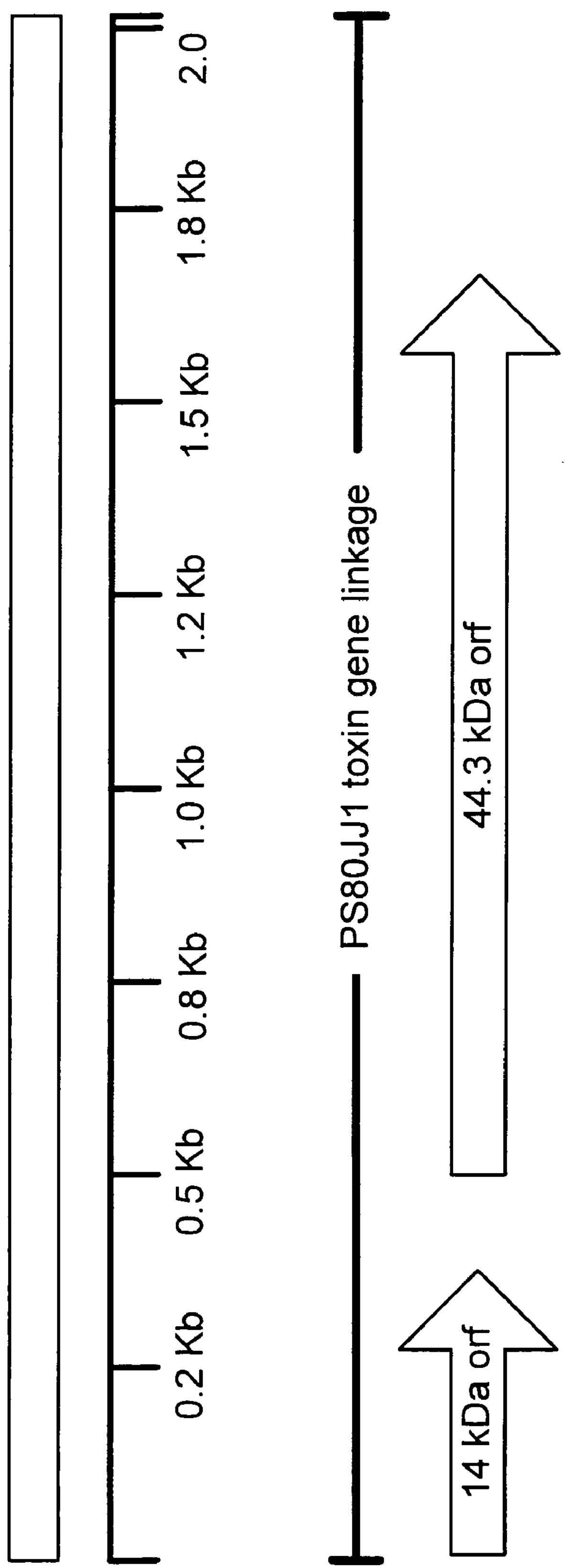
FIG. 2 shows the relationship of the 14 and 45 kDa sequences of PS80JJ1 (SEQ ID NOS. 31 and 10).

SEQ ID NO. 1 is a 5-amino acid N-terminal sequence of the approximately 45 kDa toxin of 80JJ1.

SEQ ID NO. 2 is a 25-amino acid N-terminal sequence of the approximately 45 kDa toxin of 80JJ1.

SEQ ID NO. 3 is a 24-amino acid N-terminal sequence of the approximately 14 kDa toxin of 80JJ1.

SEQ ID NO. 4 is the N-terminal sequence of the approximately 47 kDa toxin from 149B1.

SEQ ID NO. 5 is a 50-amino acid N-terminal amino acid sequence for the purified approximately 14 kDa protein from PS149B1.

SEQ ID NO. 6 is the N-terminal sequence of the approximately 47 kDa toxin from 167H2.

SEQ ID NO. 7 is a 25-amino acid N-terminal sequence for the purified approximately 14 kDa protein from PS167H2.

SEQ ID NO. 8 is an oligonucleotide probe for the gene encoding the PS80JJ1 44.3 kDa toxin and is a forward primer for PS149B1 and PS167H2 used according to the subject invention.

SEQ ID NO. 9 is a reverse primer for PS149B1 and PS167H2 used according to the subject invention.

SEQ ID NO. 10 is the nucleotide sequence of the gene encoding the approximately 45 kDa PS80JJ1 toxin.

SEQ ID NO. 11 is the amino acid sequence for the approximately 45 kDa PS80JJ1 toxin.

SEQ ID NO. 12 is the partial nucleotide sequence of the gene encoding the approximately 44 kDa PS149B1 toxin.

SEQ ID NO. 13 is the partial amino acid sequence for the approximately 44 kDa PS149B1 toxin.

SEQ ID NO. 14 is the partial nucleotide sequence of the gene encoding the approximately 44 kDa PS167H2 toxin.

SEQ ID NO. 15 is the partial amino acid sequence for the approximately 44 kDa PS167H2 toxin.

SEQ ID NO. 16 is a peptide sequence used in primer design according to the subject invention.

SEQ ID NO. 17 is a peptide sequence used in primer design according to the subject invention.

SEQ ID NO. 18 is a peptide sequence used in primer design according to the subject invention.

SEQ ID NO. 19 is a peptide sequence used in primer design according to the subject invention.

SEQ ID NO. 20 is a nucleotide sequence corresponding to the peptide of SEQ ID NO. 16.

SEQ ID NO. 21 is a nucleotide sequence corresponding to the peptide of SEQ ID NO. 17.

SEQ ID NO. 22 is a nucleotide sequence corresponding to the peptide of SEQ ID NO. 18.

SEQ ID NO. 23 is a nucleotide sequence corresponding to the peptide of SEQ ID NO. 19.

SEQ ID NO. 24 is a reverse primer based on the reverse complement of SEQ ID NO. 22.

SEQ ID NO. 25 is a reverse primer based on the reverse complement of SEQ ID NO. 23.

SEQ ID NO. 26 is a forward primer based on the PS80JJ1 44.3 kDa toxin.

SEQ ID NO. 27 is a reverse primer based on the PS80JJ1 44.3 kDa toxin.

SEQ ID NO. 28 is a generic sequence representing a new class of toxins according to the subject invention.

SEQ ID NO. 29 is an oligonucleotide probe used according to the subject invention.

SEQ ID NO. 30 is the nucleotide sequence of the entire genetic locus containing open reading frames of both the 14 and 45 kDa PS80JJ1 toxins and the flanking nucleotide sequences.

SEQ ID NO. 31 is the nucleotide sequence of the PS80JJ1 14 kDa toxin open reading frame.

SEQ ID NO. 32 is the deduced amino acid sequence of the 14 kDa toxin of PS80JJ1.

SEQ ID NO. 33 is a reverse oligonucleotide primer used according to the subject invention.

SEQ ID NO. 34 is the nucleotide sequence of the entire genetic locus containing open reading frames of both the 14 and 44 kDa PS167H2 toxins and the flanking nucleotide sequences.

SEQ ID NO. 35 is the nucleotide sequence of the gene encoding the approximately 14 kDa PS167H2 toxin.

SEQ ID NO. 36 is the amino acid sequence for the approximately 14 kDa PS167H2 toxin.

SEQ ID NO. 37 is the nucleotide sequence of the gene encoding the approximately 44 kDa PS167H2 toxin.

SEQ ID NO. 38 is the amino acid sequence for the approximately 44 kDa PS167H2 toxin.

SEQ ID NO. 39 is the nucleotide sequence of the entire genetic locus containing open reading frames of both the 14 and 44 kDa PS149B1 toxins and the flanking nucleotide sequences.

SEQ ID NO. 40 is the nucleotide sequence of the gene encoding the approximately 14 kDa PS149B1 toxin.

SEQ ID NO. 41 is the amino acid sequence for the approximately 14 kDa PS149B1 toxin.

SEQ ID NO. 42 is the nucleotide sequence of the gene encoding the approximately 44 kDa PS149B1 toxin.

SEQ ID NO. 43 is the amino acid sequence for the approximately 44 kDa PS149B1 toxin.

SEQ ID NO. 44 is a maize-optimized gene sequence encoding the approximately 14 kDa toxin of 80JJ1.

SEQ ID NO. 45 is a maize-optimized gene sequence encoding the approximately 44 kDa toxin of 80JJ1.

SEQ ID NO. 46 is the DNA sequence of a reverse primer used in Example 15, below.

SEQ ID NO. 47 is the DNA sequence of a forward primer used in Example 16, below.

SEQ ID NO. 48 is the DNA sequence of a reverse primer used in Example 16, below.

SEQ ID NO. 49 is the DNA sequence of a forward primer used in Example 16, below.

SEQ ID NO. 50 is the DNA sequence of a reverse primer used in Example 16, below.

SEQ ID NO. 51 is the DNA sequence from PS131 W2 which encodes the 14 kDa protein.

SEQ ID NO. 52 is the amino acid sequence of the 14 kDa protein of PS131W2.

SEQ ID NO. 53 is a partial DNA sequence from PS131W2 for the 44 kDa protein.

SEQ ID NO. 54 is a partial amino acid sequence for the 44 kDa protein of PS131 W2.

SEQ ID NO. 55 is the DNA sequence from PS158T3 which encodes the 14 kDa protein.

SEQ ID NO. 56 is the amino acid sequence of the 14 kDa protein of PS158T3.

SEQ ID NO. 57 is a partial DNA sequence from PS158T3 for the 44 kDa protein.

SEQ ID NO. 58 is a partial amino acid sequence for the 44 kDa protein of PS158T3.

SEQ ID NO. 59 is the DNA sequence from PS158X10 which encodes the 14 kDa protein.

SEQ ID NO. 60 is the amino acid sequence of the 14 kDa protein of PS158X10.

SEQ ID NO. 61 is the DNA sequence from PS185FF which encodes the 14 kDa protein.

SEQ ID NO. 62 is the amino acid sequence of the 14 kDa protein of PS185FF.

SEQ ID NO. 63 is a partial DNA sequence from PS185FF for the 44 kDa protein.

SEQ ID NO. 64 is a partial amino acid sequence for the 44 kDa protein of PS185FF.

SEQ ID NO. 65 is the DNA sequence from PS185GG which encodes the 14 kDa protein.

SEQ ID NO. 66 is the amino acid sequence of the 14 kDa protein of PS185GG.

SEQ ID NO. 67 is the DNA sequence from PS185GG for the 44 kDa protein.

SEQ ID NO. 68 is the amino acid sequence for the 44 kDa protein of PS185GG.

SEQ ID NO. 69 is the DNA sequence from PS185L12 which encodes the 14 kDa protein.

SEQ ID NO. 70 is the amino acid sequence of the 14 kDa protein of PS185L12.

SEQ ID NO. 71 is the DNA sequence from PS185W3 which encodes the 14 kDa protein.

SEQ ID NO. 72 is the amino acid sequence of the 14 kDa protein of PS185W3.

SEQ ID NO. 73 is the DNA sequence from PS186FF which encodes the 14 kDa protein.

SEQ ID NO. 74 is the amino acid sequence of the 14 kDa protein of PS186FF.

SEQ ID NO. 75 is the DNA sequence from PS187F3 which encodes the 14 kDa protein.

SEQ ID NO. 76 is the amino acid sequence of the 14 kDa protein of PS187F3.

SEQ ID NO. 77 is a partial DNA sequence from PS187F3 for the 44 kDa protein.

SEQ ID NO. 78 is a partial amino acid sequence for the 44 kDa protein of PS187F3.

SEQ ID NO. 79 is the DNA sequence from PS187G1 which encodes the 14 kDa protein.

SEQ ID NO. 80 is the amino acid sequence of the 14 kDa protein of PS187G1.

SEQ ID NO. 81 is a partial DNA sequence from PS187G1 for the 44 kDa protein.

SEQ ID NO. 82 is a partial amino acid sequence for the 44 kDa protein of PS187G1.

SEQ ID NO. 83 is the DNA sequence from PS187L14 which encodes the 14 kDa protein.

SEQ ID NO. 84 is the amino acid sequence of the 14 kDa protein of PS187L14.

SEQ ID NO. 85 is a partial DNA sequence from PS187L14 for the 44 kDa protein.

SEQ ID NO. 86 is a partial amino acid sequence for the 44 kDa protein of PS187L14.

SEQ ID NO. 87 is the DNA sequence from PS187Y2 which encodes the 14 kDa protein.

SEQ ID NO. 88 is the amino acid sequence of the 14 kDa protein of PS187Y2.

SEQ ID NO. 89 is a partial DNA sequence from PS187Y2 for the 44 kDa protein.

SEQ ID NO. 90 is a partial amino acid sequence for the 44 kDa protein of PS187Y2.

SEQ ID NO. 91 is the DNA sequence from PS201G which encodes the 14 kDa protein.

SEQ ID NO. 92 is the amino acid sequence of the 14 kDa protein of PS201G.

SEQ ID NO. 93 is the DNA sequence from PS201HH which encodes the 14 kDa protein.

SEQ ID NO. 94 is the amino acid sequence of the 14 kDa protein of PS201HH.

SEQ ID NO. 95 is the DNA sequence from PS201L3 which encodes the 14 kDa protein.

SEQ ID NO. 96 is the amino acid sequence of the 14 kDa protein of PS201L3.

SEQ ID NO. 97 is the DNA sequence from PS204C3 which encodes the 14 kDa protein.

SEQ ID NO. 98 is the amino acid sequence of the 14 kDa protein of PS204C3.

SEQ ID NO. 99 is the DNA sequence from PS204G4 which encodes the 14 kDa protein.

SEQ ID NO. 100 is the amino acid sequence of the 14 kDa protein of PS204G4.

SEQ ID NO. 101 is the DNA sequence from PS204I11 which encodes the 14 kDa protein.

SEQ ID NO. 102 is the amino acid sequence of the 14 kDa protein of PS204I11.

SEQ ID NO. 103 is the DNA sequence from PS204J7 which encodes the 14 kDa protein.

SEQ ID NO. 104 is the amino acid sequence of the 14 kDa protein of PS204J7.

SEQ ID NO. 105 is the DNA sequence from PS236B6 which encodes the 14 kDa protein.

SEQ ID NO. 106 is the amino acid sequence of the 14 kDa protein of PS236B6.

SEQ ID NO. 107 is the DNA sequence from PS242K10 which encodes the 14 kDa protein.

SEQ ID NO. 108 is the amino acid sequence of the 14 kDa protein of PS242K10.

SEQ ID NO. 109 is a partial DNA sequence from PS242K10 for the 44 kDa protein.

SEQ ID NO. 110 is a partial amino acid sequence for the 44 kDa protein of PS242K10.

SEQ ID NO. 111 is the DNA sequence from PS246P42 which encodes the 14 kDa protein.

SEQ ID NO. 112 is the amino acid sequence of the 14 kDa protein of PS246P42.

SEQ ID NO. 113 is the DNA sequence from PS69Q which encodes the 14 kDa protein.

SEQ ID NO. 114 is the amino acid sequence of the 14 kDa protein of PS69Q.

SEQ ID NO. 115 is the DNA sequence from PS69Q for the 44 kDa protein.

SEQ ID NO. 116 is the amino acid sequence for the 44 kDa protein of PS69Q.

SEQ ID NO. 117 is the DNA sequence from KB54 which encodes the 14 kDa protein.

SEQ ID NO. 118 is the amino acid sequence of the 14 kDa protein of KB54.

SEQ ID NO. 119 is the DNA sequence from KR1209 which encodes the 14 kDa protein.

SEQ ID NO. 120 is the amino acid sequence of the 14 kDa protein of KR1209.

SEQ ID NO. 121 is the DNA sequence from KR1369 which encodes the 14 kDa protein.

SEQ ID NO. 122 is the amino acid sequence of the 14 kDa protein of KR1369.

SEQ ID NO. 123 is the DNA sequence from KR589 which encodes the 14 kDa protein.

SEQ ID NO. 124 is the amino acid sequence of the 14 kDa protein of KR589.

SEQ ID NO. 125 is a partial DNA sequence from KR589 for the 44 kDa protein.

SEQ ID NO. 126 is a partial amino acid sequence for the 44 kDa protein of KR589.

SEQ ID NO. 127 is a polynucleotide sequence for a gene designated 149B1-15-PO, which is optimized for expression in *Zea mays*. This gene encodes an approximately 15 kDa toxin obtainable from PS149B1 that is disclosed in WO 97/40162.

SEQ ID NO. 128 is a polynucleotide sequence for a gene designated 149B1-45-PO, which is optimized for expression in *Zea mays*. This gene encodes an approximately 45 kDa toxin obtainable from PS149B1 that is disclosed in WO 97/40162.

SEQ ID NO. 129 is a polynucleotide sequence for a gene designated 80JJ1-15-PO7, which is optimized for expression in maize. This is an alternative gene that encodes an approximately 15 kDa toxin.

SEQ ID NO. 130 is an amino acid sequence for a toxin encoded by the gene designated 80JJ1-15-PO7.

DETAILED DISCLOSURE OF THE INVENTION

The subject invention concerns two new classes of polynucleotide sequences which encode novel pesticidal proteins. In one embodiment, the proteins have a full-length molecular weight of approximately 40-50 kDa. In specific embodiments exemplified herein, these proteins have a molecular weight of about 43-47 kDa. In a second embodiment, the pesticidal proteins have a molecular weight of approximately 10-15 kDa. In specific embodiments exemplified herein, these proteins have a molecular weight of about 13-14 kDa.

In preferred embodiments, a 40-50 kDa protein and a 10-15 kDa protein are used together, and the proteins are pesticidal in combination. Thus, the two classes of proteins of the subject invention can be referred to as "binary toxins." As used herein, the term "toxin" includes either class of pesticidal proteins. The subject invention concerns polynucleotides which encode either the 40-50 kDa or the 10-15 kDa toxins, polynucleotides which encode portions or fragments of the full length toxins that retain pesticidal activity when used in combination, and polynucleotide sequences which encode both types of toxins. In a preferred embodiment, these toxins are active against coleopteran pests, more preferably corn rootworm, and most preferably Western corn rootworm.

Certain specific toxins are exemplified herein. For toxins having a known amino acid sequence, the molecular weight is also known. Those skilled in the art will recognize that the apparent molecular weight of a protein as determined by gel electrophoresis will sometimes differ from the true molecular weight. Therefore, reference herein to, for example, a 45 kDa protein or a 14 kDa protein is understood to refer to proteins of approximately that size even if the true molecular weight is somewhat different.

The subject invention concerns not only the polynucleotide sequences which encode these classes of toxins, but also the use of these polynucleotide sequences to produce recombinant hosts which express the toxins. In a further aspect, the subject invention concerns the combined use of an approximately 40-50 kDa toxin of the subject invention together with an approximately 10-15 kDa toxin of the subject invention to achieve highly effective control of pests, including coleopterans such as corn rootworm.

Thus, control of coleopterans, including corn rootworm using the isolates, toxins, and genes of the subject invention can be accomplished by a variety of methods known to those skilled in the art. These methods include, for example, the application of *B.t.* isolates to the pests (or their location), the application of recombinant microbes to the pests (or their locations), and the transformation of plants with genes which encode the pesticidal toxins of the subject invention. Recombinant microbes may be, for example, a B.t., *E. coli*, or *Pseudomonas*. Transformations can be made by those skilled in the art using standard techniques. Materials necessary for these transformations are disclosed herein or are otherwise readily available to the skilled artisan. Control of other pests such as lepidopterans and other insects, nematodes, and mites can also be accomplished by those skilled in the art using standard techniques combined with the teachings provided herein.

The new classes of toxins and polynucleotide sequences provided here are defined according to several parameters. One critical characteristic of the toxins described herein is pesticidal activity. In a specific embodiment, these toxins have activity against coleopteran pests. The toxins and genes of the subject invention can be further defined by their amino acid and nucleotide sequences. The sequences of the molecules within each novel class can be defined herein in terms of homology to certain exemplified sequences as well as in terms of the ability to hybridize with, or be amplified by, certain exemplified probes and primers. The classes of toxins provided herein can also be identified based on their immunoreactivity with certain antibodies and based upon their adherence to a generic formula.

It should be apparent to a person skilled in this art that genes encoding pesticidal proteins according to the subject invention can be identified and obtained through several means. The specific genes exemplified herein may be obtained from the isolates deposited at a culture depository as described above. These genes, and toxins, of the subject invention can also be constructed synthetically, for example, by the use of a gene synthesizer.

The sequence of three approximately 45 kDa toxins of the subject invention are provided as SEQ ID NOS. 11, 43, and 38. In a preferred embodiment of the subject invention, the toxins in this new class have a sequence which conforms to the generic sequence presented as SEQ ID NO. 28. In a specific embodiment, the toxins of this class will conform to the consensus sequence shown in FIG. 1.

With the teachings provided herein, one skilled in the art could readily produce and use the various toxins and polynucleotide sequences of the novel classes described herein.

Microorganisms useful according to the subject invention have been deposited in the permanent collection of the Agricultural Research Service Patent Culture Collection (NRRL), Northern Regional Research Center, 1815 North University Street, Peoria, Ill. 61604, USA. The culture repository numbers of the deposited strains are as follows:

| Culture | Repository No. | Deposit Date |
|---|---|---|
| *B.t.* strain PS80JJ1 | NRRL B-18679 | Jul. 17, 1990 |
| *B.t.* strain PS149B1 | NRRL B-21553 | Mar. 28, 1996 |
| *B.t.* strain PS167H2 | NRRL B-21554 | Mar. 28, 1996 |
| *E. coli* NM522(pMYC2365) | NRRL B-21170 | Jan. 5, 1994 |
| *E. coli* NM522(pMYC2382) | NRRL B-21329 | Sep. 28, 1994 |
| *E. coli* NM522(pMYC2379) | NRRL B-21155 | Nov. 3, 1993 |
| *E. coli* NM522(pMYC2421) | NRRL B-21555 | Mar. 28, 1996 |

-continued

| Culture | Repository No. | Deposit Date |
|---|---|---|
| *E. coli* NM522(pMYC2427) | NRRL B-21672 | Mar. 26, 1997 |
| *E. coli* NM522(pMYC2429) | NRRL B-21673 | Mar. 26, 1997 |
| *E. coli* NM522(pMYC2426) | NRRL B-21671 | Mar. 26, 1997 |
| *B.t.* strain PS185GG | NRRL B-30181 | Aug. 19, 1999 |
| *B.t.* strain PS187G1 | NRRL B-30185 | Aug. 19, 1999 |
| *B.t.* strain PS187Y2 | NRRL B-30187 | Aug. 19, 1999 |
| *B.t.* strain PS201G | NRRL B-30188 | Aug. 19, 1999 |
| *B.t.* strain PS201HH2 | NRRL B-30190 | Aug. 19, 1999 |
| *B.t.* strain PS242K10 | NRRL B-30195 | Aug. 19, 1999 |
| *B.t.* strain PS69Q | NRRL B-30175 | Aug. 19, 1999 |
| *B.t.* strain KB54A1-6 | NRRL B-30197 | Aug. 19, 1999 |
| *B.t.* strain KR589 | NRRL B-30198 | Aug. 19, 1999 |
| *B.t.* strain PS185L12 | NRRL B-30179 | Aug. 19, 1999 |
| *B.t.* strain PS185W3 | NRRL B-30180 | Aug. 19, 1999 |
| *B.t.* strain PS187L14 | NRRL B-30186 | Aug. 19, 1999 |
| *B.t.* strain PS186FF | NRRL B-30183 | Aug. 19, 1999 |
| *B.t.* strain PS131W2 | NRRL B-30176 | Aug. 19, 1999 |
| *B.t.* strain PS158T3 | NRRL B-30177 | Aug. 19, 1999 |
| *B.t.* strain PS158X10 | NRRL B-30178 | Aug. 19, 1999 |
| *B.t.* strain PS185FF | NRRL B-30182 | Aug. 19, 1999 |
| *B.t.* strain PS187F3 | NRRL B-30184 | Aug. 19, 1999 |
| *B.t.* strain PS201L3 | NRRL B-30189 | Aug. 19, 1999 |
| *B.t.* strain PS204C3 | NRRL B-21008 | Oct. 6, 1992 |
| *B.t.* strain PS204G4 | NRRL B-18685 | Jul. 17, 1990 |
| *B.t.* strain PS204I11 | NRRL B-30192 | Aug. 19, 1999 |
| *B.t.* strain PS204J7 | NRRL B-30193 | Aug. 19, 1999 |
| *B.t.* strain PS236B6 | NRRL B-30194 | Aug. 19, 1999 |
| *B.t.* strain PS246P42 | NRRL B-30196 | Aug. 19, 1999 |
| *B.t.* strain KR1209 | NRRL B-30199 | Aug. 19, 1999 |
| *B.t.* strain KR1369 | NRRL B-30200 | Aug. 19, 1999 |

The PS80JJ1 isolate is available to the public by virtue of the issuance of U.S. Pat. No. 5,151,363.

A further aspect of the subject invention concerns novel isolates and the toxins and genes obtainable from these isolates. Examples of novel *B.t.* isolates of the subject invention include PS149B1 and PS167H2. Other novel isolates have been deposited and are included in the above list. These isolates have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing the cultures. The depositor acknowledges the duty to replace the deposit(s) should the depository be unable to furnish a sample when requested, due to the condition of the deposit(s). All restrictions on the availability to the public of the subject culture deposits will be irrevocably removed upon the granting of a patent disclosing them.

Following is a table which provides characteristics of certain *B.t.* isolates useful according to the subject invention.

TABLE 1

Description of *B.t.* strains toxic to *coleopterans*

| Culture | Crystal Description | Approx. MW (kDa) | Sero-type | NRRL Deposit | Deposit Date |
|---|---|---|---|---|---|
| PS80JJ1 | multiple attached | 130, 90, 47, 37, 14 | 4a4b, sotto | B-18679 | Jul. 17, 1990 |
| PS149B1 | | 130, 47, 14 | | B-21553 | Mar. 28, 1996 |
| PS167H2 | | 70, 47, 14 | | B-23554 | Mar. 28, 1996 |

Other isolates of the subject invention can also be characterized in terms of the shape and location of toxin inclusions.

Toxins and genes of the subject invention can be identified and obtained by using oligonucleotide probes, for example, these probes are detectable nucleotide sequences. The probes (and the polynucleotides of the subject invention) may be DNA, RNA, or PNA (peptide nucleic acid). These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) *DNA Probes*, Stockton Press, New York, N.Y., pp. 169-170. For example, as stated therein, high stringency washes can be conducted with 2×SSC (Standard Saline Citrate)/0.1% SDS (Sodium Dodecyl Sulfate) for 15 minutes at room temperature. Two washes are typically performed. The 2×SSC/0.1% SDS can be prepared by adding 50 ml of 20×SSC and 5 ml of 10% SDS to 445 ml of water. 20×SSC can be prepared by combining NaCl (175.3 g/0.150 M), sodium citrate (88.2 g/0.015 M), and water to 1 liter, followed by adjusting pH to 7.0 with 10 N NaOH. 10% SDS can be prepared by dissolving 10 g of SDS in 50 ml of autoclaved water, diluting to 100 ml, and aliquotting. Alternatively, high stringency washes can be conducted with 0.1×SSC/0.1% SDS for 30 minutes each at 55° C.

Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

In a preferred embodiment, the toxins of the subject invention have at least one of the following characteristics:

(a) said toxin is encoded by a nucleotide sequence which hybridizes under stringent conditions with a nucleotide sequence selected from the group consisting of: DNA which encodes SEQ ID NO. 2, DNA which encodes SEQ ID NO. 4, DNA which encodes SEQ ID NO. 6, SEQ ID NO. 8, SEQ ID NO. 10, DNA which encodes SEQ ID NO. 11, SEQ ID NO. 12, DNA which encodes SEQ ID NO. 13, SEQ ID NO. 14, DNA which encodes SEQ ID NO. 15, DNA which encodes SEQ ID NO. 16, DNA which encodes SEQ ID NO. 17, DNA which encodes SEQ ID NO. 18, DNA which encodes SEQ ID NO. 19, SEQ ID NO. 20, SEQ ID NO. 21, SEQ ID NO.

22, SEQ ID NO. 23, SEQ ID NO. 24, SEQ ID NO. 25, SEQ ID NO. 26, SEQ ID NO. 27, DNA which encodes a pesticidal portion of SEQ ID NO. 28, SEQ ID NO. 37, DNA which encodes SEQ ID NO. 38, SEQ ID NO. 42, and DNA which encodes SEQ ID NO. 43;

(b) said toxin immunoreacts with an antibody to an approximately 40-50 kDa pesticidal toxin, or a fragment thereof, from a *Bacillus thuringiensis* isolate selected from the group consisting of PS80JJ1 having the identifying characteristics of NRRL B-18679, PS149B1 having the identifying characteristics of NRRL B-21553, and PS167H2 having the identifying characteristics of NRRL B-21554;

(c) said toxin is encoded by a nucleotide sequence wherein a portion of said nucleotide sequence can be amplified by PCR using a primer pair selected from the group consisting of SEQ ID NOS. 20 and 24 to produce a fragment of about 495 bp, SEQ ID NOS. 20 and 25 to produce a fragment of about 594 bp, SEQ ID NOS. 21 and 24 to produce a fragment of about 471 bp, and SEQ ID NOS. 21 and 25 to produce a fragment of about 580 bp;

(d) said toxin comprises a pesticidal portion of the amino acid sequence shown in SEQ ID NO. 28;

(e) said toxin comprises an amino acid sequence which has at least about 60% homology with a pesticidal portion of an amino acid sequence selected from the group consisting of SEQ ID NO. 11, SEQ ID NO. 13, SEQ ID NO. 15, SEQ ID NO. 38, and SEQ ID NO. 43;

(f) said toxin is encoded by a nucleotide sequence which hybridizes under stringent conditions with a nucleotide sequence selected from the group consisting of DNA which encodes SEQ ID NO. 3, DNA which encodes SEQ ID NO. 5, DNA which encodes SEQ ID NO. 7, DNA which encodes SEQ ID NO. 32, DNA which encodes SEQ ID NO. 36, and DNA which encodes SEQ ID NO. 41;

(g) said toxin immunoreacts with an antibody to an approximately 10-15 kDa pesticidal toxin, or a fragment thereof, from a *Bacillus thuringiensis* isolate selected from the group consisting of PS80JJ1 having the identifying characteristics of NRRL B-18679, PS149B1 having the identifying characteristics of NRRL B-21553, and PS167H2 having the identifying characteristics of NRRL B-21554;

(h) said toxin is encoded by a nucleotide sequence wherein a portion of said nucleotide sequence can be amplified by PCR using the primer pair of SEQ ID NO. 29 and SEQ ID NO. 33; and (i) said toxin comprises an amino acid sequence which has at least about 60% homology with an amino acid sequence selected from the group consisting of SEQ ID NO. 3, SEQ ID NO. 5, SEQ ID NO. 7, pesticidal portions of SEQ ID NO. 32, pesticidal portions of SEQ ID NO. 36, and pesticidal portions of SEQ ID NO. 41.

Hybridization with other polynucleotides of the subject invention, such as the DNA sequences included in SEQ ID NOS. 46-126, are also defining characteristics of genes of the subject invention.

As used herein "stringent" conditions for hybridization refers to conditions which achieve the same, or about the same, degree of specificity of hybridization as the conditions employed by the current applicants. Specifically, hybridization of immobilized DNA on Southern blots with $^{32}P$-labeled gene-specific probes was performed by standard methods (Maniatis, T., E. F. Fritsch, J. Sambrook [1982] *Molecular Cloning: A Laboratory Manual*, Cold Spring Harbor Laboratory, Cold Spring Harbor, N.Y.). In general, hybridization and subsequent washes were carried out under stringent conditions that allowed for detection of target sequences with homology to the PS80JJ1 toxin genes. For double-stranded DNA gene probes, hybridization was carried out overnight at 20-25° C. below the melting temperature (Tm) of the DNA hybrid in 6×SSPE, 5× Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266-285).

$$Tm=81.5° C.+16.6 Log[Na+]+0.41 (\% G+C)-0.61(\% formamide)-600/length of duplex in base pairs.$$

Washes are typically carried out as follows:

(1) Twice at room temperature for 15 minutes in 1×SSPE, 0.1% SDS (low stringency wash).

Once at Tm-20° C. for 15 minutes in 0.2×SSPE, 0.1% SDS (moderate stringency wash).

For oligonucleotide probes, hybridization was carried out overnight at 10-20° C. below the melting temperature (Tm) of the hybrid in 6×SSPE, 5× Denhardt's solution, 0.1% SDS, 0.1 mg/ml denatured DNA. Tm for oligonucleotide probes was determined by the following formula:

$$Tm(° C.)=2(\text{number } T/A \text{ base pairs})+4(\text{number } G/C \text{ base pairs})$$

(Suggs, S. V., T. Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683-693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

Modification of genes and toxins. The genes and toxins useful according to the subject invention include not only the specifically exemplified full-length sequences, but also portions (including internal deletions compared to the full-length proteins), fragments (including terminal deletions compared to the full-length protein) of these sequences, variants, mutants, chimeric, and fusion proteins, including proteins having substituted amino acids, which retain the characteristic pesticidal activity of the proteins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

Variations of genes may be readily constructed using standard techniques for making point mutations, for example. Also, U.S. Pat. No. 5,605,793, for example, describes methods for generating additional molecular diversity by using DNA reassembly after random fragmentation. Fragments of full-length genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from B.t. isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other *B.t.* toxins. These antibodies can then be used to specifically identify equivalent toxins with the characteristic activity by immunoprecipitation, enzyme linked immunosorbent assay (ELISA), or western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. The amino acid identity will typically be greater than 60%, preferably be greater than 75%, more preferably greater than 80%, more preferably greater than 90%, and can be greater than 95%. Preferably, the identity scores are calculated using the methods and algorithms of Crickmore et al. as described in the Background section, above. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

Synthetic genes which are functionally equivalent to the toxins of the subject invention can also be used to transform hosts. Methods for the production of synthetic genes can be found in, for example, U.S. Pat. No. 5,380,831.

Recombinant hosts. The toxin-encoding genes of the subject invention can be introduced into a wide variety of microbial or plant hosts. Expression of the toxin gene results, directly or indirectly, in the intracellular production and maintenance of the pesticide proteins. Thus, the target pest can contact the pesticidal proteins by ingesting plant tissue containing the pesticidal proteins, which are toxic to the pest. The result is control of the pest. Alternatively, suitable microbial hosts, e.g., *Pseudomonas*, can be applied to the situs of the pest, where some of which can proliferate, and are ingested by the target pests. The microbe hosting the toxin gene can be treated under conditions that prolong the activity of the toxin and stabilize the cell. The treated cell, which retains the toxic activity, then can be applied to the environment of the target pest.

In preferred embodiments, recombinant plant cells and plants are used. Preferred plants (and plant cells) are corn and/or maize.

Where the *B.t.* toxin gene is introduced via a suitable vector into a microbial host, and said host is applied to the environment in a living state, certain host microbes should be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca,*

*Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of ways are available for introducing a *B.t.* gene encoding a toxin into the target host under conditions which allow for stable maintenance and expression of the gene. These methods are well known to those skilled in the art and are described, for example, in U.S. Pat. No. 5,135,867, which is incorporated herein by reference.

Treatment of cells. As mentioned above, *B.t.* or recombinant cells expressing a *B.t.* toxin can be treated to prolong the toxin activity and stabilize the cell. The pesticide microcapsule that is formed comprises the *B.t.* toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., *Animal Tissue Techniques*, W.H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bioavailability or bioactivity of the toxin.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells of the invention can be cultured using standard art media and fermentation techniques. Upon completion of the fermentation cycle the bacteria can be harvested by first separating the *B.t.* spores and crystals from the fermentation broth by means well known in the art. The recovered *B.t.* spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and spores and crystals of the *B.t.* isolates, or recombinant microbes comprising the genes obtainable from the *B.t.* isolates disclosed herein, can be applied to the soil. Formulated product can also be applied as a seed-coating or root treatment or total plant treatment at later stages of the crop cycle. Plant and soil treatments of *B.t.* cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include Theological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Mutants. Mutants of the isolates of the invention can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

A smaller percentage of the asporogenous mutants will remain intact and not lyse for extended fermentation periods; these strains are designated lysis minus. Lysis minus strains can be identified by screening asporogenous mutants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is placed in the center of the plate and allowed to dry. Resistant cultures showed no lysis in the area where the phage lysate has been placed after incubation at 30° C. for 24 hours.

Following are examples which illustrate procedures for practicing the invention. These examples should not be construed as limiting. All percentages are by weight and all solvent mixture proportions are by volume unless otherwise noted.

EXAMPLE 1

Culturing of *B.t.* Isolates of the Invention

A subculture of the *B.t.* isolates, or mutants thereof, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| pH 7.2 | |
| Salts Solution (100 ml) | |
| MgSO4•7H2O | 2.46 g |
| $MnSO_4 \cdot H_2O$ | 0.04 g |
| $ZnSO_4 \cdot 7H_2O$ | 0.28 g |
| $FeSO_4 \cdot 7H_2O$ | 0.40 g |
| $CaCl_2$ Solution (100 ml) | |
| $CaCl_2 \cdot 2H_2O$ | 3.66 g |

The salts solution and $CaCl_2$ solution are filter-sterilized and added to the autoclaved and cooked broth at the time of inoculation. Flasks are incubated at 30° C. on a rotary shaker at 200 rpm for 64 hours.

The above procedure can be readily scaled up to large fermentors by procedures well known in the art.

The *B.t.* spores and/or crystals, obtained in the above fermentation, can be isolated by procedures well known in the art. A frequently-used procedure is to subject the harvested fermentation broth to separation techniques, e.g., centrifugation.

EXAMPLE 2

Protein Purification for 45 kDa 80JJ1 Protein

One gram of lyophilized powder of 80JJ1 was suspended in 40 ml of buffer containing 80 mM Tris-Cl pH 7.8, 5 mM EDTA, 100 μM PMSF, 0.5 μg/ml Leupeptin, 0.7. μg/ml Pepstatin, and 40 μg/ml Bestatin. The suspension was centrifuged, and the resulting supernatant was discarded. The pellet was washed five times using 35-40 ml of the above buffer for each wash. The washed pellet was resuspended in 10 ml of 40% NaBr, 5 mM EDTA, 100 μM PMSF, 0.5 μg/ml Leupeptin, 0.7 μg/ml Pepstatin, and 40 μg/ml Bestatin and placed on a rocker platform for 75 minutes. The NaBr suspension was centrifuged, the supernatant was removed, and the pellet was treated a second time with 40% NaBr, 5 mM EDTA, 100 μM PMSF, 0.5 μg/ml Leupeptin, 0.7 μg/ml Pepstatin, and 40 μg/ml Bestatin as above. The supernatants (40% NaBr soluble) were combined and dialyzed against 10 mM CAPS pH 10.0, 1 mM EDTA at 4° C. The dialyzed extracts were centrifuged and the resulting supernatant was removed. The pellet (40% NaBr dialysis pellet) was suspended in 5 ml of $H_2O$ and centrifuged. The resultant supernatant was removed and discarded. The washed pellet was washed a second time in 10 ml of $H_2O$ and centrifuged as above. The washed pellet was suspended in 1.5 ml of $H_2O$ and contained primarily three peptides with molecular weights of approximately 47 kDa, 45 kDa, and 15 kDa when analyzed using SDS-PAGE. At this stage of purification, the suspended 40% NaBr dialysis pellet contained approximately 21 mg/ml of protein by Lowry assay.

The peptides in the pellet suspension were separated using SDS-PAGE (Laemlli, U.K. [1970] *Nature* 227:680) in 15% acrylamide gels. The separated proteins were then electrophoretically blotted to a PVDF membrane (Millipore Corp.) in 10 mM CAPS pH 11.0, 10% MeOH at 100 V constant. After one hour the PVDF membrane was rinsed in water briefly and placed for 3 minutes in 0.25% Coomassie blue R-250, 50% methanol, 5% acetic acid. The stained membrane was destained in 40% MeOH, 5% acetic acid. The destained membrane was air-dried at room temperature (LeGendre et al. [1989] *In A Practical Guide to Protein Purification For Microsequencing*, P. Matsudaira, ed., Academic Press, New York, N.Y.). The membrane was sequenced using automated gas phase Edman degradation (Hunkapillar, M. W., R. M. Hewick, W. L. Dreyer, L. E. Hood [1983] *Meth. Enzymol.* 91:399).

The amino acid analysis revealed that the N-terminal sequence of the 45 kDa band was as follows: Met-Leu-Asp-Thr-Asn (SEQ ID NO. 1).

The 47 kDa band was also analyzed and the N-terminal amino acid sequence was determined to be the same 5-amino acid sequence as SEQ ID NO. 1. Therefore, the N-terminal amino acid sequences of the 47 kDa peptide and the 45 kDa peptide were identical.

This amino acid sequence also corresponds to a sequence obtained from a 45 kDa peptide obtained from PS80JJ1 spore/crystal powders, using another purification protocol, with the N-terminal sequence as follows: Met-Leu-Asp-Thr-Asn-Lys-Val-Tyr-Glu-Ile-Ser-Asn-Leu-Ala-Asn-Gly-Leu-Tyr-Thr-Ser-Thr-Tyr-Leu-Ser-Leu (SEQ ID NO. 2).

EXAMPLE 3

Purification of the 14 kDa Peptide of PS80JJ1

0.8 ml of the white dialysis suspension (approximately 21 mg/ml) containing the 47 kDa, 45 kDa, and 15 kDa peptides, was dissolved in 10 ml of 40% NaBr, and 0.5 ml of 100 mM EDTA were added. After about 18 hours (overnight), a white opaque suspension was obtained. This was collected by centrifugation and discarded. The supernatant was concentrated in a Centricon-30 (Amicon Corporation) to a final volume of approximately 15 ml. The filtered volume was washed with water by filter dialysis and incubated on ice, eventually forming a milky white suspension. The suspension was centrifuged and the pellet and supernatant were separated and retained. The pellet was then suspended in 1.0 ml water (approximately 6 mg/ml). The pellet contained substantially pure 15 kDa protein when analyzed by SDS-PAGE.

The N-terminal amino acid sequence was determined to be: Ser-Ala-Arg-Glu-Val-His-Ile-Glu-I $$le-Asn-Asn-Thr-Arg-His-Thr-Leu-Gln-Leu-Glu-Ala-Lys-Thr-Lys-Leu (SEQ ID NO. 3).

EXAMPLE 4

Protein Purification and Characterization of PS149B1 45 kDa Protein

The P1 pellet was resuspended with two volumes of deionized water per unit wet weight, and to this was added nine volumes of 40% (w/w) aqueous sodium bromide. This and all subsequent operations were carried out on ice or at 4-6° C. After 30 minutes, the suspension was diluted with 36 volumes of chilled water and centrifuged at 25,000×g for 30 minutes to give a pellet and a supernatant.

The resulting pellet was resuspended in 1-2 volumes of water and layered on a 20-40% (w/w) sodium bromide gradient and centrifuged at 8,000×g for 100 minutes. The layer banding at approximately 32% (w/w) sodium bromide (the "inclusions," or INC) was recovered and dialyzed overnight against water using a dialysis membrane with a 6-8 kDa MW cut-off. Particulate material was recovered by centrifugation at 25,000×g, resuspended in water, and aliquoted and assayed for protein by the method of Lowry and by SDS-PAGE.

The resulting supernatant was concentrated 3- to 4-fold using Centricon-10 concentrators, then dialyzed overnight against water using a dialysis membrane with a 6-8 kDa MW cut-off. Particulate material was recovered by centrifugation at 25,000×g, resuspended in water, and aliquoted and assayed for protein by the method of Lowry and by SDS-PAGE. This fraction was denoted as P1.P2.

The peptides in the pellet suspension were separated using SDS-PAGE (Laemlli, U.K., supra) in 15% acrylamide gels. The separated proteins were then electrophoretically blotted to a PVDF membrane (Millipore Corp.) in 10 mM CAPS pH 11.0, 10% MeOH at 100 V constant. After one hour the PVDF membrane was rinsed in water briefly and placed for 3 minutes in 0.25% Coomassie blue R-250, 50% methanol, 5% acetic acid. The stained membrane was destained in 40% MeOH, 5% acetic acid. The destained membrane was air-dried at room temperature (LeGendre et al., supra). The membrane was sequenced using automated gas phase Edman degradation (Hunkapillar et al., supra).

Protein analysis indicated the presence of two major polypeptides, with molecular weights of 47 kDa and 14 kDa. Molecular weights were measured against standard polypeptides of known molecular weight. This process provides only an estimate of true molecular weight. The 47 kDa band from PS149B1 migrated on SDS-PAGE in a manner indistinguishable from the 47 kDa protein from PS80JJ1. Likewise, the 14 kDa band from PS149B1 migrated on SDS-PAGE in a manner indistinguishable from 14 kDa bands from PS167H2 and PS80JJ1. Apart from these two polypeptides, which were estimated to account for 25-35% (47 kDa) and 35-55% (15 kDa) of the Coomassie staining material respectively, there may be minor bands, including those of estimated MW at 46 kDa, 130 kDa, and 70 kDa.

Protein analysis indicated that fraction INC contained a single polypeptide with MW of 47 kDa, and that fraction P1.P2 contained a single polypeptide with MW of 14 kDa. These polypeptides were recovered in yields greater than 50% from P1.

The N-terminal amino acid sequence for the purified 47 kDa protein from PS149B1 is: Met-Leu-Asp-Thr-Asn-Lys-Val-Tyr-Glu-Ile-Ser-Asn-His-Ala-Asn-Gly-Leu-Tyr-Ala-Ala-Thr-Tyr-Leu-Ser-Leu (SEQ ID NO. 4).

The N-terminal amino acid sequence for the purified 14 kDa protein from PS149B1 is: Ser-Ala-Arg-Glu-Val-His-Ile-Asp-Val-Asn-Asn-Lys-Thr-Gly-His-Thr-Leu-Gln-Leu-Glu-Asp-Lys-Thr-Lys -Leu-Asp-Gly-Gly-Arg-Trp-Arg-Thr-Ser-Pro-Xaa-Asn-Val-Ala-Asn-Asp-Gln-Ile-Lys-Thr-Phe-Val-Ala-Glu-Ser-Asn (SEQ ID NO. 5).

EXAMPLE 5

Amino Acid Sequence for 45 kDa and 14 kDa Toxins of PS167H2

The N-terminal amino acid sequence for the purified 45 kDa protein from PS167H2 is: Met-Leu-Asp-Thr-Asn-Lys-Ile-Tyr-Glu-Ile-Ser-Asn-Tyr-Ala-Asn-Gly-Leu-His-Ala-Ala-Thr-Tyr-Leu-Ser-Leu (SEQ ID NO. 6).

The N-terminal amino acid sequence for the purified 14 kDa protein from PS167H2 is: Ser-Ala-Arg-Glu-Val-His-Ile-Asp-Val-Asn-Asn-Lys-Thr-Gly-His-Thr-Leu-Gln-Leu-Glu-Asp-Lys-Thr-Lys-Leu (SEQ ID NO. 7).

These amino acid sequences can be compared to the sequence obtained for the 47 kDa peptide obtained from 80JJ1 spore/crystal powders with the N-terminal sequence (SEQ ID NO. 1) and to the sequence obtained for the 14 kDa peptide obtained from 80JJ1 spore/crystal powders with the N-terminal sequence (SEQ ID NO. 3).

Clearly, the 45-47 kDa proteins are highly related and probably represent one gene family, and the 14 kDa proteins are highly related and probably represent another gene family.

EXAMPLE 6

Molecular Cloning, Expression, and DNA Sequence Analysis of a Novel δ-Endotoxin Gene from *Bacillus thuringiensis* Strain PS80JJ1

Total cellular DNA was prepared from *Bacillus thuringiensis* (*B.t.*) cells grown to an optical density, at 600 nm, of 1.0. Cells were pelleted by centrifugation and resuspended in protoplast buffer (20 mg/ml lysozyme in 0.3 M sucrose, 25 mM Tris-Cl [pH 8.0], 25 mM EDTA). After incubation at 37° C. for 1 hour, protoplasts were lysed by two cycles of freezing and thawing. Nine volumes of a solution of 0.1 M NaCl, 0.1% SDS, 0.1 M Tris-Cl were added to complete lysis. The cleared lysate was extracted twice with phenol: chloroform (1:1). Nucleic acids were precipitated with two volumes of ethanol and pelleted by centrifugation. The pellet was resuspended in TE buffer and RNase was added to a final concentration of 50 μg/ml. After incubation at 37° C. for 1 hour, the solution was extracted once each with phenol:chloroform (1:1) and TE-saturated chloroform. DNA was precipitated from the aqueous phase by the addition of one-tenth volume of 3 M NaOAc and two volumes of ethanol. DNA was pelleted by centrifugation, washed with 70% ethanol, dried, and resuspended in TE buffer.

An oligonucleotide probe for the gene encoding the PS80JJ1 45 kDa toxin was designed from N-terminal peptide sequence data. The sequence of the 29-base oligonucleotide probe was:

5'-ATG YTW GAT ACW AAT AAA GTW TAT GAA AT-3' (SEQ ID NO. 8)

This oligonucleotide was mixed at four positions as shown. This probe was radiolabeled with $^{32}P$ and used in standard condition hybridization of Southern blots of PS80JJ1 total cellular DNA digested with various restriction endonucleases. Representative autoradiographic data from these experiments showing the sizes of DNA restriction fragments containing sequence homology to the 44.3 kDa toxin oligonucleotide probe of SEQ ID NO. 8 are presented in Table 3.

TABLE 3

RFLP of PS80JJ1 cellular DNA fragments on Southern blots that hybridized under standard conditions with the 44.3 kDa toxin gene oligonucleotide probe (SEQ ID NO. 8)

| Restriction Enzyme | Approximate Fragment Size (kbp) |
|---|---|
| EcoRI | 6.0 |
| HindIII | 8.3 |
| KpnI | 7.4 |
| PstI | 11.5 |
| XbaI | 9.1 |

These DNA fragments identified in these analyses contain all or a segment of the PS80JJ1 45 kDa toxin gene. The approximate sizes of the hybridizing DNA fragments in Table 3 are in reasonable agreement with the sizes of a subset of the PS80JJ1 fragments hybridizing with a PS80JJ1 45 kDa toxin subgene probe used in separate experiments, as predicted (see Table 4, below).

A gene library was constructed from PS80JJ1 DNA partially digested with Sau3AI. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The Sau3AI inserts were ligated into BamHI-digested LambdaGem-11 (Promega, Madison, Wis.). Recombinant phage were packaged and plated on *E. coli* KW251 cells. Plaques were screened by hybridization with the oligonucleotide probe described above. Hybridizing phage were plaque-purified and used to infect liquid cultures of *E. coli* KW251 cells for isolation of DNA by standard procedures (Maniatis et al., supra).

Southern blot analysis revealed that one of the recombinant phage isolates contained an approximately 4.8 kbp XbaI-SacI band that hybridized to the PS80JJ1 toxin gene probe. The SacI site flanking the PS80JJ1 toxin gene is a phage vector cloning site, while the flanking XbaI site is located within the PS80JJ1 DNA insert. This DNA restriction fragment was subcloned by standard methods into pBluescript S/K (Stratagene, San Diego, Calif.) for sequence analysis. The resultant plasmid was designated pMYC2421. The DNA insert was also subcloned into pHTBlueII (an *E. coli/B. thuringiensis* shuttle vector comprised of pBluescript S/K [Stratagene, La Jolla, Calif.] and the replication origin from a resident *B.t.* plasmid [D. Lereclus et al. (1989) *FEMS Microbiology Letters* 60:211-218]) to yield pMYC2420.

An oligonucleotide probe for the gene encoding the PS80JJ1 14 kDa toxin was designed from N-terminal peptide sequence data. The sequence of the 28-base oligonucleotide probe was: 5' GW GAA GTW CAT ATW GAA ATW AAT AAT AC 3' (SEQ ID NO. 29). This oligonucleotide was mixed at four positions as shown. The probe was radiolabeled with $^{32}P$ and used in standard condition hybridizations of Southern blots of PS80JJ1 total cellular and pMYC2421 DNA digested with various restriction endonucleases. These RFLP mapping experiments demonstrated that the gene encoding the 14 kDa toxin is located on the same genomic EcoRI fragment that contains the N-terminal coding sequence for the 44.3 kDa toxin.

To test expression of the PS80JJ1 toxin genes in B.t., pMYC2420 was transformed into the acrystalliferous (Cry-) *B.t.* host, CryB (A. Aronson, Purdue University, West Lafayette, Ind.), by electroporation. Expression of both the approximately 14 and 44.3 kDa PS80JJ1 toxins encoded by pMYC2420 was demonstrated by SDS-PAGE analysis. Toxin crystal preparations from the recombinant CryB [pMYC2420] strain, MR536, were assayed and found to be active against western corn rootworm.

The PS80JJ1 toxin genes encoded by pMYC2421 were sequenced using the ABI373 automated sequencing system and associated software. The sequence of the entire genetic locus containing both open reading frames and flanking nucleotide sequences is shown in SEQ ID NO. 30. The termination codon of the 14 kDa toxin gene is 121 base pairs upstream (5') from the initiation codon of the 44.3 kDa toxin gene (FIG. 2). The PS80JJ1 14 kDa toxin open reading frame nucleotide sequence (SEQ ID NO. 31), the 44.3 kDa toxin open reading frame nucleotide sequence (SEQ ID NO. 10), and the respective deduced amino acid sequences (SEQ ID NO. 32 and SEQ ID NO. 11) are novel compared to other toxin genes encoding pesticidal proteins.

Thus, the nucleotide sequence encoding the 14 kDa toxin of PS80JJ1 is shown in SEQ ID NO. 31. The deduced amino acid sequence of the 14 kDa toxin of PS80JJ1 is shown in SEQ ID NO. 32. The nucleotide sequences encoding both the 14 and 45 kDa toxins of PS80JJ1, as well as the flanking sequences, are shown in SEQ ID NO. 30. The relationship of these sequences is shown in FIG. 2.

A subculture of *E. coli* NM522 containing plasmid pMYC2421 was deposited in the permanent collection of the Patent Culture Collection (NRRL), Regional Research Center, 1815 North University Street, Peoria, Ill. 61604 USA on Mar. 28, 1996. The accession number is NRRL B-21555.

EXAMPLE 7

RFLP and PCR Analysis of Additional Novel δ-Endotoxin Genes from *Bacillus thuringiensis* Strains PS149B1 and PS167H2

Two additional strains active against corn rootworm, PS149B1 and PS167H2, also produce parasporal protein crystals comprised in part of polypeptides approximately 14 and 45 kDa in size. Southern hybridization and partial DNA sequence analysis were used to examine the relatedness of these toxins to the 80JJ1 toxins. DNA was extracted from these *B.t.* strains as described above, and standard Southern hybridizations were performed using the 14 kDa toxin oligonucleotide probe (SEQ ID NO. 29) and an approximately 800 bp PCR fragment of the 80JJ1 44.3 kDa toxin gene-encoding sequence. Representative RFLP data from these experiments showing the sizes of DNA restriction fragments containing sequence homology to the 44.3 kDa toxin are presented in Table 4. Representative RFLP data from these experiments showing the sizes of DNA restriction fragments containing sequence homology to the approximately 14 kDa toxin are presented in Table 5.

TABLE 4

RFLP of PS80JJ1, PS149B1, and PS167H2 cellular DNA fragments on Southern blots that hybridized with the approximately 800 bp PS80JJ1 44.3 kDa toxin subgene probe under standard conditions

| | Strain | | |
|---|---|---|---|
| | PS80JJ1 | PS149B1 | PS167H2 |
| Restriction enzyme | Approximate fragment size (kbp) | | |
| EcoRI | 6.4 | 5.7 | 2.6 |
| | 1.3 | 2.8 | |
| | 0.6 | | |
| HindIII | 8.2 | 6.2 | 4.4 |
| KpnI | 7.8 | 10.0 | 11.5 |
| PstI | 12.0 | 9.2 | 9.2 |
| | | | 8.2 |
| XbaI | 9.4 | 10.9 | 10.9 |
| SacI | 17.5 | 15.5 | 11.1 |
| | 13.1 | 10.5 | 6.3 |

Each of the three strains exhibited unique RFLP patterns. The hybridizing DNA fragments from PS149B1 or PS167H2 contain all or part of toxin genes with sequence homology to the PS80JJ1 44.3 kDa toxin.

TABLE 5

Restriction fragment length polymorphisms of PS80JJ1, PS149B1, and PS167H2 cellular DNA fragments on Southern blots that hybridized with the PS80JJ1 14 kDa toxin oligonucleotide probe under standard conditions

| | Strain | | |
|---|---|---|---|
| | PS80JJ1 | PS149B1 | PS167H2 |
| Restriction enzyme | Approximate fragment size (kbp) | | |
| EcoRI | 5.6 | 2.7 | 2.7 |
| HindIII | 7.1 | 6.0 | 4.7 |
| XbaI | 8.4 | 11.2 | 11.2 |

Each of the three strains exhibited unique RFLP patterns. The hybridizing DNA fragments from PS149B1 or PS167H2 contain all or part of toxin genes with sequence homology to the PS80JJ1 14 kDa toxin gene.

Portions of the toxin genes in PS149B1 or PS167H2 were amplified by PCR using forward and reverse oligonucleotide primer pairs designed based on the PS80JJ1 44.3 kDa toxin gene sequence. For PS149B1, the following primer pair was used:

```
Forward:
                                          (SEQ ID NO. 8)
5'-ATG YTW GAT ACW AAT AAA GTW TAT GAA AT-3'

Reverse:
                                          (SEQ ID NO. 9)
5'-GGA TTA TCT ATC TCT GAG TGT TCT TG-3'
```

For PS167H2, the same primer pair was used. These PCR-derived fragments were sequenced using the ABI373 automated sequencing system and associated software. The partial gene and peptide sequences obtained are shown in SEQ ID NO. 12-15. These sequences contain portions of the nucleotide coding sequences and peptide sequences for novel corn rootworm-active toxins present in *B.t.* strains PS149B1 or PS167H2.

EXAMPLE 8

Molecular Cloning and DNA Sequence Analysis of Novel δ-Endotoxin Genes from *Bacillus thuringiensis* Strains PS149B1 and PS167H2

Total cellular DNA was extracted from strains PS149B1 and PS167H2 as described for PS80JJ1. Gene libraries of size-fractionated Sau3A partial restriction fragments were constructed in Lambda-Gem11 for each respective strain as previously described. Recombinant phage were packaged and plated on *E. coli* KW251 cells. Plaques were screened by hybridization with the oligonucleotide probe specific for the 44 kDa toxin gene. Hybridizing phage were plaque-purified and used to infect liquid cultures of *E. coli* KW251 cells for isolation of DNA by standard procedures (Maniatis et al., supra).

For PS167H2, Southern blot analysis revealed that one of the recombinant phage isolates contained an approximately 4.0 to 4.4 kbp HindIII band that hybridized to the PS80JJ1 44 kDa toxin gene 5' oligonucleotide probe (SEQ ID NO. 8). This DNA restriction fragment was subcloned by standard methods into pBluescript S/K (Stratagene, San Diego, Calif.) for sequence analysis. The fragment was also subcloned into the high copy number shuttle vector, pHT370 (Arantes, O., D. Lereclus [1991*] Gene* 108:115-119) for expression analyses in *Bacillus thuringiensis* (see below). The resultant recombinant, high copy number bifunctional plasmid was designated pMYC2427.

The PS167H2 toxin genes encoded by pMYC2427 were sequenced using the ABI automated sequencing system and associated software. The sequence of the entire genetic locus containing both open reading frames and flanking nucleotide sequences is shown in SEQ ID NO. 34. The termination codon of the 14 kDa toxin gene is 107 base pairs upstream (5') from the initiation codon of the 44 kDa toxin gene. The PS167H2 14 kDa toxin coding sequence (SEQ ID NO. 35), the 44 kDa toxin coding sequence (SEQ ID NO. 37), and the respective deduced amino acid sequences, SEQ ID NO. 36 and SEQ ID NO. 38, are novel compared to other known toxin genes encoding pesticidal proteins. The toxin genes are arranged in a similar manner to, and have some homology with, the PS80JJ1 14 and 44 kDa toxins.

A subculture of *E. coli* NM522 containing plasmid pMYC2427 was deposited in the permanent collection of the Patent Culture Collection (NRRL), Regional Research Center, 1815 North University Street, Peoria, Ill. 61604 USA on 26 Mar. 1997. The accession number is NRRL B-21672.

For PS149B1, Southern blot analysis using the PS80JJ1 44 kDa oligonucleotide 5' probe (SEQ ID NO. 8) demonstrated hybridization of an approximately 5.9 kbp ClaI DNA fragment. Complete ClaI digests of PS149B1 genomic DNA were size fractionated on agarose gels and cloned into pHTBlueII. The fragment was also subcloned into the high copy number shuttle vector, pHT370 (Arantes, O., D. Lereclus [1991] *Gene* 108:115-119) for expression analyses in *Bacillus thuringiensis* (see below). The resultant recombinant, high copy number bifunctional plasmid was designated pMYC2429.

The PS149B1 toxin genes encoded by pMYC2429 were sequenced using the ABI automated sequencing system and associated software. The sequence of the entire genetic locus containing both open reading frames and flanking nucleotide sequences is shown in SEQ ID NO. 39. The termination codon of the 14 kDa toxin gene is 108 base pairs upstream (5') from the initiation codon of the 44 kDa toxin gene. The PS149B1 14 kDa toxin coding sequence (SEQ ID NO. 40), the 44 kDa toxin coding sequence (SEQ ID NO. 42), and the respective deduced amino acid sequences, SEQ ID NO. 41 and SEQ ID NO. 43, are novel compared to other known toxin genes encoding pesticidal proteins. The toxin genes are arranged in a similar manner as, and have some homology with, the PS80JJ1 and PS167H2 14 and 44 kDa toxins. Together, these three toxin operons comprise a new family of pesticidal toxins.

A subculture of *E. coli* NM522 containing plasmid pMYC2429 was deposited in the permanent collection of the Patent Culture Collection (NRRL), Regional Research Center, 1815 North University Street, Peoria, Ill. 61604 USA on 26 Mar. 1997. The accession number is NRRL B-21673.

EXAMPLE 9

PCR Amplification for Identification and Cloning Novel Corn Rootworm-Active Toxin The DNA and peptide sequences of the three novel approximately 45 kDa corn rootworm-active toxins from PS80JJ1, PS149B1, and PS167H2 (SEQ ID NOS. 12-15) were aligned with the Genetics Computer Group sequence analysis program Pileup using a gap weight of 3.00 and a gap length weight of 0.10. The sequence alignments were used to identify conserved peptide sequences to which oligonucleotide primers were designed that were likely to hybridize to genes encoding members of this novel toxin family. Such primers can be used in PCR to amplify diagnostic DNA fragments for these and related toxin genes. Numerous primer designs to various sequences are possible, four of which are described here to provide an example. These peptide sequences are:

```
Asp-Ile-Asp-Asp-Tyr-Asn-Leu         (SEQ ID NO. 16)

Trp-Phe-Leu-Phe-Pro-Ile-Asp         (SEQ ID NO. 17)

Gln-Ile-Lys-Thr-Thr-Pro-Tyr-Tyr     (SEQ ID NO. 18)

Tyr-Glu-Trp-Gly-Thr-Glu.            (SEQ ID NO. 19)
```

The corresponding nucleotide sequences are:

```
5'-GATATWGATGAYTAYAAYTTR-3'       (SEQ ID NO. 20)

5'-TGGTTTTTRTTTCCWATWGAY-3'       (SEQ ID NO. 21)

5'-CAAATHAAAACWACWCCATATTAT-3'    (SEQ ID NO. 22)

5'-TAYGARTGGGGHACAGAA-3'.         (SEQ ID NO. 23)
```

Forward primers for polymerase amplification in thermocycle reactions were designed based on the nucleotide sequences of SEQ ID NOS. 20 and 21.

Reverse primers were designed based on the reverse complement of SEQ ID NOS. 22 and 23:

```
5'-ATAATATGGWGTWGTTTTDATTTG-3'    (SEQ ID NO. 24)

5'-TTCTGTDCCCCAYTCRTA-3'.         (SEQ ID NO. 25)
```

These primers can be used in combination to amplify DNA fragments of the following sizes (Table 6) that identify genes encoding novel corn rootworm toxins.

TABLE 6

Predicted sizes of diagnostic DNA fragments (base pairs) amplifiable with primers specific for novel corn rootworm-active toxins

| Primer pair (SEQ ID NO.) | DNA fragment size (bp) |
|---|---|
| 20 + 24 | 495 |
| 20 + 25 | 594 |
| 21 + 24 | 471 |
| 21 + 25 | 580 |

Similarly, entire genes encoding novel corn rootworm-active toxins can be isolated by polymerase amplification in thermocycle reactions using primers designed based on DNA sequences flanking the open reading frames. For the PS80JJ1 44.3 kDa toxin, one such primer pair was designed, synthesized, and used to amplify a diagnostic 1613 bp DNA fragment that included the entire toxin coding sequence. These primers are:

```
Forward:
5'-CTCAAAGCGGATCAGGAG-3'          (SEQ ID NO. 26)

Reverse:
5'-GCGTATTCGGATATGCTTGG-3'.       (SEQ ID NO. 27)
```

For PCR amplification of the PS80JJ1 14 kDa toxin, the oligonucleotide coding for the N-terminal peptide sequence (SEQ ID NO. 29) can be used in combination with various reverse oligonucleotide primers based on the sequences in the PS80JJ1 toxin gene locus. One such reverse primer has the following sequence:

```
5' CATGAGATTTATCTCCTGATCCGC 3'.   (SEQ ID NO. 33)
```

When used in standard PCR reactions, this primer pair amplified a diagnostic 1390 bp DNA fragment that includes the entire 14 kDa toxin coding sequence and some 3 flanking sequences corresponding to the 121 base intergenic spacer and a portion of the 44.3 kDa toxin gene. When used in combination with the 14 kDa forward primer, PCR will generate a diagnostic 322 base pair DNA fragment.

EXAMPLE 10

Bioassay of Protein

A preparation of the insoluble fraction from the dialyzed NaBr extract of 80JJ1 containing the 47 kDa, 45 kDa, and 15 kDa peptides was bioassayed against Western corn rootworm and found to exhibit significant toxin activity.

EXAMPLE 11

Bioassay of Protein

The purified protein fractions from PS149B1 were bioassayed against western corn rootworm and found to exhibit significant toxin activity when combined. In fact, the combination restored activity to that noted in the original preparation (P1). The following bioassay data set presents percent mortality and demonstrates this effect.

TABLE 7

| Concentration (μg/cm$^2$) | P1 | INC | P1.P2 | INC + P1.P2 |
|---|---|---|---|---|
| 300 | 88, 100, 94 | 19 | 13 | 100 |
| 100 | 94, 50, 63 | 31 | 38 | 94 |
| 33.3 | 19, 19, 44 | 38 | 13 | 50 |
| 11.1 | 13, 56, 25 | 12 | 31 | 13 |
| 3.7 | 0, 50, 0 | 0 | 31 | 13 |
| 1.2 | 13, 43, 12 | 0 | 12 | 19 |
| 0.4 | 6, 12, 6 | 25 | 19 | 6 |

EXAMPLE 12

Clone Dose-Response Bioassays

The PS80JJ1 toxin operon was also subcloned from pMYC2421 into pHT370 for direct comparison of bioactivity with the recombinant toxins cloned from PS149B1 and PS167H2. The resultant recombinant, high copy number bifunctional plasmid was designated pMYC2426.

A subculture of *E. coli* NM522 containing plasmid pMYC2426 was deposited in the permanent collection of the Patent Culture Collection (NRRL), Regional Research Center, 1815 North University Street, Peoria, Ill. 61604 USA on 26 Mar. 1997. The accession number is NRRL B-21671.

To test expression of the PS80JJ1, PS149B1 and PS167H2 toxin genes in B.t., pMYC2426, pMYC2427 and pMYC2429 were separately transformed into the acrystalliferous (Cry-) *B.t.* host, CryB (A. Aronson, Purdue University, West Lafayette, Ind.), by electroporation. The recombinant strains were designated MR543 (CryB [pMYC2426]), MR544 (CryB [pMYC2427]) and MR546 (CryB [pMYC2429]), respectively. Expression of both the approximately 14 and 44 kDa toxins was demonstrated by SDS-PAGE analysis for each recombinant strain.

Toxin crystal preparations from the recombinant strains were assayed against western corn rootworm. Their diet was amended with sorbic acid and SIGMA pen-strep-ampho-B. The material was top-loaded at a rate of 50 μl of suspension per cm$^2$ diet surface area. Bioassays were run with neonate Western corn rootworm larvae for 4 days at approximately 25° C. Percentage mortality and top-load $LC_{50}$ estimates for the clones (pellets) are set forth in Table 8.

TABLE 8

| Sample | Percentage mortality at given protein concentration (μg/cm$^2$) 50 | 5 | 0.5 |
|---|---|---|---|
| MR543 pellet | 44 | 19 | 9 |
| MR544 pellet | 72 | 32 | 21 |
| MR546 pellet | 52 | 32 | 21 |
| dH2O | 7 | | |

The amounts of 14 kDa and 44.3 kDa proteins present in the crystal preparations were estimated by densitometry and used to calculate specific activity expressed as LC50. $LC_{50}$ estimates for the clones (pellets) are set forth in Table 9 (WCRW top load bioassay of *B.t.* clones).

TABLE 9

| *B.t.* Clone | *B.t.* Parental Strain | $LC_{50}$ (μg/cm$^2$)* | 95% CL | Slope |
|---|---|---|---|---|
| MR543 | PS80JJ1 | 37 | 17-366* | 0.79 |
| MR544 | PS167H2 | 10 | 6-14 | 1.6 |
| MR546 | PS149B1 | 8 | 4-12 | 1.5 |
| N/A | CryB cell blank | 4% | N/A | N/A |
| N/A | Water blank | 4% | N/A | N/A |

*Percentage mortality at top dose is provided for controls
**90% CL

EXAMPLE 13

Mutational Analysis of the 14 and 44 kDa Polypeptides in the PS80JJ1 Binary Toxin Operon Binary toxin genes of the subject invention are, in their wild-type state, typically arranged in an operon wherein the 14 kDa protein gene is transcribed first, followed by that of the 45 kDa protein gene. These genes are separated by a relatively short, non-coding region. Representative ORFs are shown in SEQ ID NO. 30, SEQ ID NO. 34, and SEQ ID NO. 39.

In order to investigate the contribution of the individual 14 and 44.3 kDa crystal proteins to corn rootworm activity, each gene in the PS80JJ1 operon was mutated in separate experiments to abolish expression of one of the proteins. The intact gene was then expressed in *B.t.* and recombinant proteins were tested for activity against corn rootworm.

First, the 44.3 kDa gene encoded on pMYC2421 was mutated by truncation at the EcoRI site at base position 387 of the open reading frame. This truncation and subsequent ligation with vector sequences resulted in an open reading frame encoding an approximately 24 kDa hypothetical fusion protein. The resulting operon encoding the intact 14 kDa gene and the truncated 45 kDa gene was subcloned into the high copy number shuttle vector, pHT370 (Arantes, O., D. Lereclus [1991] *Gene* 108:115-119) for expression analyses in *Bacillus thuringiensis*. The resulting plasmid, pMYC2424 was transformed into the acrystalliferous (Cry-) *B.t.* host, CryB (A. Aronson, Purdue University, West Lafayette, Ind.), by electroporation. The resulting recombinant strain was designated MR541. Only the 14 kDa PS80JJ1 protein was detectable by SDSPAGE analysis of sporulated cultures of MR541. Preparations of MR541 expressing only the 14 kDa PS80JJ1 protein were not active in top-load bioassays against corn rootworm.

Next, the 14 kDa gene encoded on pMYC2421 was mutated by insertion of an oligonucleotide linker containing termination codons in all possible reading frames at the NruI site at base position 11 of the open reading frame. The sequence of this linker is 5' TGAGTAACTAGATCTATTCAATTA 3'. The linker introduces a BglII site for confirmation of insertion by BglII restriction digestion. Plasmid clones containing the mutagenic linker were identified with BglII and sequenced for verification. The operon insert encoding the 14 kDa nonsense mutations was subcloned into pHT370, resulting in plasmid pMYC2425. This plasmid was transformed into CryB by electroporation to yield the recombinant *B.t.* strain MR542. Only the 44.3 kDa PS80JJ1 protein was expressed in sporulated cultures of MR542 as shown by SDSPAGE analysis.

Preparations of MR542 expressing only the 44.3 kDa PS80JJ1 protein were not active against corn rootworm.

EXAMPLE 14

Single Gene Heterologous Expression Purification and Bioassay of the 14 and 44.3 kDa Polypeptides from PS149B1 in *Pseudomonas fluorescens*

The 14 kDa and 44.3 polypeptide genes from PS149B1 were separately engineered into plasmid vectors by standard DNA cloning methods, and transformed into *Psuedomonas fluorescens*. The recombinant *Pseudomonas fluorescens* strain expressing only the PS149B1 14 kDa gene was designated MR1253. The recombinant *Pseudomonas fluorescens* strain expressing only the PS149B1 44.3 kDa gene was designated MR1256.

MR1253 and MR1256 each individually expressing one of the two binary proteins were grown in 10L fermentation tanks. A portion of each culture was then pelleted by centrifugation, lysed with lysozyme, and treated with DNAse I to obtain semi-pure protein inclusions. These inclusions were then solubilized in 50 mM Sodium Citrate (pH 3.3) by gentle rocking at 4° C. for 1 hour. The 14 kDa protein dissolved readily in this buffer whereas the 44.3 kDa protein was partially soluble. The solubilized fractions were then centrifuged at 15,000×g for 20 minutes; and the supernatants were retained.

The 14 kDa protein was further purified through ion-exchange chromatography. The solubilized 14 kDa protein was bound to a Econo-S column and eluted with a Sodium Chloride 0-1M gradient.

The chromatographically pure MR1253 (14 kDa protein) and the Sodium Citrate (pH3.3) solubilized preparation of MR1256 (45 kDa protein) were then tested for activity on corn rootworm individually or together at a molar ratio of 1 to 10 (45 kDa protein to 14 kDa protein). Bioassay results showed only background mortality for each of the proteins alone but 87% mortality when combined in the above ratio (Table 10).

TABLE 10

| Molar ratio (45 kD to 14 kD) | load volume | ug 45 kD/ well | ug 14 kD/ well | Total ug protein | CRW Mortality |
|---|---|---|---|---|---|
| 0 to 1 | 100 ul | 0 | 260 | 260 | 13 |
| 1 to 0 | 200 ul | 260 | 0 | 260 | 9 |
| 1 to 10 | 100 ul | 65 | 195 | 260 | 87 |
| water | 100 ul | 0 | 0 | 0 | 11 |

EXAMPLE 15

Identification of Additional Novel 14 kDa and 44.3 kDa Toxin Genes by Hybridization of Total *B.t.* Genomic DNA Total genomic DNA from each isolate was prepared suing the Qiagen DNEasy 96 well tissue kit. DNA in 96-well plates was denatured prior to blotting by adding 10 ul of each DNA sample and 10 ul of 4 M NaOH to 80 ul sterile distilled water. Samples were incubated at 70° C. for one hour after which 100 ul of 20×SSC was added to each well. PS149B1 total genomic DNA was included with each set of 94 samples as a positive hybridization control, and cryB-total genomic DNA was included with each set of 94 samples as a negative hybridization control. Each set of 96 samples was applied to Magnacharge nylon membranes using two 48 well slot blot manifolds (Hoefer Scientific), followed by two washes with 10×SSC. Membranes were baked at 80° C. for one hour and kept dry until used. Membranes were prehybridized and hybridized in standard formamide solution (50% formamide, 5×SSPE, 5× Denhardt's solution, 2% SDS, 100 ug/ml single stranded DNA) at 42° C. Membranes were washed under two conditions: 2×SSC/0.1% SDS at 42° C. (low stringency) and 0.2×SSC/0.1% SDS at 65° C. (moderate to high stringency). Membranes were probed with an approximately 1.3 kilobase pair PCR fragment of the PS149B1 44.3 kDa gene amplified from pMYC2429 using forward primer SEQ ID NO. 8 and a reverse primer with the sequence 5' gtagaagcagaacaagaaggtatt 3' (SEQ ID NO. 46). The probe was radioactively labeled using the Prime-it II kit (Stratagene) and 32-P-dCTP, purified on Sephadex columns, denatured at 94° C. and added to fresh hybridization solution. Strains containing genes with homology to the PS149B1 probe were identified by exposing membranes to X-ray film.

The following strains were identified by positive hybridization reactions: PS184M2, PS185GG, PS187G1, PS187Y2, PS201G, PS201HH2, PS242K10, PS69Q, KB54A1-6, KR136, KR589, PS185L12, PS185W3, PS185Z11, PS186L9, PS187L14, PS186FF, PS131W2, PS147U2, PS158T3, PS158×10, PS185FF, PS187F3, PS198H3, PS201H2, PS201L3, PS203G2, PS203J1, PS204C3, PS204G4, PS204I11, PS204J7, PS210B, PS213E8, PS223L2, PS224F2, PS236B6, PS246P42, PS247C16, KR200, KR331, KR625, KR707, KR959, KR1209, KR1369, KB2C-4, KB10H-5, KB456, KB42C17-13, KB45A43-3, KB54A33-1, KB58A10-3, KB59A54-4, KB59A54-5, KB53B7-8, KB53B7-2, KB60F5-7, KB60F5-11, KB59A58-4, KB60F5-15, KB61A18-1, KB65A15-2, KB65A15-3, KB65A15-7, KB65A15-8, KB65A15-12, KB65A14-1, KB3F-3, T25, KB53A71-6, KB65A11-2, KB68B57-1, KB63A5-3, and KB71A118-6.

EXAMPLE 16

DNA Sequencing of Additional Binary Toxin Genes

Degenerate oligonucleotides were designed to amplify all or part of the 14 and 44.3 kDa genes from *B.t.* strains identified by hybridization with the 149B1 PCR product described above. The oligonucleotides were designed to conserved sequence blocks identified by alignment of the 14 kDa or 44.3 kDa genes from PS149B1, PS167H2 and PS80JJ1. Forward primers for both genes were designed to begin at the ATG initiation codon. Reserve primers were designed as close to the 3' end of each respective gene as possible.

The primers designed to amplify the 14 kDa gene are as follows:

```
149DEG1 (forward):
                                        (SEQ ID NO. 47)
5'-ATG TCA GCW CGY GAA GTW CAY ATT G-3'

149DEG2 (reverse):
                                        (SEQ ID NO. 48)
5'-GTY TGA ATH GTA TAH GTH ACA TG-3'
```

These primers amplify a product of approximately 340 base pairs.

The primers designed to amplify the 44.3 kDa gene are as follows:

```
149DEG3 (forward):
                                        (SEQ ID NO. 49)
5'-ATG TTA GAT ACW AAT AAA RTW TAT G-3'

149DEG4 (reverse):
                                        (SEQ ID NO. 50)
5'-GTW ATT TCT TCW ACT TCT TCA TAH GAA G-3'
```

These primers amplify a product of approximately 1,100 base pairs.

The PCR conditions used to amplify gene products are as follows:

95° C., 1 min., one cycle
95° C., 1 min.
50° C., 2 min., this set repeated 35 cycles
72° C., 2 min.
72° C., 10 min., one cycle PCR products were fractionated on 1% agarose gels and purified from the gel matrix using the Qiaexll kit (Qiagen). The resulting purified fragments were ligated into the pCR-TOPO cloning vector using the TOPO TA cloning kit (Invitrogen). After ligation, one half of the ligation reaction was transformed into XL10 Gold ultracompetant cells (Stratagene). Transformants were then screened by PCR with vector primers 1212 and 1233. Clones containing inserts were grown on the LB/carbenicillin medium for preparation of plasmids using the Qiagen plasmid DNA miniprep kit (Qiagen). Cloned PCR-derived fragments were then sequenced using Applied Biosystems automated sequencing systems and associated software. Sequences of additional novel binary toxin genes and polypeptides related to the holotype 14 and 44.3 kDa toxins from PS80JJ1 and PS149B1 are listed as SEQ ID NOS. 51-126. The section above, entitled "A Brief Description of the Sequences," provides a further explanation of these sequences.

EXAMPLE 17

PS149B1 Toxin Transgenes and Plant Transformation

Separate synthetic transgenes optimized for maize codon usage were designed for both the 14 and 44.3 kDa toxin components. The synthetic versions were designed to modify the guanine and cytosine codon bias to a level more typical for plant DNA. Preferred plant-optimized transgenes are described in SEQ ID NOS. 127-128. The promoter region used for expression of both transgenes was the *Zea mays* ubiquitin promoter plus *Z. mays* exon 1 and *Z. mays* intron 1 (Christensen, A. H. et al. (1992) Plant Mol. Biol. 18:675-689). The transcriptional terminator used for both transgenes was the potato proteinase inhibitor II (PinII) terminator (An, G. et al. 1989 Plant Cell 1:115-22).

Phosphinothricin acetyltransferase (PAT) was used as the selectable marker for plant transformation. The phosphinothricin acetyltransferase gene (pat) was isolated from the bacterium *Streptomyces viridochromogenes* (Eckes P. et al., 1989). The PAT protein acetylates phosphinothricin, or its precursor demethylphosphinothricin, conferring tolerance to a chemically synthesized phosphinothricin such as the herbicide glufosinate-ammonium. Acetylation converts phosphinothricin to an inactive form that is no longer toxic to corn plants. Glufosinate ammonium is a broad spectrum, non-systemic, non-selective herbicide. Regenerating corn tissue or individual corn plants tolerant to glufosinate ammonium herbicide can be readily identified through incorporation of PAT into regeneration medium or by spray application of the herbicide to leaves.

The synthetic version of the pat gene was produced in order to modify the guanine and cytosine codon bias to a level more typical for plant DNA. The promoter for the pat gene is the CaMV promoter of the 35S transcript from cauliflower mosaic virus (Pietrzak et al., 1986). The transcriptional terminator is the CaMV 35 S terminator.

For transformation of maize tissue, a linear portion of DNA, containing the both the PS149B1 14 and 44.3 kDa and pat selectable marker coding sequences, and the regulatory components necessary for expression, was excised from a complete plasmid. This linear portion of DNA, termed an insert, was used in the transformation process.

Maize plants containing PS149B1 14 kDa and 44.3 kDa transgenes were obtained by microprojectile bombardment using the Biolistics® PDS-100He particle gun manufactured by Bio-Rad, essentially as described by Klein et al. (1987). Immature embryos isolated from corn ears harvested approximately 15 days after pollination were cultured on callus initiation medium for three to eight days. On the day of transformation, microscopic tungsten particles were coated with purified DNA and accelerated into the cultured embryos, where the insert DNA was incorporated into the cell chromosome. Inserts of PHP12560 were used; no additional DNA (e.g. carrier DNA) was incorporated into the transformation process. Six days after bombardment, bombarded embryos were transferred to callus initiation medium containing glufosinate (Bialaphos) as the selection agent. Healthy, resistant callus tissue was obtained and repeatedly transferred to fresh selection medium for approximately 12 weeks. Plants were regenerated and transferred to the greenhouse. A total of 436 regenerated plants were obtained. Leaf samples were taken from molecular analysis to verify the presence of the transgenes by PCR and to confirm expression of the foreign protein by ELISA. Plants were then subjected to a whole plant bioassay using western corn rootworm. Positive plants were crossed with inbred lines to obtain seed from the initial transformed plants.

EXAMPLE 18

Further Bioassays

Proteins preparations from the strains identified on Example 15 were assayed for activity against western corn rootworm using the basic top load assay methods, as described in Example 12. The results are shown in Table 11.

TABLE 11

| Strain | LC50 (ug/cm2) | 95% Cl |
|---|---|---|
| KB45A43-3 | 9.48 | 6.58-15.27 |
| 213'E'8 | 10.24 | 7.50-19.87 |
| KR707 | 11.17 | 8.27-22.54[#] |
| 185GG | 11.53 | 7.51-16.81 |
| 187Y2 | 13.82 | 11.08-17.67 |
| 149B1 | 14.77 | 4.91-27.34 |
| 149B1 | 26.90 | 20.76-33.20 |
| 69Q | 27.52 | 117.28-114.77[#] |
| 149B1 | 29.12 | 21.22-39.46 |
| 167H2 | 31.38 | 19.35-47.60 |
| KB54A33-1 | 32.62 | 24.76-83.85 |
| 149B1 | 34.08 | 18.94-55.71 |
| 185Z11 | 34.47 | ND |
| KB60F5-7 | 34.67 | 19.15-124.29 |
| 242K10 | 34.73 | 21.08-58.25 |
| 201G | 34.90 | 13.20-355.18[#] |
| 204J7 | 38.57 | 29.83-48.82 |
| KB60F5-15 | 38.62 | 15.00-2.59E03 |
| 80JJ1 | 41.96 | 27.35-139.43 |
| 203J1 | 43.85 | 23.18-69.51 |
| 149B1 | 44.70 | 36.73-54.28 |
| KR589 | 47.28 | 29.83-230.71[#] |
| 201HH2 | 49.94 | 23.83-351.77 |
| KB60F5-11 | 51.84 | 19.38-1313.75[#] |
| 158X10 | 52.25 | 43.13-77.84[#] |
| 149B1 | 53.51 | 40.52-68.89 |
| KB58A10-3 | 53.77 | ND |
| 201L3 | 55.01 | 41.01-78.96 |
| 158T3 | 58.07 | 39.59-211.13 |
| 184M2 | 60.54 | 26.57-411.88 |
| 149B1 | 65.00 | ND |
| 149B1 | 67.52 | 42.81-91.22 |
| 204G4 | 69.09 | 52.32-93.83 |
| KB59A58-4 | 70.35 | 48.90-144.90 |
| 201H2 | 71.11 | 52.40-130.35 |
| 203G2 | 81.93 | 57.13-226.33 |
| KB59A54-4 | 82.03 | 38.50-1.63E03 |
| 204I11 | 88.41 | 62.48-173.07 |
| 236B6 | 89.33 | 64.16-158.96 |
| KR1369 | 93.25 | 71.97-205.04[#] |
| KB63A5-3 | 94.52 | 51.56-542.46 |
| 204C3 | 125.45 | 85.26-427.67[#] |
| KR1209 | 128.14 | 91.57-294.56 |
| 185W3 | 130.61 | ND |
| KR625 | 160.36 | ND |
| 210B | 201.26 | 48.51-0.14E+06[#] |
| KB10H-5 | 214.25 | 87.97-8.22E+03 |
| KB68B57-1 | 264.30 | 48.51-8.95E+04[#] |
| 223L2 | 3.81E+02 | ND |
| KR136 | 7.83E+02 | — |
| T25 | 1.30E+03 | ND |
| KB61A18-1 | 2.58E+03 | ND |
| 147U2 | 3.67E+03 | ND |
| KR200 | 2.14E+05 | ND |
| KB59A54-5 | 3.32E+05 | ND |
| KB3F-3 | 4.07E+05 | ND |
| 187G1(bs) | 3.50E+07 | ND |
| MR559 | 20%** | n/a |
| KB42C17-13 | 26%** | n/a |
| 224F2 | 33%** | n/a |
| KR959 | 41%** | n/a |
| KB2C-4 | 42%** | n/a |
| 198H3 | 46%** | n/a |
| KR331 | 47%** | n/a |
| KB46 | 55%** | n/a |
| KB71A118-6 | 71%** | n/a |
| KB53B7-2 | 84%** | n/a |
| 187Y2 | ND | n/a |
| 185L12 | ND | ND |
| 186L9 | ND | n/a |
| KB54A1-6 | ND | n/a |
| 187L14 | ND | n/a |
| 187G1(b) | nt | nt |
| 187G1(s) | nt | nt |

EXAMPLE 19

Activity of Sporulated *Bacillus thuringiensis* Cultures on Corn Rootworm

Liquid cultures of either PS80JJ1, PS149B1 or PS167H2 were grown to sporulation in shake flasks and pelleted by centrifugation. Culture pellets were resuspended in water and assayed for activity against corn rootworm in top load bioassays as described earlier. The amounts of 14 kDa and 44.3 kDa proteins present in the culture pellets were estimated by densitometry and used to calculate specific activity expressed as LC50. Activity of each native *B. thuringiensis* strain is presented in Table 12 (WCRW top load bioassay of *B.t.* strains).

TABLE 12

| *B.t.* strain | LC$_{50}$ (μg/cm$^2$)* | 95% CL | Slope |
|---|---|---|---|
| PS80JJ1 | 6 | 4-8 | 1.5 |
| PS167H2 | 6 | 4-9 | 1.6 |
| PS149B1 | 8 | 4-12 | 1.8 |
| CryB cell blank | 4% | N/A | N/A |
| Water blank | 4% | N/A | N/A |

*Percentage mortality at top dose is provided for controls

EXAMPLE 20

Insertion and Expression of Toxin Genes Into Plants

One aspect of the subject invention is the transformation of plants with genes encoding the insecticidal toxin. The transformed plants are resistant to attack by the target pest.

The novel corn rootworm-active genes described here can be optimized for expression in other organisms. Maize optimized gene sequences encoding the 14 and 44 kDa PS80JJ1 toxins are disclosed in SEQ ID NO. 44 and SEQ ID NO. 45, respectively.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13 mp series, pACYC184, etc. Accordingly, the sequence encoding the *B.t.* toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1-46; and An et al. (1985) *EMBO J.* 4:277-287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978*] Mol. Gen. Genet.* 163:181-187). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831, which is hereby incorporated by reference. Also, advantageously, plants encoding a truncated toxin will be used. The truncated toxin typically will encode about 55% to about 80% of the full length toxin. Methods for creating synthetic *B.t.* genes for use in plants are known in the art.

EXAMPLE 21

Cloning of *B.t.* Genes Into Insect Viruses

A number of viruses are known to infect insects. These viruses include, for example, baculoviruses and entomopoxviruses. In one embodiment of the subject invention, genes encoding the insecticidal toxins, as described herein, can be placed within the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee (1990) *J. Gen. Virol.* 71:1535-1544) and Martens et al. (Martens, J. W. M., G. Honee, D. Zuidema, J. W. M. van Lent, B. Visser, J. M. Vlak (1990) *Appl. Environmental Microbiol.* 56(9):2764-2770).

All of the references cited herein are hereby incorporated by reference.

It should be understood that the examples and embodiments described herein are for illustrative purposes only and that various modifications or changes in light thereof will be suggested to persons skilled in the art and are to be included within the spirit and purview of this application and the scope of the appended claims.

The invention claimed is:

1. An isolated protein that has toxin activity against a corn rootworm, wherein a polynucleotide that codes for said protein hybridizes under stringent conditions with the full complement of a nucleotide sequence selected from the group consisting of SEQ ID NO:35, SEQ ID NO:40, and SEQ ID NO:44.

2. The protein of claim 1 wherein said protein has a molecular weight of between about 10 kDa and about 15 kDa, and said nucleotide sequence is NO:35.

3. The protein of claim 1 wherein said stringent conditions comprise a wash in 1×SSPE and 0.1% SDS at room temperature.

4. The protein of claim 1 wherein said stringent conditions comprise a wash in 0.2×SSPE and 0.1% SDS at room temperature.

5. The protein of claim 1 wherein said protein has a molecular weight of between about 10 kDa and about 15 kDa, and said nucleotide sequence is SEQ ID NO:40.

6. The protein of claim 1 wherein said protein has a molecular weight of between about 10 kDa and about 15 kDa, and said nucleotide sequence is SEQ ID NO:44.

* * * * *

UNITED STATES PATENT AND TRADEMARK OFFICE

CERTIFICATE OF CORRECTION

PATENT NO. : 7,355,003 B2
APPLICATION NO. : 11/037780
DATED : April 8, 2008
INVENTOR(S) : Kenneth E. Narva et al.

It is certified that error appears in the above-identified patent and that said Letters Patent is hereby corrected as shown below:

Column 18,
Line 48, “Theological” should read --rheological--.

Column 21,
Line 28, “I $$le” should read --Ile--.

Column 31,
Line 22, “Expression Purification” should read --Expression, Purification--.

Signed and Sealed this

Fourteenth Day of October, 2008

JON W. DUDAS

*Director of the United States Patent and Trademark Office*

```
                     SEQUENCE LISTING


<160> NUMBER OF SEQ ID NOS: 130

<210> SEQ ID NO 1
<211> LENGTH: 5
<212> TYPE: PRT
<213> ORGANISM: Bacillus thuringiensis

<400> SEQUENCE: 1

Met Leu Asp Thr Asn
  1               5


<210> SEQ ID NO 2
<211> LENGTH: 25
<212> TYPE: PRT
```

<213> ORGANISM: Bacillus thuringiensis

<400> SEQUENCE: 2

```
Met Leu Asp Thr Asn Lys Val Tyr Glu Ile Ser Asn Leu Ala Asn Gly
  1               5                  10                  15

Leu Tyr Thr Ser Thr Tyr Leu Ser Leu
             20                  25
```

<210> SEQ ID NO 3
<211> LENGTH: 24
<212> TYPE: PRT
<213> ORGANISM: Bacillus thuringiensis

<400> SEQUENCE: 3

```
Ser Ala Arg Glu Val His Ile Glu Ile Asn Asn Thr Arg His Thr Leu
  1               5                  10                  15

Gln Leu Glu Ala Lys Thr Lys Leu
             20
```

<210> SEQ ID NO 4
<211> LENGTH: 25
<212> TYPE: PRT
<213> ORGANISM: Bacillus thuringiensis

<400> SEQUENCE: 4

```
Met Leu Asp Thr Asn Lys Val Tyr Glu Ile Ser Asn His Ala Asn Gly
  1               5                  10                  15

Leu Tyr Ala Ala Thr Tyr Leu Ser Leu
             20                  25
```

<210> SEQ ID NO 5
<211> LENGTH: 50
<212> TYPE: PRT
<213> ORGANISM: Bacillus thuringiensis
<220> FEATURE:
<221> NAME/KEY: Misc_feature
<222> LOCATION: (35)
<223> OTHER INFORMATION: Xaa may be any naturally-occurring amino acid

<400> SEQUENCE: 5

```
Ser Ala Arg Glu Val His Ile Asp Val Asn Asn Lys Thr Gly His Thr
  1               5                  10                  15

Leu Gln Leu Glu Asp Lys Thr Lys Leu Asp Gly Gly Arg Trp Arg Thr
             20                  25                  30

Ser Pro Xaa Asn Val Ala Asn Asp Gln Ile Lys Thr Phe Val Ala Glu
         35                  40                  45

Ser Asn
     50
```

<210> SEQ ID NO 6
<211> LENGTH: 25
<212> TYPE: PRT
<213> ORGANISM: Bacillus thuringiensis

<400> SEQUENCE: 6

```
Met Leu Asp Thr Asn Lys Ile Tyr Glu Ile Ser Asn Tyr Ala Asn Gly
  1               5                  10                  15

Leu His Ala Ala Thr Tyr Leu Ser Leu
             20                  25
```

<210> SEQ ID NO 7
<211> LENGTH: 25

-continued

```
<212> TYPE: PRT
<213> ORGANISM: Bacillus thuringiensis

<400> SEQUENCE: 7

Ser Ala Arg Glu Val His Ile Asp Val Asn Asn Lys Thr Gly His Thr
  1               5                  10                  15

Leu Gln Leu Glu Asp Lys Thr Lys Leu
             20                  25


<210> SEQ ID NO 8
<211> LENGTH: 29
<212> TYPE: DNA
<213> ORGANISM: Artificial Sequence
<220> FEATURE:
<223> OTHER INFORMATION: Oligonucleotide probe for gene encoding PS80JJ1
      44.3 kDa toxin and forward primer for PS149B1 and PS167H2
<220> FEATURE:
<221> NAME/KEY: misc_feature
<222> LOCATION: (4)
<223> OTHER INFORMATION: n is a, c, g or t
<220> FEATURE:
<221> NAME/KEY: misc_feature
<222> LOCATION: (6)
<223> OTHER INFORMATION: n is a, c, g or t
<220> FEATURE:
<221> NAME/KEY: misc_feature
<222> LOCATION: (12)
<223> OTHER INFORMATION: n is a, c, g or t
<220> FEATURE:
<221> NAME/KEY: misc_feature
<222> LOCATION: (21)
<223> OTHER INFORMATION: n is a, c, g or t

<400> SEQUENCE: 8

atgntngata cnaataaagt ntatgaaat                                        29


<210> SEQ ID NO 9
<211> LENGTH: 26
<212> TYPE: DNA
<213> ORGANISM: Artificial Sequence
<220> FEATURE:
<223> OTHER INFORMATION: Reverse primer for PS149B1 and PS167H2

<400> SEQUENCE: 9

ggattatcta tctctgagtg ttcttg                                           26


<210> SEQ ID NO 10
<211> LENGTH: 1158
<212> TYPE: DNA
<213> ORGANISM: Bacillus thuringiensis

<400> SEQUENCE: 10

atgttagata ctaataaagt ttatgaaata agcaatcttg ctaatggatt atatacatca     60

acttatttaa gtcttgatga ttcaggtgtt agtttaatga gtaaaaagga tgaagatatt    120

gatgattaca atttaaaatg gtttttattt cctattgata ataatcaata tattattaca    180

agctatggag ctaataattg taaagtttgg aatgttaaaa atgataaaat aaatgtttca    240

acttattctt caacaaactc tgtacaaaaa tggcaaataa aagctaaaga ttcttcatat    300

ataatacaaa gtgataatgg aaaggtctta acagcaggag taggtcaatc tcttggaata    360

gtacgcctaa ctgatgaatt tccagagaat tctaaccaac aatggaattt aactcctgta    420

caaacaattc aactcccaca aaaacctaaa atagatgaaa aattaaaaga tcatcctgaa    480

tattcagaaa ccggaaatat aaatcctaaa acaactcctc aattaatggg atggacatta    540

gtaccttgta ttatggtaaa tgattcaaaa atagataaaa acactcaaat taaaactact    600
```

-continued

```
ccatattata tttttaaaaa atataaatac tggaatctag caaaaggaag taatgtatct     660

ttacttccac atcaaaaaag atcatatgat tatgaatggg gtacagaaaa aaatcaaaaa     720

acaactatta ttaatacagt aggattgcaa attaatatag attcaggaat gaaatttgaa     780

gtaccagaag taggaggagg tacagaagac ataaaaacac aattaactga agaattaaaa     840

gttgaatata gcactgaaac caaaataatg acgaaatatc aagaacactc agagatagat     900

aatccaacta atcaaccaat gaattctata ggacttctta tttatacttc tttagaatta     960

tatcgatata acggtacaga aattaagata atggacatag aaacttcaga tcatgatact    1020

tacactctta cttcttatcc aaatcataaa gaagcattat tacttctcac aaaccattcg    1080

tatgaagaag tagaagaaat aacaaaaata cctaagcata cacttataaa attgaaaaaa    1140

cattatttta aaaaataa                                                   1158
```

```
<210> SEQ ID NO 11
<211> LENGTH: 385
<212> TYPE: PRT
<213> ORGANISM: Bacillus thuringiensis

<400> SEQUENCE: 11

Met Leu Asp Thr Asn Lys Val Tyr Glu Ile Ser Asn Leu Ala Asn Gly
  1               5                  10                  15

Leu Tyr Thr Ser Thr Tyr Leu Ser Leu Asp Asp Ser Gly Val Ser Leu
             20                  25                  30

Met Ser Lys Lys Asp Glu Asp Ile Asp Asp Tyr Asn Leu Lys Trp Phe
         35                  40                  45

Leu Phe Pro Ile Asp Asn Asn Gln Tyr Ile Ile Thr Ser Tyr Gly Ala
     50                  55                  60

Asn Asn Cys Lys Val Trp Asn Val Lys Asn Asp Lys Ile Asn Val Ser
 65                  70                  75                  80

Thr Tyr Ser Ser Thr Asn Ser Val Gln Lys Trp Gln Ile Lys Ala Lys
                 85                  90                  95

Asp Ser Ser Tyr Ile Ile Gln Ser Asp Asn Gly Lys Val Leu Thr Ala
            100                 105                 110

Gly Val Gly Gln Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Lys Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Thr Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
            260                 265                 270
```

```
Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350

Leu Leu Leu Leu Thr Asn His Ser Tyr Glu Glu Val Glu Glu Ile Thr
        355                 360                 365

Lys Ile Pro Lys His Thr Leu Ile Lys Leu Lys Lys His Tyr Phe Lys
    370                 375                 380

Lys
385


<210> SEQ ID NO 12
<211> LENGTH: 834
<212> TYPE: DNA
<213> ORGANISM: Bacillus thuringiensis

<400> SEQUENCE: 12

ggactatatg cagcaactta tttaagttta gatgattcag gtgttagttt aatgaataaa      60

aatgatgatg atattgatga ttataactta aaatggtttt tatttcctat tgatgatgat     120

caatatatta ttacaagcta tgcagcaaat aattgtaaag tttggaatgt taataatgat     180

aaaataaatg tttcgactta ttcttcaaca aattcaatac aaaaatggca aataaaagct     240

aatggttctt catatgtaat acaaagtgat aatggaaaag tcttaacagc aggaaccggt     300

caagctcttg gattgatacg tttaactgat gaatcctcaa ataatcccaa tcaacaatgg     360

aatttaactt ctgtacaaac aattcaactt ccacaaaaac ctataataga tacaaaatta     420

aaagattatc ccaaatattc accaactgga aatatagata atggaacatc tcctcaatta     480

atgggatgga cattagtacc ttgtattatg gtaaatgatc caaatataga taaaaatact     540

caaattaaaa ctactccata ttatatttta aaaaaatatc aatattggca acgagcagta     600

ggaagtaatg tagctttacg tccacatgaa aaaaaatcat atacttatga atggggcaca     660

gaaatagatc aaaaaacaac aattataaat acattaggat ttcaaatcaa tatagattca     720

ggaatgaaat ttgatatacc agaagtaggt ggaggtacag atgaaataaa aacacaacta     780

aatgaagaat taaaaataga atatagtcat gaaactaaaa taatggaaaa atat           834


<210> SEQ ID NO 13
<211> LENGTH: 278
<212> TYPE: PRT
<213> ORGANISM: Bacillus thuringiensis

<400> SEQUENCE: 13

Gly Leu Tyr Ala Ala Thr Tyr Leu Ser Leu Asp Asp Ser Gly Val Ser
  1               5                  10                  15

Leu Met Asn Lys Asn Asp Asp Asp Ile Asp Asp Tyr Asn Leu Lys Trp
            20                  25                  30

Phe Leu Phe Pro Ile Asp Asp Asp Gln Tyr Ile Ile Thr Ser Tyr Ala
        35                  40                  45

Ala Asn Asn Cys Lys Val Trp Asn Val Asn Asn Asp Lys Ile Asn Val
```

-continued

```
     50                  55                  60

Ser Thr Tyr Ser Ser Thr Asn Ser Ile Gln Lys Trp Gln Ile Lys Ala
 65                 70                  75                  80

Asn Gly Ser Ser Tyr Val Ile Gln Ser Asp Asn Gly Lys Val Leu Thr
                85                  90                  95

Ala Gly Thr Gly Gln Ala Leu Gly Leu Ile Arg Leu Thr Asp Glu Ser
            100                 105                 110

Ser Asn Asn Pro Asn Gln Gln Trp Asn Leu Thr Ser Val Gln Thr Ile
        115                 120                 125

Gln Leu Pro Gln Lys Pro Ile Ile Asp Thr Lys Leu Lys Asp Tyr Pro
    130                 135                 140

Lys Tyr Ser Pro Thr Gly Asn Ile Asp Asn Gly Thr Ser Pro Gln Leu
145                 150                 155                 160

Met Gly Trp Thr Leu Val Pro Cys Ile Met Val Asn Asp Pro Asn Ile
                165                 170                 175

Asp Lys Asn Thr Gln Ile Lys Thr Thr Pro Tyr Tyr Ile Leu Lys Lys
            180                 185                 190

Tyr Gln Tyr Trp Gln Arg Ala Val Gly Ser Asn Val Ala Leu Arg Pro
        195                 200                 205

His Glu Lys Lys Ser Tyr Thr Tyr Glu Trp Gly Thr Glu Ile Asp Gln
    210                 215                 220

Lys Thr Thr Ile Ile Asn Thr Leu Gly Phe Gln Ile Asn Ile Asp Ser
225                 230                 235                 240

Gly Met Lys Phe Asp Ile Pro Glu Val Gly Gly Gly Thr Asp Glu Ile
                245                 250                 255

Lys Thr Gln Leu Asn Glu Glu Leu Lys Ile Glu Tyr Ser His Glu Thr
            260                 265                 270

Lys Ile Met Glu Lys Tyr
        275
```

<210> SEQ ID NO 14
<211> LENGTH: 829
<212> TYPE: DNA
<213> ORGANISM: Bacillus thuringiensis

<400> SEQUENCE: 14

```
acatgcagca acttatttaa gtttagatga ttcaggtgtt agtttaatga ataaaaatga     60

tgatgatatt gatgactata atttaaggtg gtttttattt cctattgatg ataatcaata    120

tattattaca agctacgcag cgaataattg taaggtttgg aatgttaata atgataaaat    180

aaatgtttca acttattctt caacaaactc gatacagaaa tggcaaataa aagctaatgc    240

ttcttcgtat gtaatacaaa gtaataatgg gaaagttcta acagcaggaa ccggtcaatc    300

tcttggatta atacgtttaa cggatgaatc accagataat cccaatcaac aatggaattt    360

aactcctgta caaacaattc aactcccacc aaaacctaca atagatacaa agttaaaaga    420

ttaccccaaa tattcacaaa ctggcaatat agacaaggga acacctcctc aattaatggg    480

atggacatta ataccttgta ttatggtaaa tgatcccaat atagataaaa acactcaaat    540

caaaactact ccatattata ttttaaaaaa atatcaatat tggcaacaag cagtaggaag    600

taatgtagct ttacgtccgc atgaaaaaaa atcatatgct tatgagtggg gtacagaaat    660

agatcaaaaa acaactatca ttaatacatt aggatttcag attaatatag attcgggaat    720

gaaatttgat ataccagaag taggtggagg tacagatgaa ataaaaacac aattaaacga    780

agaattaaaa atagaatata gccgtgaaac caaaataatg gaaaaatat                829
```

<210> SEQ ID NO 15
<211> LENGTH: 276
<212> TYPE: PRT
<213> ORGANISM: Bacillus thuringiensis

<400> SEQUENCE: 15

```
His Ala Ala Thr Tyr Leu Ser Leu Asp Asp Ser Gly Val Ser Leu Met
  1               5                  10                  15

Asn Lys Asn Asp Asp Asp Ile Asp Asp Tyr Asn Leu Arg Trp Phe Leu
             20                  25                  30

Phe Pro Ile Asp Asp Asn Gln Tyr Ile Ile Thr Ser Tyr Ala Ala Asn
         35                  40                  45

Asn Cys Lys Val Trp Asn Val Asn Asn Asp Lys Ile Asn Val Ser Thr
     50                  55                  60

Tyr Ser Ser Thr Asn Ser Ile Gln Lys Trp Gln Ile Lys Ala Asn Ala
 65                  70                  75                  80

Ser Ser Tyr Val Ile Gln Ser Asn Asn Gly Lys Val Leu Thr Ala Gly
                 85                  90                  95

Thr Gly Gln Ser Leu Gly Leu Ile Arg Leu Thr Asp Glu Ser Pro Asp
            100                 105                 110

Asn Pro Asn Gln Gln Trp Asn Leu Thr Pro Val Gln Thr Ile Gln Leu
        115                 120                 125

Pro Pro Lys Pro Thr Ile Asp Thr Lys Leu Lys Asp Tyr Pro Lys Tyr
    130                 135                 140

Ser Gln Thr Gly Asn Ile Asp Lys Gly Thr Pro Pro Gln Leu Met Gly
145                 150                 155                 160

Trp Thr Leu Ile Pro Cys Ile Met Val Asn Asp Pro Asn Ile Asp Lys
                165                 170                 175

Asn Thr Gln Ile Lys Thr Thr Pro Tyr Tyr Ile Leu Lys Lys Tyr Gln
            180                 185                 190

Tyr Trp Gln Gln Ala Val Gly Ser Asn Val Ala Leu Arg Pro His Glu
        195                 200                 205

Lys Lys Ser Tyr Ala Tyr Glu Trp Gly Thr Glu Ile Asp Gln Lys Thr
    210                 215                 220

Thr Ile Ile Asn Thr Leu Gly Phe Gln Ile Asn Ile Asp Ser Gly Met
225                 230                 235                 240

Lys Phe Asp Ile Pro Glu Val Gly Gly Gly Thr Asp Glu Ile Lys Thr
                245                 250                 255

Gln Leu Asn Glu Glu Leu Lys Ile Glu Tyr Ser Arg Glu Thr Lys Ile
            260                 265                 270

Met Glu Lys Tyr
        275
```

<210> SEQ ID NO 16
<211> LENGTH: 7
<212> TYPE: PRT
<213> ORGANISM: Artificial sequence
<220> FEATURE:
<223> OTHER INFORMATION: Peptide sequence used in primer design

<400> SEQUENCE: 16

```
Asp Ile Asp Asp Tyr Asn Leu
  1               5
```

<210> SEQ ID NO 17
<211> LENGTH: 7

```
<212> TYPE: PRT
<213> ORGANISM: Artificial sequence
<220> FEATURE:
<223> OTHER INFORMATION: Peptide sequence used in primer design

<400> SEQUENCE: 17

Trp Phe Leu Phe Pro Ile Asp
  1               5


<210> SEQ ID NO 18
<211> LENGTH: 8
<212> TYPE: PRT
<213> ORGANISM: Artificial sequence
<220> FEATURE:
<223> OTHER INFORMATION: Peptide sequence used in primer design

<400> SEQUENCE: 18

Gln Ile Lys Thr Thr Pro Tyr Tyr
  1               5


<210> SEQ ID NO 19
<211> LENGTH: 6
<212> TYPE: PRT
<213> ORGANISM: Artificial sequence
<220> FEATURE:
<223> OTHER INFORMATION: Peptide sequence used in primer design

<400> SEQUENCE: 19

Tyr Glu Trp Gly Thr Glu
  1               5


<210> SEQ ID NO 20
<211> LENGTH: 21
<212> TYPE: DNA
<213> ORGANISM: Artificial Sequence
<220> FEATURE:
<223> OTHER INFORMATION: Nucleotide sequence corresponding to the
      peptide of SEQ ID NO:16
<220> FEATURE:
<221> NAME/KEY: misc_feature
<222> LOCATION: (6)
<223> OTHER INFORMATION: n is a, c, g or t
<220> FEATURE:
<221> NAME/KEY: misc_feature
<222> LOCATION: (12)
<223> OTHER INFORMATION: n is a, c, g or t
<220> FEATURE:
<221> NAME/KEY: misc_feature
<222> LOCATION: (21)
<223> OTHER INFORMATION: n is a, c, g or t

<400> SEQUENCE: 20

gatatngatg antayaaytt n                                                21


<210> SEQ ID NO 21
<211> LENGTH: 21
<212> TYPE: DNA
<213> ORGANISM: Artificial Sequence
<220> FEATURE:
<223> OTHER INFORMATION: Nucleotide sequence corresponding to the
      peptide of SEQ ID NO:17
<220> FEATURE:
<221> NAME/KEY: misc_feature
<222> LOCATION: (9)
<223> OTHER INFORMATION: n is a, c, g or t
<220> FEATURE:
<221> NAME/KEY: misc_feature
<222> LOCATION: (15)
<223> OTHER INFORMATION: n is a, c, g or t
<220> FEATURE:
<221> NAME/KEY: misc_feature
```

<222> LOCATION: (18)
<223> OTHER INFORMATION: n is a, c, g or t
<220> FEATURE:
<221> NAME/KEY: misc_feature
<222> LOCATION: (21)
<223> OTHER INFORMATION: n is a, c, g or t

<400> SEQUENCE: 21
tggtttttnt ttccnatnga n 21

<210> SEQ ID NO 22
<211> LENGTH: 24
<212> TYPE: DNA
<213> ORGANISM: Artificial Sequence
<220> FEATURE:
<223> OTHER INFORMATION: Nucleotide sequence corresponding to the peptide of SEQ ID NO:18
<220> FEATURE:
<221> NAME/KEY: misc_feature
<222> LOCATION: (6)
<223> OTHER INFORMATION: n is a, c, g or t
<220> FEATURE:
<221> NAME/KEY: misc_feature
<222> LOCATION: (12)
<223> OTHER INFORMATION: n is a, c, g or t
<220> FEATURE:
<221> NAME/KEY: misc_feature
<222> LOCATION: (15)
<223> OTHER INFORMATION: n is a, c, g or t

<400> SEQUENCE: 22
caaatnaaaa cnacnccata ttat 24

<210> SEQ ID NO 23
<211> LENGTH: 18
<212> TYPE: DNA
<213> ORGANISM: Artificial Sequence
<220> FEATURE:
<223> OTHER INFORMATION: Nucleotide sequence corresponding to the peptide of SEQ ID NO:19
<220> FEATURE:
<221> NAME/KEY: misc_feature
<222> LOCATION: (3)
<223> OTHER INFORMATION: n is a, c, g or t
<220> FEATURE:
<221> NAME/KEY: misc_feature
<222> LOCATION: (6)
<223> OTHER INFORMATION: n is a, c, g or t
<220> FEATURE:
<221> NAME/KEY: misc_feature
<222> LOCATION: (12)
<223> OTHER INFORMATION: n is a, c, g or t

<400> SEQUENCE: 23
tangantggg gnacagaa 18

<210> SEQ ID NO 24
<211> LENGTH: 24
<212> TYPE: DNA
<213> ORGANISM: Artificial Sequence
<220> FEATURE:
<223> OTHER INFORMATION: Reverse primer based on the reverse complement of SEQ ID NO:22
<220> FEATURE:
<221> NAME/KEY: misc_feature
<222> LOCATION: (10)
<223> OTHER INFORMATION: n is a, c, g or t
<220> FEATURE:
<221> NAME/KEY: misc_feature
<222> LOCATION: (13)
<223> OTHER INFORMATION: n is a, c, g or t
<220> FEATURE:
<221> NAME/KEY: misc_feature

```
<222> LOCATION: (19)
<223> OTHER INFORMATION: n is a, c, g or t

<400> SEQUENCE: 24

ataatatggn gtngttttna tttg                                             24


<210> SEQ ID NO 25
<211> LENGTH: 18
<212> TYPE: DNA
<213> ORGANISM: Artificial Sequence
<220> FEATURE:
<223> OTHER INFORMATION: Reverse primer based on the reverse complement
      of SEQ ID NO:23
<220> FEATURE:
<221> NAME/KEY: misc_feature
<222> LOCATION: (7)
<223> OTHER INFORMATION: n is a, c, g or t
<220> FEATURE:
<221> NAME/KEY: misc_feature
<222> LOCATION: (13)
<223> OTHER INFORMATION: n is a, c, g or t
<220> FEATURE:
<221> NAME/KEY: misc_feature
<222> LOCATION: (16)
<223> OTHER INFORMATION: n is a, c, g or t

<400> SEQUENCE: 25

ttctgtnccc cantcnta                                                    18


<210> SEQ ID NO 26
<211> LENGTH: 18
<212> TYPE: DNA
<213> ORGANISM: Artificial Sequence
<220> FEATURE:
<223> OTHER INFORMATION: Forward primer based on the pS80JJ1 44.3 kDa
      toxin

<400> SEQUENCE: 26

ctcaaagcgg atcaggag                                                    18


<210> SEQ ID NO 27
<211> LENGTH: 20
<212> TYPE: DNA
<213> ORGANISM: Artificial Sequence
<220> FEATURE:
<223> OTHER INFORMATION: Reverse primer based on the pS80JJ1 44.3 kDa
      toxin

<400> SEQUENCE: 27

gcgtattcgg atatgcttgg                                                  20


<210> SEQ ID NO 28
<211> LENGTH: 386
<212> TYPE: PRT
<213> ORGANISM: Artificial Sequence
<220> FEATURE:
<223> OTHER INFORMATION: Generic sequence representing a new class of
      toxins
<220> FEATURE:
<221> NAME/KEY: Misc_feature
<222> LOCATION: (1)..(20)
<223> OTHER INFORMATION: Xaa may be any naturally-occurring amino acid
<220> FEATURE:
<221> NAME/KEY: Misc_feature
<222> LOCATION: (34)
<223> OTHER INFORMATION: Xaa may be any naturally-occurring amino acid
<220> FEATURE:
<221> NAME/KEY: Misc_feature
<222> LOCATION: (36)
<223> OTHER INFORMATION: Xaa may be any naturally-occurring amino acid
<220> FEATURE:
```

<221> NAME/KEY: Misc_feature
<222> LOCATION: (38)
<223> OTHER INFORMATION: Xaa may be any naturally-occurring amino acid
<220> FEATURE:
<221> NAME/KEY: Misc_feature
<222> LOCATION: (46)
<223> OTHER INFORMATION: Xaa may be any naturally-occurring amino acid
<220> FEATURE:
<221> NAME/KEY: Misc_feature
<222> LOCATION: (54)..(55)
<223> OTHER INFORMATION: Xaa may be any naturally-occurring amino acid
<220> FEATURE:
<221> NAME/KEY: Misc_feature
<222> LOCATION: (63)
<223> OTHER INFORMATION: Xaa may be any naturally-occurring amino acid
<220> FEATURE:
<221> NAME/KEY: Misc_feature
<222> LOCATION: (73)
<223> OTHER INFORMATION: Xaa may be any naturally-occurring amino acid
<220> FEATURE:
<221> NAME/KEY: Misc_feature
<222> LOCATION: (88)
<223> OTHER INFORMATION: Xaa may be any naturally-occurring amino acid
<220> FEATURE:
<221> NAME/KEY: Misc_feature
<222> LOCATION: (96)..(97)
<223> OTHER INFORMATION: Xaa may be any naturally-occurring amino acid
<220> FEATURE:
<221> NAME/KEY: Misc_feature
<222> LOCATION: (101)
<223> OTHER INFORMATION: Xaa may be any naturally-occurring amino acid
<220> FEATURE:
<221> NAME/KEY: Misc_feature
<222> LOCATION: (105)
<223> OTHER INFORMATION: Xaa may be any naturally-occurring amino acid
<220> FEATURE:
<221> NAME/KEY: Misc_feature
<222> LOCATION: (114)
<223> OTHER INFORMATION: Xaa may be any naturally-occurring amino acid
<220> FEATURE:
<221> NAME/KEY: Misc_feature
<222> LOCATION: (117)
<223> OTHER INFORMATION: Xaa may be any naturally-occurring amino acid
<220> FEATURE:
<221> NAME/KEY: Misc_feature
<222> LOCATION: (120)..(121)
<223> OTHER INFORMATION: Xaa may be any naturally-occurring amino acid
<220> FEATURE:
<221> NAME/KEY: Misc_feature
<222> LOCATION: (127)..(129)
<223> OTHER INFORMATION: Xaa may be any naturally-occurring amino acid
<220> FEATURE:
<221> NAME/KEY: Misc_feature
<222> LOCATION: (131)
<223> OTHER INFORMATION: Xaa may be any naturally-occurring amino acid
<220> FEATURE:
<221> NAME/KEY: Misc_feature
<222> LOCATION: (139)
<223> OTHER INFORMATION: Xaa may be any naturally-occurring amino acid
<220> FEATURE:
<221> NAME/KEY: Misc_feature
<222> LOCATION: (147)
<223> OTHER INFORMATION: Xaa may be any naturally-occurring amino acid
<220> FEATURE:
<221> NAME/KEY: Misc_feature
<222> LOCATION: (150)
<223> OTHER INFORMATION: Xaa may be any naturally-occurring amino acid
<220> FEATURE:
<221> NAME/KEY: Misc_feature
<222> LOCATION: (153)
<223> OTHER INFORMATION: Xaa may be any naturally-occurring amino acid
<220> FEATURE:
<221> NAME/KEY: Misc_feature
<222> LOCATION: (158)
<223> OTHER INFORMATION: Xaa may be any naturally-occurring amino acid
<220> FEATURE:
<221> NAME/KEY: Misc_feature
<222> LOCATION: (160)
<223> OTHER INFORMATION: Xaa may be any naturally-occurring amino acid
<220> FEATURE:
<221> NAME/KEY: Misc_feature
<222> LOCATION: (163)
<223> OTHER INFORMATION: Xaa may be any naturally-occurring amino acid
<220> FEATURE:
<221> NAME/KEY: Misc_feature
<222> LOCATION: (168)..(170)
<223> OTHER INFORMATION: Xaa may be any naturally-occurring amino acid
<220> FEATURE:
<221> NAME/KEY: Misc_feature
<222> LOCATION: (172)
<223> OTHER INFORMATION: Xaa may be any naturally-occurring amino acid
<220> FEATURE:
<221> NAME/KEY: Misc_feature
<222> LOCATION: (181)
<223> OTHER INFORMATION: Xaa may be any naturally-occurring amino acid
<220> FEATURE:
<221> NAME/KEY: Misc_feature
<222> LOCATION: (189)..(190)
<223> OTHER INFORMATION: Xaa may be any naturally-occurring amino acid
<220> FEATURE:
<221> NAME/KEY: Misc_feature
<222> LOCATION: (205)
<223> OTHER INFORMATION: Xaa may be any naturally-occurring amino acid
<220> FEATURE:
<221> NAME/KEY: Misc_feature
<222> LOCATION: (209)
<223> OTHER INFORMATION: Xaa may be any naturally-occurring amino acid
<220> FEATURE:
<221> NAME/KEY: Misc_feature
<222> LOCATION: (212)..(213)
<223> OTHER INFORMATION: Xaa may be any naturally-occurring amino acid
<220> FEATURE:
<221> NAME/KEY: Misc_feature
<222> LOCATION: (215)
<223> OTHER INFORMATION: Xaa may be any naturally-occurring amino acid
<220> FEATURE:
<221> NAME/KEY: Misc_feature
<222> LOCATION: (220)
<223> OTHER INFORMATION: Xaa may be any naturally-occurring amino acid
<220> FEATURE:
<221> NAME/KEY: Misc_feature
<222> LOCATION: (222)
<223> OTHER INFORMATION: Xaa may be any naturally-occurring amino acid
<220> FEATURE:
<221> NAME/KEY: Misc_feature
<222> LOCATION: (225)
<223> OTHER INFORMATION: Xaa may be any naturally-occurring amino acid
<220> FEATURE:
<221> NAME/KEY: Misc_feature
<222> LOCATION: (227)
<223> OTHER INFORMATION: Xaa may be any naturally-occurring amino acid
<220> FEATURE:
<221> NAME/KEY: Misc_feature
<222> LOCATION: (230)
<223> OTHER INFORMATION: Xaa may be any naturally-occurring amino acid
<220> FEATURE:
<221> NAME/KEY: Misc_feature
<222> LOCATION: (237)..(238)
<223> OTHER INFORMATION: Xaa may be any naturally-occurring amino acid
<220> FEATURE:
<221> NAME/KEY: Misc_feature
<222> LOCATION: (247)
<223> OTHER INFORMATION: Xaa may be any naturally-occurring amino acid
<220> FEATURE:
<221> NAME/KEY: Misc_feature
<222> LOCATION: (249)
<223> OTHER INFORMATION: Xaa may be any naturally-occurring amino acid
<220> FEATURE:
<221> NAME/KEY: Misc_feature
<222> LOCATION: (260)..(261)
<223> OTHER INFORMATION: Xaa may be any naturally-occurring amino acid
<220> FEATURE:
<221> NAME/KEY: Misc_feature
<222> LOCATION: (269)..(270)
<223> OTHER INFORMATION: Xaa may be any naturally-occurring amino acid
<220> FEATURE:
<221> NAME/KEY: Misc_feature
<222> LOCATION: (276)

-continued

<223> OTHER INFORMATION: Xaa may be any naturally-occurring amino acid
<220> FEATURE:
<221> NAME/KEY: Misc_feature
<222> LOCATION: (281)
<223> OTHER INFORMATION: Xaa may be any naturally-occurring amino acid
<220> FEATURE:
<221> NAME/KEY: Misc_feature
<222> LOCATION: (285)
<223> OTHER INFORMATION: Xaa may be any naturally-occurring amino acid
<220> FEATURE:
<221> NAME/KEY: Misc_feature
<222> LOCATION: (291)
<223> OTHER INFORMATION: Xaa may be any naturally-occurring amino acid
<220> FEATURE:
<221> NAME/KEY: Misc_feature
<222> LOCATION: (294)..(386)
<223> OTHER INFORMATION: Xaa may be any naturally-occurring amino acid

<400> SEQUENCE: 28

```
Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Thr Tyr Leu Ser Leu Asp Asp Ser Gly Val Ser Leu
             20                  25                  30

Met Xaa Lys Xaa Asp Xaa Asp Ile Asp Asp Tyr Asn Leu Xaa Trp Phe
         35                  40                  45

Leu Phe Pro Ile Asp Xaa Xaa Gln Tyr Ile Ile Thr Ser Tyr Xaa Ala
     50                  55                  60

Asn Asn Cys Lys Val Trp Asn Val Xaa Asn Asp Lys Ile Asn Val Ser
 65                  70                  75                  80

Thr Tyr Ser Ser Thr Asn Ser Xaa Gln Lys Trp Gln Ile Lys Ala Xaa
                 85                  90                  95

Xaa Ser Ser Tyr Xaa Ile Gln Ser Xaa Asn Gly Lys Val Leu Thr Ala
            100                 105                 110

Gly Xaa Gly Gln Xaa Leu Gly Xaa Xaa Arg Leu Thr Asp Glu Xaa Xaa
        115                 120                 125

Xaa Asn Xaa Asn Gln Gln Trp Asn Leu Thr Xaa Val Gln Thr Ile Gln
    130                 135                 140

Leu Pro Xaa Lys Pro Xaa Ile Asp Xaa Lys Leu Lys Asp Xaa Pro Xaa
145                 150                 155                 160

Tyr Ser Xaa Thr Gly Asn Ile Xaa Xaa Xaa Thr Xaa Pro Gln Leu Met
                165                 170                 175

Gly Trp Thr Leu Xaa Pro Cys Ile Met Val Asn Asp Xaa Xaa Ile Asp
            180                 185                 190

Lys Asn Thr Gln Ile Lys Thr Thr Pro Tyr Tyr Ile Xaa Lys Lys Tyr
        195                 200                 205

Xaa Tyr Trp Xaa Xaa Ala Xaa Gly Ser Asn Val Xaa Leu Xaa Pro His
    210                 215                 220

Xaa Lys Xaa Ser Tyr Xaa Tyr Glu Trp Gly Thr Glu Xaa Xaa Gln Lys
225                 230                 235                 240

Thr Thr Ile Ile Asn Thr Xaa Gly Xaa Gln Ile Asn Ile Asp Ser Gly
                245                 250                 255

Met Lys Phe Xaa Xaa Pro Glu Val Gly Gly Gly Thr Xaa Xaa Ile Lys
            260                 265                 270

Thr Gln Leu Xaa Glu Glu Leu Lys Xaa Glu Tyr Ser Xaa Glu Thr Lys
        275                 280                 285

Ile Met Xaa Lys Tyr Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320
```

```
Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa
385


<210> SEQ ID NO 29
<211> LENGTH: 28
<212> TYPE: DNA
<213> ORGANISM: Artificial Sequence
<220> FEATURE:
<223> OTHER INFORMATION: Oligonucleotide probe used according to the
      subject invention
<220> FEATURE:
<221> NAME/KEY: misc_feature
<222> LOCATION: (2)
<223> OTHER INFORMATION: n is a, c, g or t
<220> FEATURE:
<221> NAME/KEY: misc_feature
<222> LOCATION: (8)
<223> OTHER INFORMATION: n is a, c, g or t
<220> FEATURE:
<221> NAME/KEY: misc_feature
<222> LOCATION: (14)
<223> OTHER INFORMATION: n is a, c, g or t
<220> FEATURE:
<221> NAME/KEY: misc_feature
<222> LOCATION: (20)
<223> OTHER INFORMATION: n is a, c, g or t

<400> SEQUENCE: 29

gngaagtnca tatngaaatn aataatac                                        28


<210> SEQ ID NO 30
<211> LENGTH: 2015
<212> TYPE: DNA
<213> ORGANISM: Bacillus thuringiensis

<400> SEQUENCE: 30

attaatttta tggaggttga tatttatgtc agctcgcgaa gtacacattg aaataaacaa      60

taaaacacgt catacattac aattagagga taaaactaaa cttagcggcg gtagatggcg     120

aacatcacct acaaatgttg ctcgtgatac aattaaaaca tttgtagcag aatcacatgg     180

ttttatgaca ggagtagaag gtattatata ttttagtgta aacggagacg cagaaattag     240

tttacatttt gacaatcctt atataggttc taataaatgt gatggttctt ctgataaacc     300

tgaatatgaa gttattactc aaagcggatc aggagataaa tctcatgtga catatactat     360

tcagacagta tctttacgat tataaggaaa atttataaaa actgtatttt ttactaaaat     420

accaaaaaat acatatttat tttttggtat tttctaatat gaaatatgaa ttataaaaat     480

attaataaaa aaggtgataa aaattatgtt agatactaat aaagtttatg aaataagcaa     540

tcttgctaat ggattatata catcaactta tttaagtctt gatgattcag gtgttagttt     600

aatgagtaaa aaggatgaag atattgatga ttacaattta aaatggtttt tatttcctat     660

tgataataat caatatatta ttacaagcta tggagctaat aattgtaaag tttggaatgt     720

taaaaatgat aaaataaatg tttcaactta ttcttcaaca aactctgtac aaaaatggca     780
```

-continued

```
aataaaagct aaagattctt catatataat acaaagtgat aatggaaagg tcttaacagc    840

aggagtaggt caatctcttg gaatagtacg cctaactgat gaatttccag agaattctaa    900

ccaacaatgg aatttaactc ctgtacaaac aattcaactc ccacaaaaac ctaaaataga    960

tgaaaaatta aaagatcatc ctgaatattc agaaaccgga aatataaatc ctaaaacaac   1020

tcctcaatta atgggatgga cattagtacc ttgtattatg gtaaatgatt caaaaataga   1080

taaaaacact caaattaaaa ctactccata ttatattttt aaaaaatata aatactggaa   1140

tctagcaaaa ggaagtaatg tatctttact tccacatcaa aaaagatcat atgattatga   1200

atggggtaca gaaaaaaatc aaaaaacaac tattattaat acagtaggat tgcaaattaa   1260

tatagattca ggaatgaaat ttgaagtacc agaagtagga ggaggtacag aagacataaa   1320

aacacaatta actgaagaat taaaagttga atatagcact gaaaccaaaa taatgacgaa   1380

atatcaagaa cactcagaga tagataatcc aactaatcaa ccaatgaatt ctataggact   1440

tcttatttat acttctttag aattatatcg atataacggt acagaaatta agataatgga   1500

catagaaact tcagatcatg atacttacac tcttacttct tatccaaatc ataaagaagc   1560

attattactt ctcacaaacc attcgtatga agaagtagaa gaaataacaa aaatacctaa   1620

gcatacactt ataaaattga aaaaacatta ttttaaaaaa taaaaaacat aatatataaa   1680

tgactgatta atatctctcg aaaaggttct ggtgcaaaaa tagtgggata tgaaaaaagc   1740

aaaagattcc taacggaatg gaacattagg ctgttaaatc aaaaagttta ttgataaaat   1800

atatctgcct ttggacagac ttctcccctt ggagagtttg tcctttttttg accatatgca   1860

tagcttctat tccggcaatc atttttgtag ctgtttgcaa ggattttaat ccaagcatat   1920

ccgaatacgc tttttgataa ccgatgtctt gttcaatgat attgtttaat attttcacac   1980

gaattggcta ctgtgcggta tcctgtctcc tttat                              2015


<210> SEQ ID NO 31
<211> LENGTH: 360
<212> TYPE: DNA
<213> ORGANISM: Bacillus thuringiensis

<400> SEQUENCE: 31

atgtcagctc gcgaagtaca cattgaaata aacaataaaa cacgtcatac attacaatta     60

gaggataaaa ctaaacttag cggcggtaga tggcgaacat cacctacaaa tgttgctcgt    120

gatacaatta aaacatttgt agcagaatca catggtttta tgacaggagt agaaggtatt    180

atatatttta gtgtaaacgg agacgcagaa attagtttac attttgacaa tccttatata    240

ggttctaata aatgtgatgg ttcttctgat aaacctgaat atgaagttat tactcaaagc    300

ggatcaggag ataaatctca tgtgacatat actattcaga cagtatcttt acgattataa    360


<210> SEQ ID NO 32
<211> LENGTH: 119
<212> TYPE: PRT
<213> ORGANISM: Bacillus thuringiensis

<400> SEQUENCE: 32

Met Ser Ala Arg Glu Val His Ile Glu Ile Asn Asn Lys Thr Arg His
  1               5                  10                  15

Thr Leu Gln Leu Glu Asp Lys Thr Lys Leu Ser Gly Gly Arg Trp Arg
             20                  25                  30

Thr Ser Pro Thr Asn Val Ala Arg Asp Thr Ile Lys Thr Phe Val Ala
         35                  40                  45
```

-continued

```
Glu Ser His Gly Phe Met Thr Gly Val Glu Gly Ile Ile Tyr Phe Ser
     50                  55                  60

Val Asn Gly Asp Ala Glu Ile Ser Leu His Phe Asp Asn Pro Tyr Ile
 65                  70                  75                  80

Gly Ser Asn Lys Cys Asp Gly Ser Ser Asp Lys Pro Glu Tyr Glu Val
                 85                  90                  95

Ile Thr Gln Ser Gly Ser Gly Asp Lys Ser His Val Thr Tyr Thr Ile
            100                 105                 110

Gln Thr Val Ser Leu Arg Leu
        115


<210> SEQ ID NO 33
<211> LENGTH: 24
<212> TYPE: DNA
<213> ORGANISM: Artificial Sequence
<220> FEATURE:
<223> OTHER INFORMATION: Reverse oligonucleotide primer

<400> SEQUENCE: 33

catgagattt atctcctgat ccgc                                             24


<210> SEQ ID NO 34
<211> LENGTH: 2230
<212> TYPE: DNA
<213> ORGANISM: Bacillus thuringiensis

<400> SEQUENCE: 34

actatgacaa tgattatgac tgctgatgaa ttagctttat caataccagg atattctaaa      60

ccatcaaata taacaggaga taaaagtaaa catacattat ttactaatat aattggagat     120

attcaaataa aagatcaagc aacatttggg gttgtttttg atccccctct taatcgtatt     180

tcaggggctg aagaatcaag taagtttatt gatgtatatt atccttctga agatagtaac     240

cttaaatatt atcaatttat aaaagtagca attgattttg atattaatga agattttatt     300

aattttaata atcatgacaa tatagggata tttaattttg ttacacgaaa ttttttatta     360

aataatgaaa atgattaata aaaaatttaa tttgtataat atgtttattt tttgaaaatt     420

gaatgcatat attaatcgag tatgtgtaat aaattttaat tttatggagg ttgatattta     480

tgtcagcacg tgaagtacac attgatgtaa ataataagac aggtcataca ttacaattag     540

aagataaaac aaaacttgat ggtggtagat ggcgaacatc acctacaaat gttgctaatg     600

atcaaattaa aacatttgta gcagaatcac atggttttat gacaggtaca gaaggtacta     660

tatattatag tataaatgga gaagcagaaa ttagtttata ttttgacaat ccttattcag     720

gttctaataa atatgatggg cattccaata aaaatcaata tgaagttatt acccaaggag     780

gatcaggaaa tcaatctcat gttacgtata ctattcaaac tgtatcttca cgatatggga     840

ataattcata aaaaaatatt ttttttacg aaaataccaa aaaaattttt ttggtatttt       900

ctaatataat tcataaatat tttaataata aaattataag aaaaggtgat aaatattatg     960

ttagatacta ataaaattta tgaaataagt aattatgcta atggattaca tgcagcaact    1020

tatttaagtt tagatgattc aggtgttagt ttaatgaata aaaatgatga tgatattgat    1080

gactataatt taaggtggtt tttatttcct attgatgata atcaatatat tattacaagc    1140

tacgcagcga ataattgtaa ggtttggaat gttaataatg ataaaaataa tgtttcaact    1200

tattcttcaa caaactcgat acagaaatgg caaataaaag ctaatgcttc ttcgtatgta    1260

atacaaagta ataatgggaa agttctaaca gcaggaaccg gtcaatctct tggattaata    1320
```

-continued

```
cgtttaacgg atgaatcacc agataatccc aatcaacaat ggaatttaac tcctgtacaa   1380

acaattcaac tcccaccaaa acctacaata gatacaaagt taaaagatta ccccaaatat   1440

tcacaaactg gcaatataga caagggaaca cctcctcaat taatgggatg gacattaata   1500

ccttgtatta tggtaaatga tccaaatata gataaaaaca ctcaaatcaa aactactcca   1560

tattatattt taaaaaaata tcaatattgg caacaagcag taggaagtaa tgtagcttta   1620

cgtccgcatg aaaaaaaatc atatgcttat gagtggggta cagaaataga tcaaaaaaca   1680

actatcatta atacattagg atttcagatt aatatagatt cgggaatgaa atttgatata   1740

ccagaagtag gtggaggtac agatgaaata aaaacacaat taaacgaaga attaaaaata   1800

gaatatagcc gtgaaaccaa aataatggaa aaatatcagg aacaatcaga gatagataat   1860

ccaactgatc aatcaatgaa ttctatagga ttcctcacta ttacttcttt agaattatat   1920

cgatataatg gttcggaaat tagtgtaatg aaaattcaaa cttcagataa tgatacttac   1980

aatgtgacct cttatccaga tcatcaacaa gctctattac ttcttacaaa tcattcatat   2040

gaagaagtag aagaaataac aaatattccc aaaatatcac tgaaaaaatt aaaaaaatat   2100

tatttttaaa acataattat attttgatag ctttttaaaa ataaagattg ttcaaagtaa   2160

aatgaaagaa aatcttttat gaaactttaa tacaataaaa gaggaatatt ttcttataag   2220

tacttccttg                                                          2230
```

<210> SEQ ID NO 35
<211> LENGTH: 372
<212> TYPE: DNA
<213> ORGANISM: Bacillus thuringiensis

<400> SEQUENCE: 35

```
atgtcagcac gtgaagtaca cattgatgta aataataaga caggtcatac attacaatta     60

gaagataaaa caaaacttga tggtggtaga tggcgaacat cacctacaaa tgttgctaat    120

gatcaaatta aaacatttgt agcagaatca catggtttta tgacaggtac agaaggtact    180

atatattata gtataaatgg agaagcagaa attagtttat attttgacaa tccttattca    240

ggttctaata aatatgatgg gcattccaat aaaaatcaat atgaagttat tacccaagga    300

ggatcaggaa atcaatctca tgttacgtat actattcaaa ctgtatcttc acgatatggg    360

aataattcat aa                                                        372
```

<210> SEQ ID NO 36
<211> LENGTH: 123
<212> TYPE: PRT
<213> ORGANISM: Bacillus thuringiensis

<400> SEQUENCE: 36

```
Met Ser Ala Arg Glu Val His Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Phe Val Ala
         35                  40                  45

Glu Ser His Gly Phe Met Thr Gly Thr Glu Gly Thr Ile Tyr Tyr Ser
     50                  55                  60

Ile Asn Gly Glu Ala Glu Ile Ser Leu Tyr Phe Asp Asn Pro Tyr Ser
 65                  70                  75                  80

Gly Ser Asn Lys Tyr Asp Gly His Ser Asn Lys Asn Gln Tyr Glu Val
                 85                  90                  95
```

-continued

```
Ile Thr Gln Gly Gly Ser Gly Asn Gln Ser His Val Thr Tyr Thr Ile
            100                 105                 110

Gln Thr Val Ser Ser Arg Tyr Gly Asn Asn Ser
        115                 120


<210> SEQ ID NO 37
<211> LENGTH: 1152
<212> TYPE: DNA
<213> ORGANISM: Bacillus thuringiensis

<400> SEQUENCE: 37

atgttagata ctaataaaat ttatgaaata agtaattatg ctaatggatt acatgcagca      60

acttatttaa gtttagatga ttcaggtgtt agtttaatga ataaaaatga tgatgatatt     120

gatgactata atttaaggtg gtttttattt cctattgatg ataatcaata tattattaca     180

agctacgcag cgaataattg taaggtttgg aatgttaata atgataaaat aaatgtttca     240

acttattctt caacaaactc gatacagaaa tggcaaataa aagctaatgc ttcttcgtat     300

gtaatacaaa gtaataatgg gaaagttcta acagcaggaa ccggtcaatc tcttggatta     360

atacgtttaa cggatgaatc accagataat cccaatcaac aatggaattt aactcctgta     420

caaacaattc aactcccacc aaaacctaca atagatacaa agttaaaaga ttaccccaaa     480

tattcacaaa ctggcaatat agacaaggga acacctcctc aattaatggg atggacatta     540

ataccttgta ttatggtaaa tgatccaaat atagataaaa acactcaaat caaaactact     600

ccatattata ttttaaaaaa atatcaatat tggcaacaag cagtaggaag taatgtagct     660

ttacgtccgc atgaaaaaaa atcatatgct tatgagtggg gtacagaaat agatcaaaaa     720

acaactatca ttaatacatt aggatttcag attaatatag attcgggaat gaaatttgat     780

ataccagaag taggtggagg tacagatgaa ataaaaacac aattaaacga agaattaaaa     840

atagaatata gccgtgaaac caaaataatg gaaaaatatc aggaacaatc agagatagat     900

aatccaactg atcaatcaat gaattctata ggattcctca ctattacttc tttagaatta     960

tatcgatata atggttcgga aattagtgta atgaaaattc aaacttcaga taatgatact    1020

tacaatgtga cctcttatcc agatcatcaa caagctctat tacttcttac aaatcattca    1080

tatgaagaag tagaagaaat aacaaatatt cccaaaatat cactgaaaaa attaaaaaaa    1140

tattattttt aa                                                         1152


<210> SEQ ID NO 38
<211> LENGTH: 383
<212> TYPE: PRT
<213> ORGANISM: Bacillus thuringiensis

<400> SEQUENCE: 38

Met Leu Asp Thr Asn Lys Ile Tyr Glu Ile Ser Asn Tyr Ala Asn Gly
  1               5                  10                  15

Leu His Ala Ala Thr Tyr Leu Ser Leu Asp Asp Ser Gly Val Ser Leu
             20                  25                  30

Met Asn Lys Asn Asp Asp Asp Ile Asp Asp Tyr Asn Leu Arg Trp Phe
         35                  40                  45

Leu Phe Pro Ile Asp Asp Asn Gln Tyr Ile Ile Thr Ser Tyr Ala Ala
     50                  55                  60

Asn Asn Cys Lys Val Trp Asn Val Asn Asn Asp Lys Ile Asn Val Ser
 65                  70                  75                  80

Thr Tyr Ser Ser Thr Asn Ser Ile Gln Lys Trp Gln Ile Lys Ala Asn
```

-continued

```
                85                  90                  95

Ala Ser Ser Tyr Val Ile Gln Ser Asn Asn Gly Lys Val Leu Thr Ala
            100                 105                 110

Gly Thr Gly Gln Ser Leu Gly Leu Ile Arg Leu Thr Asp Glu Ser Pro
        115                 120                 125

Asp Asn Pro Asn Gln Gln Trp Asn Leu Thr Pro Val Gln Thr Ile Gln
    130                 135                 140

Leu Pro Pro Lys Pro Thr Ile Asp Thr Lys Leu Lys Asp Tyr Pro Lys
145                 150                 155                 160

Tyr Ser Gln Thr Gly Asn Ile Asp Lys Gly Thr Pro Pro Gln Leu Met
                165                 170                 175

Gly Trp Thr Leu Ile Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Gln Ala Val Gly Ser Asn Val Ala Leu Arg Pro His
    210                 215                 220

Glu Lys Lys Ser Tyr Ala Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser Arg Glu Thr Lys
        275                 280                 285

Ile Met Glu Lys Tyr Gln Glu Gln Ser Glu Ile Asp Asn Pro Thr Asp
    290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Ser Val Met Lys Ile Gln Thr Ser
                325                 330                 335

Asp Asn Asp Thr Tyr Asn Val Thr Ser Tyr Pro Asp His Gln Gln Ala
            340                 345                 350

Leu Leu Leu Leu Thr Asn His Ser Tyr Glu Glu Val Glu Glu Ile Thr
        355                 360                 365

Asn Ile Pro Lys Ile Ser Leu Lys Lys Leu Lys Lys Tyr Tyr Phe
    370                 375                 380


<210> SEQ ID NO 39
<211> LENGTH: 2132
<212> TYPE: DNA
<213> ORGANISM: Bacillus thuringiensis

<400> SEQUENCE: 39

gtatttcagg gggtgaagat tcaagtaagt ttattgatgt atattatcct tttgaagata      60

gtaattttaa atattatcaa tttataaaag tagcaattga ttttgatatt aatgaagatt     120

ttattaattt taataatcat gacaatatag ggatatttaa ttttgttaca cgaaattttt     180

tattaaataa tgaaaatgat gaataaaaaa tttaatttgt ttattatgtt tattttttga     240

aaattgaatg catatattaa tcgagtatgt ataataaatt ttaattttat ggaggttgat     300

atttatgtca gcacgtgaag tacacattga tgtaaataat aagacaggtc atacattaca     360

attagaagat aaaacaaaac ttgatggtgg tagatggcga acatcaccta caaatgttgc     420

taatgatcaa attaaaacat ttgtagcaga atcaaatggt tttatgacag gtacagaagg     480
```

-continued

```
tactatatat tatagtataa atggagaagc agaaattagt ttatattttg acaatccttt    540

tgcaggttct aataaatatg atggacattc caataaatct caatatgaaa ttattaccca    600

aggaggatca ggaaatcaat ctcatgttac gtatactatt caaaccacat cctcacgata    660

tgggcataaa tcataacaaa taattttta cgaaaatacc aaaaaataaa tatttttgg     720

tattttctaa tataaattac aaatatatta ataataaaat tataagaaaa ggtgataaag    780

attatgttag atactaataa agtttatgaa ataagcaatc atgctaatgg actatatgca    840

gcaacttatt taagtttaga tgattcaggt gttagtttaa tgaataaaaa tgatgatgat    900

attgatgatt ataacttaaa atggttttta tttcctattg atgatgatca atatattatt    960

acaagctatg cagcaaataa ttgtaaagtt tggaatgtta ataatgataa aataaatgtt   1020

tcgacttatt cttcaacaaa ttcaatacaa aaatggcaaa taaaagctaa tggttcttca   1080

tatgtaatac aaagtgataa tggaaaagtc ttaacagcag gaaccggtca agctcttgga   1140

ttgatacgtt taactgatga atcctcaaat aatcccaatc aacaatggaa tttaacttct   1200

gtacaaacaa ttcaacttcc acaaaaacct ataatagata caaaattaaa agattatccc   1260

aaatattcac caactggaaa tatagataat ggaacatctc ctcaattaat gggatggaca   1320

ttagtacctt gtattatggt aaatgatcca aatatagata aaaatactca aattaaaact   1380

actccatatt atattttaaa aaaatatcaa tattggcaac gagcagtagg aagtaatgta   1440

gctttacgtc cacatgaaaa aaaatcatat acttatgaat ggggcacaga aatagatcaa   1500

aaaacaacaa ttataaatac attaggattt caaatcaata tagattcagg aatgaaattt   1560

gatataccag aagtaggtgg aggtacagat gaaataaaaa cacaactaaa tgaagaatta   1620

aaaatagaat atagtcatga aactaaaata atggaaaaat atcaagaaca atctgaaata   1680

gataatccaa ctgatcaatc aatgaattct ataggatttc ttactattac ttccttagaa   1740

ttatatagat ataatggctc agaaattcgt ataatgcaaa ttcaaacctc agataatgat   1800

acttataatg ttacttctta tccaaatcat caacaagctt tattacttct tacaaatcat   1860

tcatatgaag aagtagaaga aataacaaat attcctaaaa gtacactaaa aaaattaaaa   1920

aaatattatt tttaaatatt gaaattagaa attatctaaa acaaaacgaa agataattta   1980

atctttaatt atttgtaaga taatcgtatt ttatttgtat taatttttat acaatataaa   2040

gtaatatctg tacgtgaaat tggtttcgct tcaatatcta atctcatctc atgtattaca   2100

tgcgtaatac cttcttgttc tgcttctaca ag                                 2132
```

<210> SEQ ID NO 40
<211> LENGTH: 372
<212> TYPE: DNA
<213> ORGANISM: Bacillus thuringiensis

<400> SEQUENCE: 40

```
atgtcagcac gtgaagtaca cattgatgta aataataaga caggtcatac attacaatta     60

gaagataaaa caaaacttga tggtggtaga tggcgaacat cacctacaaa tgttgctaat    120

gatcaaatta aaacatttgt agcagaatca aatggtttta tgacaggtac agaaggtact    180

atatattata gtataaatgg agaagcagaa attagtttat attttgacaa tccttttgca    240

ggttctaata aatatgatgg acattccaat aaatctcaat atgaaattat tacccaagga    300

ggatcaggaa atcaatctca tgttacgtat actattcaaa ccacatcctc acgatatggg    360

cataaatcat aa                                                        372
```

```
<210> SEQ ID NO 41
<211> LENGTH: 123
<212> TYPE: PRT
<213> ORGANISM: Bacillus thuringiensis

<400> SEQUENCE: 41

Met Ser Ala Arg Glu Val His Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Phe Val Ala
         35                  40                  45

Glu Ser Asn Gly Phe Met Thr Gly Thr Glu Gly Thr Ile Tyr Tyr Ser
     50                  55                  60

Ile Asn Gly Glu Ala Glu Ile Ser Leu Tyr Phe Asp Asn Pro Phe Ala
 65                  70                  75                  80

Gly Ser Asn Lys Tyr Asp Gly His Ser Asn Lys Ser Gln Tyr Glu Ile
                 85                  90                  95

Ile Thr Gln Gly Gly Ser Gly Asn Gln Ser His Val Thr Tyr Thr Ile
            100                 105                 110

Gln Thr Thr Ser Ser Arg Tyr Gly His Lys Ser
        115                 120


<210> SEQ ID NO 42
<211> LENGTH: 1241
<212> TYPE: DNA
<213> ORGANISM: Bacillus thuringiensis
<220> FEATURE:
<221> NAME/KEY: misc_feature
<222> LOCATION: (18)
<223> OTHER INFORMATION: n is a, c, g or t
<220> FEATURE:
<221> NAME/KEY: misc_feature
<222> LOCATION: (53)
<223> OTHER INFORMATION: n is a, c, g or t
<220> FEATURE:
<221> NAME/KEY: misc_feature
<222> LOCATION: (61)
<223> OTHER INFORMATION: n is a, c, g or t
<220> FEATURE:
<221> NAME/KEY: misc_feature
<222> LOCATION: (68)
<223> OTHER INFORMATION: n is a, c, g or t
<220> FEATURE:
<221> NAME/KEY: misc_feature
<222> LOCATION: (73)
<223> OTHER INFORMATION: n is a, c, g or t
<220> FEATURE:
<221> NAME/KEY: misc_feature
<222> LOCATION: (81)
<223> OTHER INFORMATION: n is a, c, g or t

<400> SEQUENCE: 42

wcdmtkdvrm wahkcmdndb ygtrawbmkg cwtkctgyhd cywagmawtd cvnwmhasrt      60

nchhtmsnwr manrgarcrr nwrgarhatg ttagatacta ataaagttta tgaaataagc     120

aatcatgcta atggactata tgcagcaact tatttaagtt tagatgattc aggtgttagt     180

ttaatgaata aaaatgatga tgatattgat gattataact taaaatggtt tttatttcct     240

attgatgatg atcaatatat tattacaagc tatgcagcaa ataattgtaa agtttggaat     300

gttaataatg ataaaaataa tgtttcgact tattcttcaa caaattcaat acaaaaatgg     360

caaataaaag ctaatggttc ttcatatgta atacaaagtg ataatggaaa agtcttaaca     420

gcaggaaccg gtcaagctct tggattgata cgtttaactg atgaatcctc aaataatccc     480
```

```
aatcaacaat ggaatttaac ttctgtacaa acaattcaac ttccacaaaa acctataata    540

gatacaaaat taaaagatta tcccaaatat tcaccaactg gaaatataga taatggaaca    600

tctcctcaat taatgggatg gacattagta ccttgtatta tggtaaatga tccaaatata    660

gataaaaata ctcaaattaa aactactcca tattatattt taaaaaaata tcaatattgg    720

caacgagcag taggaagtaa tgtagcttta cgtccacatg aaaaaaaatc atatacttat    780

gaatggggca cagaaataga tcaaaaaaca acaattataa atacattagg atttcaaatc    840

aatatagatt caggaatgaa atttgatata ccagaagtag gtggaggtac agatgaaata    900

aaaacacaac taaatgaaga attaaaaata gaatatagtc atgaaactaa aataatggaa    960

aaatatcaag aacaatctga aatagataat ccaactgatc aatcaatgaa ttctatagga   1020

tttcttacta ttacttcctt agaattatat agatataatg gctcagaaat tcgtataatg   1080

caaattcaaa cctcagataa tgatacttat aatgttactt cttatccaaa tcatcaacaa   1140

gctttattac ttcttacaaa tcattcatat gaagaagtag aagaaataac aaatattcct   1200

aaaagtacac taaaaaaatt aaaaaaatat tatttttaav v                       1241
```

```
<210> SEQ ID NO 43
<211> LENGTH: 383
<212> TYPE: PRT
<213> ORGANISM: Bacillus thuringiensis

<400> SEQUENCE: 43

Met Leu Asp Thr Asn Lys Val Tyr Glu Ile Ser Asn His Ala Asn Gly
1               5                   10                  15

Leu Tyr Ala Ala Thr Tyr Leu Ser Leu Asp Asp Ser Gly Val Ser Leu
            20                  25                  30

Met Asn Lys Asn Asp Asp Asp Ile Asp Asp Tyr Asn Leu Lys Trp Phe
        35                  40                  45

Leu Phe Pro Ile Asp Asp Asp Gln Tyr Ile Ile Thr Ser Tyr Ala Ala
    50                  55                  60

Asn Asn Cys Lys Val Trp Asn Val Asn Asn Asp Lys Ile Asn Val Ser
65                  70                  75                  80

Thr Tyr Ser Ser Thr Asn Ser Ile Gln Lys Trp Gln Ile Lys Ala Asn
                85                  90                  95

Gly Ser Ser Tyr Val Ile Gln Ser Asp Asn Gly Lys Val Leu Thr Ala
            100                 105                 110

Gly Thr Gly Gln Ala Leu Gly Leu Ile Arg Leu Thr Asp Glu Ser Ser
        115                 120                 125

Asn Asn Pro Asn Gln Gln Trp Asn Leu Thr Ser Val Gln Thr Ile Gln
    130                 135                 140

Leu Pro Gln Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Arg Ala Val Gly Ser Asn Val Ala Leu Arg Pro His
    210                 215                 220

Glu Lys Lys Ser Tyr Thr Tyr Glu Trp Gly Thr Glu Ile Asp Gln Lys
225                 230                 235                 240
```

-continued

```
Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser His Glu Thr Lys
        275                 280                 285

Ile Met Glu Lys Tyr Gln Glu Gln Ser Glu Ile Asp Asn Pro Thr Asp
    290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                325                 330                 335

Asp Asn Asp Thr Tyr Asn Val Thr Ser Tyr Pro Asn His Gln Gln Ala
            340                 345                 350

Leu Leu Leu Leu Thr Asn His Ser Tyr Glu Glu Val Glu Glu Ile Thr
        355                 360                 365

Asn Ile Pro Lys Ser Thr Leu Lys Lys Leu Lys Lys Tyr Tyr Phe
    370                 375                 380
```

```
<210> SEQ ID NO 44
<211> LENGTH: 360
<212> TYPE: DNA
<213> ORGANISM: Artificial Sequence
<220> FEATURE:
<223> OTHER INFORMATION: Maize-optimized gene sequence encoding the
      approximately 14 kDa toxin of 80JJ1

<400> SEQUENCE: 44

atgtccgccc gcgaggtgca catcgagatc aacaacaaga cccgccacac cctccagctc     60

gaggacaaga ccaagctctc cggcggcagg tggcgcacct ccccgaccaa cgtggcccgc    120

gacaccatca agacgttcgt ggcggagtcc cacggcttca tgaccggcgt cgagggcatc    180

atctacttct ccgtgaacgg cgacgccgag atctccctcc acttcgacaa cccgtacatc    240

ggctccaaca agtgcgacgg ctcctccgac aagcccgagt acgaggtgat cacccagtcc    300

ggctccggcg acaagtccca cgtgacctac accatccaga ccgtgtccct ccgcctctga    360
```

```
<210> SEQ ID NO 45
<211> LENGTH: 1158
<212> TYPE: DNA
<213> ORGANISM: Artificial Sequence
<220> FEATURE:
<223> OTHER INFORMATION: Maize-optimized gene sequence encoding the
      approximately 44 kDa toxin of 80JJ1

<400> SEQUENCE: 45

atgctcgaca ccaacaaggt gtacgagatc tccaacctcg ccaacggcct ctacacctcc     60

acctacctct ccctcgacga ctccggcgtg tccctcatgt ccaagaagga cgaggacatc    120

gacgactaca acctcaagtg gttcctcttc ccgatcgaca acaaccagta catcatcacc    180

tcctacggcg ccaacaactg caaggtgtgg aacgtgaaga acgacaagat caacgtgtcc    240

acctactcct ccaccaactc cgtgcagaag tggcagatca aggccaagga ctcctcctac    300

atcatccagt ccgacaacgg caaggtgctc accgcgggcg tgggccagtc cctcggcatc    360

gtgcgcctca ccgacgagtt cccggagaac tccaaccagc aatggaacct caccccggtg    420

cagaccatcc agctcccgca gaagccgaag atcgacgaga agctcaagga ccacccggag    480

tactccgaga ccggcaacat caacccgaag accacccccgc agctcatggg ctggaccctc    540
```

-continued

```
gtgccgtgca tcatggtgaa cgactccaag atcgacaaga acacccagat caagaccacc    600

ccgtactaca tcttcaagaa atacaagtac tggaacctcg ccaagggctc caacgtgtcc    660

ctcctcccgc accagaagcg cagctacgac tacgagtggg gcaccgagaa gaaccagaag    720

accaccatca tcaacaccgt gggcctgcag atcaacatcg actcggggat gaagttcgag    780

gtgccggagg tgggcggcgg caccgaggac atcaagaccc agctcaccga ggagctgaag    840

gtggagtact ccaccgagac caagatcatg accaagtacc aggagcactc cgagatcgac    900

aacccgacca accagccgat gaactccatc ggcctcctca tctacacctc cctcgagctg    960

taccgctaca acggcaccga gatcaagatc atggacatcg agacctccga ccacgacacc   1020

tacaccctca cctcctaccc gaaccacaag gaggcgctgc tgctgctgac caaccactcc   1080

tacgaggagg tggaggagat caccaagatc ccgaagcaca ccctcatcaa gctcaagaag   1140

cactacttca agaagtga                                                  1158
```

<210> SEQ ID NO 46
<211> LENGTH: 24
<212> TYPE: DNA
<213> ORGANISM: Artificial Sequence
<220> FEATURE:
<223> OTHER INFORMATION: DNA sequence of a reverse primer used in Example 15

<400> SEQUENCE: 46

```
gtagaagcag aacaagaagg tatt                                             24
```

<210> SEQ ID NO 47
<211> LENGTH: 25
<212> TYPE: DNA
<213> ORGANISM: Artificial Sequence
<220> FEATURE:
<223> OTHER INFORMATION: DNA sequence of a forward primer used in Example 16

<400> SEQUENCE: 47

```
atgtcagcwc gygaagtwca yattg                                            25
```

<210> SEQ ID NO 48
<211> LENGTH: 23
<212> TYPE: DNA
<213> ORGANISM: Artificial Sequence
<220> FEATURE:
<223> OTHER INFORMATION: DNA sequence of a reverse primer used in Example 16

<400> SEQUENCE: 48

```
gtytgaathg tatahgthac atg                                              23
```

<210> SEQ ID NO 49
<211> LENGTH: 25
<212> TYPE: DNA
<213> ORGANISM: Artificial Sequence
<220> FEATURE:
<223> OTHER INFORMATION: DNA sequence of a forward primer used in Example 16

<400> SEQUENCE: 49

```
atgttagata cwaataaart wtatg                                            25
```

<210> SEQ ID NO 50
<211> LENGTH: 29
<212> TYPE: DNA

<213> ORGANISM: Artificial Sequence
<220> FEATURE:
<223> OTHER INFORMATION: DNA sequence of a reverse primer used in Example 16

<400> SEQUENCE: 50
gtwatttctt cwacttcttc atahgaatg 29

<210> SEQ ID NO 51
<211> LENGTH: 341
<212> TYPE: DNA
<213> ORGANISM: Bacillus thuringiensis

<400> SEQUENCE: 51
atgtcaggtc gagaagtaca tattgaaata aacaataaaa cacgtcatac attacaatta 60
gaggataaaa ctaaacttag cggcggtaga tggcgaacat cacctacaaa tgttgctcgt 120
gatacaatta aaacatttgt agcagaatca catggtttta tgacaggagt agaaggtatt 180
atatatttta gtgtaaacgg agacgcagaa attagtttac attttgacaa tccttatata 240
ggttctaata aatgtgatgg ttcttctgat aaacctgaat atgaagttat tactcaaagc 300
ggatcaggag ataaatctca tgtaacatat actattcaga c 341

<210> SEQ ID NO 52
<211> LENGTH: 113
<212> TYPE: PRT
<213> ORGANISM: Bacillus thuringiensis

<400> SEQUENCE: 52

Met Ser Gly Arg Glu Val His Ile Glu Ile Asn Asn Lys Thr Arg His
1 5 10 15

Thr Leu Gln Leu Glu Asp Lys Thr Lys Leu Ser Gly Gly Arg Trp Arg
20 25 30

Thr Ser Pro Thr Asn Val Ala Arg Asp Thr Ile Lys Thr Phe Val Ala
35 40 45

Glu Ser His Gly Phe Met Thr Gly Val Glu Gly Ile Ile Tyr Phe Ser
50 55 60

Val Asn Gly Asp Ala Glu Ile Ser Leu His Phe Asp Asn Pro Tyr Ile
65 70 75 80

Gly Ser Asn Lys Cys Asp Gly Ser Ser Asp Lys Pro Glu Tyr Glu Val
85 90 95

Ile Thr Gln Ser Gly Ser Gly Asp Lys Ser His Val Thr Tyr Thr Ile
100 105 110

Gln

<210> SEQ ID NO 53
<211> LENGTH: 1103
<212> TYPE: DNA
<213> ORGANISM: Bacillus thuringiensis

<400> SEQUENCE: 53
atgttagata caaataaagt ttatgaaata agcaatcttg ctaatggatt atatacatcm 60
acttatttaa gtcttgatga ttcaggtgtt agtttaatga gtaaaaagga tgaagatatt 120
gatgattaca atttaaaatg gtttttattt cctattgata ataatcaata tattattaca 180
agctatggag ctaataattg taaagtttgg aatgttaaaa atgataaaat aaatgtttca 240
acttattctt caacaaactc tgtacaaaaa tggcaaataa aagctaaaga ttcttcatat 300 ataaatacaaa gtgataatgg aaaggtctta acagcaggag taggtcaatc tcttggaata 360

```
gtacgcctaa ctgatgaatt tccagagaat tctaaccaac aatggaattt aactcctgta    420

caaacaattc aactcccaca aaaacctaaa atagatgaaa aattaaaaga tcatcctgaa    480

tattcagaaa ccggaaatat aaatcctaaa acaactcctc aattaatggg atggacatta    540

gtaccttgta ttatggtaaa tgattcaaaa atagataaaa acactcaaat taaaactact    600

ccatattata tttttaaaaa atataaatac tggaatctag caaaaggaag taatgtatct    660

ttacttccac atcaaaaaag atcatatgat tatgaatggg gtacagaaaa aaatcaaaaa    720

acamctatta ttaatacagt aggattgcaa attaatatag actcaggaat gaaatttgaa    780

gtaccagaag taggaggagg tacagaagac ataaaaacac aattaactga agaattaaaa    840

gttgaatata gcactgaaac caaaataatg acgaaatatc aagaacactc agagatagat    900

aatccaacta atcaaccaat gaattctata ggacttctta tttacacttc tttagaatta    960

tatcgatata acggtacaga aattaagata atggacatag aaacttcaga tcatgatact   1020

tacactctta cttcttatcc aaatcataaa gaagcattat tacttctcac aaaccattca   1080

tatgaagaag tagaagaaat aac                                           1103


<210> SEQ ID NO 54
<211> LENGTH: 367
<212> TYPE: PRT
<213> ORGANISM: Bacillus thuringiensis
<220> FEATURE:
<221> NAME/KEY: Misc_feature
<222> LOCATION: (242)
<223> OTHER INFORMATION: Xaa may be any naturally-occurring amino acid

<400> SEQUENCE: 54

Met Leu Asp Thr Asn Lys Val Tyr Glu Ile Ser Asn Leu Ala Asn Gly
  1               5                  10                  15

Leu Tyr Thr Ser Thr Tyr Leu Ser Leu Asp Asp Ser Gly Val Ser Leu
             20                  25                  30

Met Ser Lys Lys Asp Glu Asp Ile Asp Asp Tyr Asn Leu Lys Trp Phe
         35                  40                  45

Leu Phe Pro Ile Asp Asn Asn Gln Tyr Ile Ile Thr Ser Tyr Gly Ala
     50                  55                  60

Asn Asn Cys Lys Val Trp Asn Val Lys Asn Asp Lys Ile Asn Val Ser
 65                  70                  75                  80

Thr Tyr Ser Ser Thr Asn Ser Val Gln Lys Trp Gln Ile Lys Ala Lys
                 85                  90                  95

Asp Ser Ser Tyr Ile Ile Gln Ser Asp Asn Gly Lys Val Leu Thr Ala
            100                 105                 110

Gly Val Gly Gln Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Lys Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
```

```
    210                 215                 220

Gln Lys Arg Ser Tyr Asp Tyr Glu Trp Gly Thr Glu Lys Asn Gln Lys
225                 230                 235                 240

Thr Xaa Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350

Leu Leu Leu Leu Thr Asn His Ser Tyr Glu Glu Val Glu Glu Ile
        355                 360                 365
```

<210> SEQ ID NO 55
<211> LENGTH: 341
<212> TYPE: DNA
<213> ORGANISM: Bacillus thuringiensis

<400> SEQUENCE: 55

```
atgtcagctc gtgaagtaca tattgatgta aataataaga caggtcatac attacaatta      60

gaagataaaa caaaacttga tggtggtaga tggcgaacat cacctacaaa tgttgctaat     120

gatcaaatta aaacatttgt agcagaatca catggtttta tgacaggtac agaaggtcat     180

atatattata gtataaatgg agaagcagaa attagtttat attttgataa tccttattca     240

ggttctaata aatatgatgg ggattccaat aaacctcaat atgaagttac tacccaagga     300

ggatcaggaa atcaatctca tgtaacatat acgattcaaa c                         341
```

<210> SEQ ID NO 56
<211> LENGTH: 113
<212> TYPE: PRT
<213> ORGANISM: Bacillus thuringiensis

<400> SEQUENCE: 56

```
Met Ser Ala Arg Glu Val His Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Phe Val Ala
         35                  40                  45

Glu Ser His Gly Phe Met Thr Gly Thr Glu Gly His Ile Tyr Tyr Ser
     50                  55                  60

Ile Asn Gly Glu Ala Glu Ile Ser Leu Tyr Phe Asp Asn Pro Tyr Ser
 65                  70                  75                  80

Gly Ser Asn Lys Tyr Asp Gly Asp Ser Asn Lys Pro Gln Tyr Glu Val
                 85                  90                  95

Thr Thr Gln Gly Gly Ser Gly Asn Gln Ser His Val Thr Tyr Thr Ile
            100                 105                 110

Gln
```

<210> SEQ ID NO 57
<211> LENGTH: 1103
<212> TYPE: DNA
<213> ORGANISM: Bacillus thuringiensis
<220> FEATURE:
<221> NAME/KEY: misc_feature
<222> LOCATION: (1028)
<223> OTHER INFORMATION: n is a, c, g or t

<400> SEQUENCE: 57

```
atgttagata ctaataaagt ttatgaaata agtaatcatg ctaatggact atatgcagca     60

acttatttaa gtttagatga ttcaggtgtt agtttaatga ataaaaatga tgatgatatt    120

gatgattaca acttaaaatg gtttttattt cctattgatg atgatcaata tattattaca    180

agctatgcag caaataattg taaagtttgg aatgttaata atgataaaat aaatgtttcg    240

acttattctt taacaaattc aatacaaaaa tggcaaataa aagctaatgg ttcttcatat    300

gtaatacaaa gtgataatgg aaaagtctta acagcaggaa ccggtcaagc tcttggattg    360

atacgtttaa ctgatgaatc ttcaaataat cccaatcaac aatggaattt aacttctgta    420

caaacaattc aacttccaca aaaacctata atagatacaa aattaaaaga ttatcccaaa    480

tattcaccaa ctggaaatat agataatgga acatctcctc aattaatggg atggacatta    540

gtaccttgta ttatggtaaa tgatccaaat atagataaaa atactcaaat taaaactact    600

ccatattata ttttaaaaaa atatcaatat tggcaacgag cagtaggaag taatgtagct    660

ttacgtccac atgaaaaaaa atcatatact tatgaatggg gaacagaaat agatcaaaaa    720

acaacaatca taaatacatt aggatttcaa atcaatatag attcaggaat gaaatttgat    780

ataccagaag taggtggagg tacagatgaa ataaaaacac aactaaatga agaattaaaa    840

atagaatata gtcgtgaaac taaaataatg gaaaaatatc aagaacaatc tgaaatagat    900

aatccaactg atcaaccaat gaattctata ggatttctta ctattacttc tttagaatta    960

tatagatata atggctcaga aattcgtata atgcaaattc aaacctcaga taatgatact   1020

tataatgnta cttcttatcc agatcatcaa caagctttat tacttcttac aaatcattca   1080

tatgaagaac tagaagaaat aac                                            1103
```

<210> SEQ ID NO 58
<211> LENGTH: 367
<212> TYPE: PRT
<213> ORGANISM: Bacillus thuringiensis
<220> FEATURE:
<221> NAME/KEY: Misc_feature
<222> LOCATION: (343)
<223> OTHER INFORMATION: Xaa may be any naturally-occurring amino acid

<400> SEQUENCE: 58

```
Met Leu Asp Thr Asn Lys Val Tyr Glu Ile Ser Asn His Ala Asn Gly
  1               5                  10                  15

Leu Tyr Ala Ala Thr Tyr Leu Ser Leu Asp Asp Ser Gly Val Ser Leu
             20                  25                  30

Met Asn Lys Asn Asp Asp Asp Ile Asp Asp Tyr Asn Leu Lys Trp Phe
         35                  40                  45

Leu Phe Pro Ile Asp Asp Asp Gln Tyr Ile Ile Thr Ser Tyr Ala Ala
     50                  55                  60

Asn Asn Cys Lys Val Trp Asn Val Asn Asn Asp Lys Ile Asn Val Ser
 65                  70                  75                  80

Thr Tyr Ser Leu Thr Asn Ser Ile Gln Lys Trp Gln Ile Lys Ala Asn
```

-continued

```
                85                  90                  95

Gly Ser Ser Tyr Val Ile Gln Ser Asp Asn Gly Lys Val Leu Thr Ala
            100                 105                 110

Gly Thr Gly Gln Ala Leu Gly Leu Ile Arg Leu Thr Asp Glu Ser Ser
        115                 120                 125

Asn Asn Pro Asn Gln Gln Trp Asn Leu Thr Ser Val Gln Thr Ile Gln
    130                 135                 140

Leu Pro Gln Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Arg Ala Val Gly Ser Asn Val Ala Leu Arg Pro His
    210                 215                 220

Glu Lys Lys Ser Tyr Thr Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser Arg Glu Thr Lys
        275                 280                 285

Ile Met Glu Lys Tyr Gln Glu Gln Ser Glu Ile Asp Asn Pro Thr Asp
    290                 295                 300

Gln Pro Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                325                 330                 335

Asp Asn Asp Thr Tyr Asn Xaa Thr Ser Tyr Pro Asp His Gln Gln Ala
            340                 345                 350

Leu Leu Leu Leu Thr Asn His Ser Tyr Glu Glu Leu Glu Glu Ile
        355                 360                 365
```

<210> SEQ ID NO 59
<211> LENGTH: 340
<212> TYPE: DNA
<213> ORGANISM: Bacillus thuringiensis

<400> SEQUENCE: 59

```
atgtcagcag gtgaagtaca tattgatgca aataataaga caggtcatac attacaatta     60

gaagataaaa caaaacttga tggtggtaga tggcgaacat cacctacaaa tgttgctaat    120

gatcaaatta aaacatttgt agcagaatca catggtttta tgacaggtac agaaggtcat    180

atatattata gtataaatgg agaagcagaa attagtttat attttgataa tccttattca    240

ggttctaata aatatgatgg ggattccaat aaacctcaat atgaagttac tacccaagga    300

ggatcaggaa atcaatctca tgttacttat acaattcaaa                          340
```

<210> SEQ ID NO 60
<211> LENGTH: 113
<212> TYPE: PRT
<213> ORGANISM: Bacillus thuringiensis

```
<400> SEQUENCE: 60

Met Ser Ala Gly Glu Val His Ile Asp Ala Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Phe Val Ala
         35                  40                  45

Glu Ser His Gly Phe Met Thr Gly Thr Glu Gly His Ile Tyr Tyr Ser
     50                  55                  60

Ile Asn Gly Glu Ala Glu Ile Ser Leu Tyr Phe Asp Asn Pro Tyr Ser
 65                  70                  75                  80

Gly Ser Asn Lys Tyr Asp Gly Asp Ser Asn Lys Pro Gln Tyr Glu Val
                 85                  90                  95

Thr Thr Gln Gly Gly Ser Gly Asn Gln Ser His Val Thr Tyr Thr Ile
            100                 105                 110

Gln


<210> SEQ ID NO 61
<211> LENGTH: 340
<212> TYPE: DNA
<213> ORGANISM: Bacillus thuringiensis

<400> SEQUENCE: 61

tgtcagcacg tgaagtacat attgaaataa acaataaaac acgtcataca ttacaattag     60

aggataaaac taaacttagc ggcggtagat ggcgaacatc acctacaaat gttgctcgtg    120

atacaattaa aacatttgta gcagaatcac atggttttat gacaggagta gaaggtatta    180

tatattttag tgtaaacgga gacgcagaaa ttagtttaca ttttgacaat ccttatatag    240

gttctaataa atgtgatggt tcttctgata aacctgaata tgaagttatt actcaaagcg    300

gatcaggaga taaatctcat gtgacatata cgattcagac                          340


<210> SEQ ID NO 62
<211> LENGTH: 112
<212> TYPE: PRT
<213> ORGANISM: Bacillus thuringiensis

<400> SEQUENCE: 62

Ser Ala Arg Glu Val His Ile Glu Ile Asn Asn Lys Thr Arg His Thr
  1               5                  10                  15

Leu Gln Leu Glu Asp Lys Thr Lys Leu Ser Gly Gly Arg Trp Arg Thr
             20                  25                  30

Ser Pro Thr Asn Val Ala Arg Asp Thr Ile Lys Thr Phe Val Ala Glu
         35                  40                  45

Ser His Gly Phe Met Thr Gly Val Glu Gly Ile Ile Tyr Phe Ser Val
     50                  55                  60

Asn Gly Asp Ala Glu Ile Ser Leu His Phe Asp Asn Pro Tyr Ile Gly
 65                  70                  75                  80

Ser Asn Lys Cys Asp Gly Ser Ser Asp Lys Pro Glu Tyr Glu Val Ile
                 85                  90                  95

Thr Gln Ser Gly Ser Gly Asp Lys Ser His Val Thr Tyr Thr Ile Gln
            100                 105                 110


<210> SEQ ID NO 63
<211> LENGTH: 1114
<212> TYPE: DNA
<213> ORGANISM: Bacillus thuringiensis
```

<400> SEQUENCE: 63

```
atgttagata ctaataaaat ttatgaaata agcaatcttg ctaatggatt atatacatca      60
acttatttaa gtcttgatga ttcaggtgtt agtttaatga gtaaaaagga tgaagatatt     120
gatgattaca atttaaaatg gtttttattt cctattgata ataatcaata tattattaca     180
agctatggag ctaataattg taaagtttgg aatgttaaaa atgataaaat aaatgtttca     240
acttattctt caacaaactc tgtacaaaaa tggcaaataa aagctaaaga ttcttcatat     300
ataatacaaa gtgataatgg aaaggtctta acagcaggag taggtcaatc tcttggaata     360
gtacgcctaa ctgatgaatt tccagagaat tctaaccaac aatggaattt aactcctgta     420
caaacaattc aactcccaca aaaacctaaa atagatgaaa aattaaaaga tcatcctgaa     480
tattcagaaa ccggaaatat aaatcctaaa acaactcctc aattaatggg atggacatta     540
gtaccttgta ttatggtaaa tgattcaaaa atagataaaa acactcaaat taaaactact     600
ccatattata tttttaaaaa atataaatac tggaatctag caaaaggaag taatgtatct     660
ttacttccac atcaaaaaag atcatatgat tatgaatggg gtacagaaaa aaatcaaaaa     720
acaactatta ttaatacagt aggattgcaa attaatatag attcaggaat gaaatttgaa     780
gtaccagaag taggaggagg tacagaagac ataaaaacac aattaactga agaattaaaa     840
gttgaatata gcactgaaac caaaataatg acgaaatatc aagaacactc agagatagat     900
aatccaacta atcaaccaat gaattctata ggacttctta tttatacttc tttagaatta     960
tatcgatata acggtacaga aattaagata atggacatag aaacttcaga tcatgatact    1020
tacactctta cttcttatcc aaatcataaa gaagcattat tacttctcac aaaccattct    1080
tatgaagaac tagaacaaat tacaagggcg aatt                                1114
```

<210> SEQ ID NO 64
<211> LENGTH: 371
<212> TYPE: PRT
<213> ORGANISM: Bacillus thuringiensis

<400> SEQUENCE: 64

```
Met Leu Asp Thr Asn Lys Ile Tyr Glu Ile Ser Asn Leu Ala Asn Gly
  1               5                  10                  15

Leu Tyr Thr Ser Thr Tyr Leu Ser Leu Asp Asp Ser Gly Val Ser Leu
             20                  25                  30

Met Ser Lys Lys Asp Glu Asp Ile Asp Asp Tyr Asn Leu Lys Trp Phe
         35                  40                  45

Leu Phe Pro Ile Asp Asn Asn Gln Tyr Ile Ile Thr Ser Tyr Gly Ala
     50                  55                  60

Asn Asn Cys Lys Val Trp Asn Val Lys Asn Asp Lys Ile Asn Val Ser
 65                  70                  75                  80

Thr Tyr Ser Ser Thr Asn Ser Val Gln Lys Trp Gln Ile Lys Ala Lys
                 85                  90                  95

Asp Ser Ser Tyr Ile Ile Gln Ser Asp Asn Gly Lys Val Leu Thr Ala
            100                 105                 110

Gly Val Gly Gln Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160
```

-continued

```
Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Lys Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Thr Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350

Leu Leu Leu Leu Thr Asn His Ser Tyr Glu Glu Leu Glu Gln Ile Thr
        355                 360                 365

Arg Ala Asn
    370
```

<210> SEQ ID NO 65
<211> LENGTH: 360
<212> TYPE: DNA
<213> ORGANISM: Bacillus thuringiensis

<400> SEQUENCE: 65

```
atgtcagctc gcgaagtaca cattgaaata aacaataaaa cacgtcatac attacaatta      60

gaggataaaa ctaaacttag cggcggtaga tggcgaacat cacctacaaa tgttgctcgt     120

gatacaatta aaacatttgt agcagaatca catggtttta tgacaggagt agaaggtatt     180

atatatttta gtgtaaacgg agacgcagaa attagtttac attttgacaa tccttatata     240

ggttctaata aatgtgatgg ttcttctgat aaacctgaat atgaagttat tactcaaagc     300

ggatcaggag ataaatctca tgtgacatat actattcaga cagtatcttt acgattataa     360
```

<210> SEQ ID NO 66
<211> LENGTH: 119
<212> TYPE: PRT
<213> ORGANISM: Bacillus thuringiensis

<400> SEQUENCE: 66

```
Met Ser Ala Arg Glu Val His Ile Glu Ile Asn Asn Lys Thr Arg His
  1               5                  10                  15

Thr Leu Gln Leu Glu Asp Lys Thr Lys Leu Ser Gly Gly Arg Trp Arg
             20                  25                  30

Thr Ser Pro Thr Asn Val Ala Arg Asp Thr Ile Lys Thr Phe Val Ala
         35                  40                  45
```

```
Glu Ser His Gly Phe Met Thr Gly Val Glu Gly Ile Ile Tyr Phe Ser
     50                  55                  60

Val Asn Gly Asp Ala Glu Ile Ser Leu His Phe Asp Asn Pro Tyr Ile
 65                  70                  75                  80

Gly Ser Asn Lys Cys Asp Gly Ser Ser Asp Lys Pro Glu Tyr Glu Val
                 85                  90                  95

Ile Thr Gln Ser Gly Ser Gly Asp Lys Ser His Val Thr Tyr Thr Ile
            100                 105                 110

Gln Thr Val Ser Leu Arg Leu
        115
```

<210> SEQ ID NO 67
<211> LENGTH: 1158
<212> TYPE: DNA
<213> ORGANISM: Bacillus thuringiensis

<400> SEQUENCE: 67

```
atgttagata ctaataaagt ttatgaaata agcaatcttg ctaatggatt atatacatca      60

acttatttaa gtcttgatga ttcaggtgtt agtttaatga gtaaaaagga tgaagatatt     120

gatgattaca atttaaaatg gtttttattt cctattgata ataatcaata tattattaca     180

agctatggag ctaataattg taaagtttgg aatgttaaaa atgataaaat aaatgtttca     240

acttattctt caacaaactc tgtacaaaaa tggcaaataa aagctaaaga ttcttcatat     300

ataatacaaa gtgataatgg aaaggtctta acagcaggag taggtcaatc tcttggaata     360

gtacgcctaa ctgatgaatt tccagagaat tctaaccaac aatggaattt aactcctgta     420

caaacaattc aactcccaca aaaacctaaa atagatgaaa aattaaaaga tcatcctgaa     480

tattcagaaa ccggaaatat aaatcctaaa acaactcctc aattaatggg atggacatta     540

gtaccttgta ttatggtaaa tgattcaaaa atagataaaa acactcaaat taaaactact     600

ccatattata tttttaaaaa atataaatac tggaatctag caaaaggaag taatgtatct     660

ttacttccac atcaaaaaag atcatatgat tatgaatggg gtacagaaaa aaatcaaaaa     720

acaactatta ttaatacagt aggattgcaa attaatatag attcaggaat gaaatttgaa     780

gtaccagaag taggaggagg tacagaagac ataaaaacac aattaactga agaattaaaa     840

gttgaatata gcactgaaac caaaataatg acgaaatatc aagaacactc agagatagat     900

aatccaacta atcaaccaat gaattctata ggacttctta tttatacttc tttagaatta     960

tatcgatata acggtacaga aattaagata atggacatag aaacttcaga tcatgatact    1020

tacactctta cttcttatcc aaatcataaa gaagcattat tacttctcac aaaccattcg    1080

tatgaagaag tagaagaaat aacaaaaata cctaagcata cacttataaa attgaaaaaa    1140

cattatttta aaaaataa                                                  1158
```

<210> SEQ ID NO 68
<211> LENGTH: 385
<212> TYPE: PRT
<213> ORGANISM: Bacillus thuringiensis
<220> FEATURE:
<223> OTHER INFORMATION: Description of Unknown Organism:protein

<400> SEQUENCE: 68

```
Met Leu Asp Thr Asn Lys Val Tyr Glu Ile Ser Asn Leu Ala Asn Gly
  1               5                  10                  15

Leu Tyr Thr Ser Thr Tyr Leu Ser Leu Asp Asp Ser Gly Val Ser Leu
             20                  25                  30
```

-continued

```
Met Ser Lys Lys Asp Glu Asp Ile Asp Asp Tyr Asn Leu Lys Trp Phe
        35                  40                  45

Leu Phe Pro Ile Asp Asn Asn Gln Tyr Ile Ile Thr Ser Tyr Gly Ala
    50                  55                  60

Asn Asn Cys Lys Val Trp Asn Val Lys Asn Asp Lys Ile Asn Val Ser
65                  70                  75                  80

Thr Tyr Ser Ser Thr Asn Ser Val Gln Lys Trp Gln Ile Lys Ala Lys
                85                  90                  95

Asp Ser Ser Tyr Ile Ile Gln Ser Asp Asn Gly Lys Val Leu Thr Ala
            100                 105                 110

Gly Val Gly Gln Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Lys Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Thr Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350

Leu Leu Leu Leu Thr Asn His Ser Tyr Glu Glu Val Glu Glu Ile Thr
        355                 360                 365

Lys Ile Pro Lys His Thr Leu Ile Lys Leu Lys Lys His Tyr Phe Lys
    370                 375                 380

Lys
385
```

```
<210> SEQ ID NO 69
<211> LENGTH: 341
<212> TYPE: DNA
<213> ORGANISM: Bacillus thuringiensis

<400> SEQUENCE: 69

atgtcagcac gagaagtaca cattgatgta aataataaga caggtcatac attacaatta     60
```

-continued

```
gaagataaaa caaaacttga tggtggtaga tggcgaacat cacctacaaa tgttgctaat    120

gatcaaatta aaacatctgt agcagaatca aatggtttta tgacaggtac agaaggtact    180

atatattata gtataaatgg agaagcagaa attagtttat attttgacaa tccttttgca    240

ggttctaata aatatgatgg acattccaat aaatctcaat atgaaattat tacccaagga    300

ggatcaggaa atcaatctca tgttacttat acaattcaga c                        341
```

```
<210> SEQ ID NO 70
<211> LENGTH: 113
<212> TYPE: PRT
<213> ORGANISM: Bacillus thuringiensis

<400> SEQUENCE: 70

Met Ser Ala Arg Glu Val His Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Ser Val Ala
         35                  40                  45

Glu Ser Asn Gly Phe Met Thr Gly Thr Glu Gly Thr Ile Tyr Tyr Ser
     50                  55                  60

Ile Asn Gly Glu Ala Glu Ile Ser Leu Tyr Phe Asp Asn Pro Phe Ala
 65                  70                  75                  80

Gly Ser Asn Lys Tyr Asp Gly His Ser Asn Lys Ser Gln Tyr Glu Ile
                 85                  90                  95

Ile Thr Gln Gly Gly Ser Gly Asn Gln Ser His Val Thr Tyr Thr Ile
            100                 105                 110

Gln
```

```
<210> SEQ ID NO 71
<211> LENGTH: 340
<212> TYPE: DNA
<213> ORGANISM: Bacillus thuringiensis

<400> SEQUENCE: 71

atgtcagcag gcgaagttca tattgatgta aataataaga caggtcatac attacaatta     60

gaagataaaa caaaacttga tggtggtaga tggcgaacat cacctacaaa tgttgctaat    120

gatcaaatta aaacatttgt agcagaatca aatggtttta tgacaggtac agaaggtact    180

atatattata gtataaatgg agaagcagaa attagtttat attttgacaa tccttttgca    240

ggttctaata aatatgatgg acattccaat aaatctcaat atgaaattat tacccaagga    300

ggatcaggaa atcaatctca tgtaacgtat acaattcaaa                          340
```

```
<210> SEQ ID NO 72
<211> LENGTH: 113
<212> TYPE: PRT
<213> ORGANISM: Bacillus thuringiensis

<400> SEQUENCE: 72

Met Ser Ala Gly Glu Val His Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Phe Val Ala
         35                  40                  45

Glu Ser Asn Gly Phe Met Thr Gly Thr Glu Gly Thr Ile Tyr Tyr Ser
```

-continued

```
     50                  55                  60

Ile Asn Gly Glu Ala Glu Ile Ser Leu Tyr Phe Asp Asn Pro Phe Ala
 65                  70                  75                  80

Gly Ser Asn Lys Tyr Asp Gly His Ser Asn Lys Ser Gln Tyr Glu Ile
                 85                  90                  95

Ile Thr Gln Gly Gly Ser Gly Asn Gln Ser His Val Thr Tyr Thr Ile
            100                 105                 110

Gln


<210> SEQ ID NO 73
<211> LENGTH: 340
<212> TYPE: DNA
<213> ORGANISM: Bacillus thuringiensis

<400> SEQUENCE: 73

atgtcagctc gcgaagtwca tattgaaata aacaataaaa cacgtcatac attacaatta      60

gaggataaaa ctaaacttag cggcggtaga tggcgaacat cacctacaaa tgttgctcgt     120

gatacaatta aaacatttgt agcagaatca catggtttta tgacaggagt agaaggtatt     180

atatatttta gtgtaaacgg agacgcagaa attagtttac attttgacaa tccttatata     240

ggttctaata aatgtgatgg ttcttctgat aaacctgaat atgaagttat tactcaaagc     300

ggatcaggag ataaatctca tgtgacatat accattcaaa                           340


<210> SEQ ID NO 74
<211> LENGTH: 113
<212> TYPE: PRT
<213> ORGANISM: Bacillus thuringiensis

<400> SEQUENCE: 74

Met Ser Ala Arg Glu Val His Ile Glu Ile Asn Asn Lys Thr Arg His
  1               5                  10                  15

Thr Leu Gln Leu Glu Asp Lys Thr Lys Leu Ser Gly Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Val Glu Gly Ile Ile Tyr Phe Ser
     50                  55                  60

Val Asn Gly Asp Ala Glu Ile Ser Leu His Phe Asp Asn Pro Tyr Ile
 65                  70                  75                  80

Gly Ser Asn Lys Cys Asp Gly Ser Ser Asp Lys Pro Glu Tyr Glu Val
                 85                  90                  95

Ile Thr Gln Ser Gly Ser Gly Asp Lys Ser His Val Thr Tyr Thr Ile
            100                 105                 110

Gln


<210> SEQ ID NO 75
<211> LENGTH: 341
<212> TYPE: DNA
<213> ORGANISM: Bacillus thuringiensis

<400> SEQUENCE: 75

atgtcagctc gcgaagttca tattgaaata aataataaaa cacgtcatac attacaatta      60

gaggataaaa ctaaacttac cagtggtaga tggcgaacat cacctacaaa tgttgctcgt     120

gatacaatta aaacatttgt agcagaatca catggtttta tgacaggaat agaaggtatt     180

atatatttta gcgtaaacgg agaagcagaa attagtttac attttgacaa tccttatgta     240
```

```
ggttctaata aatatgatgg ttcttctgat aaagctgcat acgaagttat tgctcaaggt    300

ggatcagggg atatatctca tgtaacttat acaattcaaa c                        341


<210> SEQ ID NO 76
<211> LENGTH: 113
<212> TYPE: PRT
<213> ORGANISM: Bacillus thuringiensis

<400> SEQUENCE: 76

Met Ser Ala Arg Glu Val His Ile Glu Ile Asn Asn Lys Thr Arg His
  1               5                  10                  15

Thr Leu Gln Leu Glu Asp Lys Thr Lys Leu Thr Ser Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Ile Glu Gly Ile Ile Tyr Phe Ser
     50                  55                  60

Val Asn Gly Glu Ala Glu Ile Ser Leu His Phe Asp Asn Pro Tyr Val
 65                  70                  75                  80

Gly Ser Asn Lys Tyr Asp Gly Ser Ser Asp Lys Ala Ala Tyr Glu Val
                 85                  90                  95

Ile Ala Gln Gly Gly Ser Gly Asp Ile Ser His Val Thr Tyr Thr Ile
            100                 105                 110

Gln


<210> SEQ ID NO 77
<211> LENGTH: 1175
<212> TYPE: DNA
<213> ORGANISM: Bacillus thuringiensis

<400> SEQUENCE: 77

atgttagata ctaataaagt ttatgaaata agcaatcatg ctaatggatt atatacatca     60

acttatttaa gtctggatga ttcaggtgtt agtttaatgg gtcaaaatga tgaggatata    120

gatgaatmca atttaaagtg gttcttattt ccaatagata ataatcaata tattattaca    180

agctatggag cgaataattg taaagtttgg aatgttaaaa atgataaagt aaatgtttca    240

acgtattctc caacaaactc agtacaaaaa tggcaaataa aagctaaaaa ttcttcatat    300

ataatacaaa gtgagaatgg aaaagtctta acagcaggaa taggtcaatc tcctggaata    360

gtacgcttaa ccgatgaatc atcagagagt tctaaccaac aatggaattt aatccctgta    420

caaacaattt cactcccaca aaaacctaaa atagataaaa aattaaaaga tcatcctgaa    480

tattcagaaa ccggaaatat agctactgga acaattcctc aattaatggg atggacatta    540

gtaccttgta ttatggtaaa tgatccaaaa atagataaaa acactcaaat taaaactact    600

ccatattata tttttaaaaa atatcaatac tggaaacgag caataggaag taatgtatct    660

ttacttccac atcaaaaaaa atcatatgat tatgagtggg gtacagaaga aaatcaaaaa    720

acaactatta ttaatacagt aggatttcaa attaatgtag attcaggaat gaagtttgag    780

gtaccagaag taggaggagg tacagaagaa ataaaaacac aattaaatga agaattaaaa    840

gttgaatata gcactgacac caaaataatg aaaaaatatc aagaacactc agagatagat    900

aatccaacta atcaaacaat gaattctata ggatttctta cttttacttc tttagaatta    960

tatcgatata acggttcgga aattcgtata atgagaatgg aaacttcaga taatgatact   1020

tatactctga cctcttatcc aaatcataga gaagcattat tacttctcac aaatcattca   1080
```

```
tatcaagaag tacmagaaat tacaagggcg aattcttgca gatatccatc acactggcgg   1140

gccggtcgag ccttgcatct agaggggccc caatt                              1175


<210> SEQ ID NO 78
<211> LENGTH: 391
<212> TYPE: PRT
<213> ORGANISM: Bacillus thuringiensis
<220> FEATURE:
<221> NAME/KEY: MISC_FEATURE
<222> LOCATION: (43)
<223> OTHER INFORMATION: Xaa may be any naturally-occurring amino acid
<220> FEATURE:
<221> NAME/KEY: MISC_FEATURE
<222> LOCATION: (365)
<223> OTHER INFORMATION: Xaa may be any naturally-occurring amino acid

<400> SEQUENCE: 78

Met Leu Asp Thr Asn Lys Val Tyr Glu Ile Ser Asn His Ala Asn Gly
  1               5                  10                  15

Leu Tyr Thr Ser Thr Tyr Leu Ser Leu Asp Asp Ser Gly Val Ser Leu
             20                  25                  30

Met Gly Gln Asn Asp Glu Asp Ile Asp Glu Xaa Asn Leu Lys Trp Phe
         35                  40                  45

Leu Phe Pro Ile Asp Asn Asn Gln Tyr Ile Ile Thr Ser Tyr Gly Ala
     50                  55                  60

Asn Asn Cys Lys Val Trp Asn Val Lys Asn Asp Lys Val Asn Val Ser
 65                  70                  75                  80

Thr Tyr Ser Pro Thr Asn Ser Val Gln Lys Trp Gln Ile Lys Ala Lys
                 85                  90                  95

Asn Ser Ser Tyr Ile Ile Gln Ser Glu Asn Gly Lys Val Leu Thr Ala
            100                 105                 110

Gly Ile Gly Gln Ser Pro Gly Ile Val Arg Leu Thr Asp Glu Ser Ser
        115                 120                 125

Glu Ser Ser Asn Gln Gln Trp Asn Leu Ile Pro Val Gln Thr Ile Ser
    130                 135                 140

Leu Pro Gln Lys Pro Lys Ile Asp Lys Lys Leu Lys Asp His Pro Glu
145                 150                 155                 160

Tyr Ser Glu Thr Gly Asn Ile Ala Thr Gly Thr Ile Pro Gln Leu Met
                165                 170                 175

Gly Trp Thr Leu Val Pro Cys Ile Met Val Asn Asp Pro Lys Ile Asp
            180                 185                 190

Lys Asn Thr Gln Ile Lys Thr Thr Pro Tyr Tyr Ile Phe Lys Lys Tyr
        195                 200                 205

Gln Tyr Trp Lys Arg Ala Ile Gly Ser Asn Val Ser Leu Leu Pro His
    210                 215                 220

Gln Lys Lys Ser Tyr Asp Tyr Glu Trp Gly Thr Glu Glu Asn Gln Lys
225                 230                 235                 240

Thr Thr Ile Ile Asn Thr Val Gly Phe Gln Ile Asn Val Asp Ser Gly
                245                 250                 255

Met Lys Phe Glu Val Pro Glu Val Gly Gly Gly Thr Glu Glu Ile Lys
            260                 265                 270

Thr Gln Leu Asn Glu Glu Leu Lys Val Glu Tyr Ser Thr Asp Thr Lys
        275                 280                 285

Ile Met Lys Lys Tyr Gln Glu His Ser Glu Ile Asp Asn Pro Thr Asn
    290                 295                 300

Gln Thr Met Asn Ser Ile Gly Phe Leu Thr Phe Thr Ser Leu Glu Leu
```

-continued

```
305                 310                 315                 320

Tyr Arg Tyr Asn Gly Ser Glu Ile Arg Ile Met Arg Met Glu Thr Ser
                325                 330                 335

Asp Asn Asp Thr Tyr Thr Leu Thr Ser Tyr Pro Asn His Arg Glu Ala
            340                 345                 350

Leu Leu Leu Leu Thr Asn His Ser Tyr Gln Glu Val Xaa Glu Ile Thr
        355                 360                 365

Arg Ala Asn Ser Cys Arg Tyr Pro Ser His Trp Arg Ala Gly Arg Ala
    370                 375                 380

Leu His Leu Glu Gly Pro Gln
385                 390
```

<210> SEQ ID NO 79
<211> LENGTH: 341
<212> TYPE: DNA
<213> ORGANISM: Bacillus thuringiensis

<400> SEQUENCE: 79

```
atgtcagcag gtgaagttca tattgaaata aataataaaa cacgtcatac attacaatta     60

gaggataaaa ctaaacttac cagtggtaga tggcgaacat cacctacaaa tgttgctcgt    120

gatacaatta aaacatttgt agcagaatca catggtttta tgacaggaat agaaggtatt    180

atatatttta gcgtaaacgg agaagcagaa attagtttac attttgacaa tccttatgta    240

ggttctaata aatatgatgg ttcttctgat aaagctgcat acgaagttat tgctcaaggt    300

ggatcagggg atatatctca tctaacatat acaattcaaa c                        341
```

<210> SEQ ID NO 80
<211> LENGTH: 113
<212> TYPE: PRT
<213> ORGANISM: Bacillus thuringiensis

<400> SEQUENCE: 80

```
Met Ser Ala Gly Glu Val His Ile Glu Ile Asn Asn Lys Thr Arg His
  1               5                  10                  15

Thr Leu Gln Leu Glu Asp Lys Thr Lys Leu Thr Ser Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Ile Glu Gly Ile Ile Tyr Phe Ser
     50                  55                  60

Val Asn Gly Glu Ala Glu Ile Ser Leu His Phe Asp Asn Pro Tyr Val
 65                  70                  75                  80

Gly Ser Asn Lys Tyr Asp Gly Ser Ser Asp Lys Ala Ala Tyr Glu Val
                 85                  90                  95

Ile Ala Gln Gly Gly Ser Gly Asp Ile Ser His Leu Thr Tyr Thr Ile
            100                 105                 110

Gln
```

<210> SEQ ID NO 81
<211> LENGTH: 1410
<212> TYPE: DNA
<213> ORGANISM: Bacillus thuringiensis

<400> SEQUENCE: 81

```
atgttagata ctaataaaat ttatgaaata agcaatcatg ctaatggatt atatacatca     60

acttatttaa gtctggatga ttcaggtgtt agtttaatgg gtcaaaatga tgaggatata    120
```

```
gatgaataca atttaaagtg gttcttattt ccaatagata ataatcaata tattattaca    180

agctatggag cgaataattg taaagtttgg aatgttaaaa atgataaagt aaatgtttca    240

acgtattctc caacaaactc agtacaaaaa tggcaaataa aagctaaaaa ttcttcatat    300

ataatacaaa gtgagaatgg aaaagtctta acagcaggaa taggtcaatc tcttggaata    360

gtacgcttaa ccgatgaatc atcagagagt tctaaccaac aatggaattt aatccctgta    420

caaacaattt cactcccaca aaaacctaaa atagataaaa aattaaaaga tcatcctgaa    480

tattcagaaa ccggaaatat agctactgga acaattcctc aattaatggg atggacatta    540

gtaccttgta ttatggtaaa tgatccaaaa ataggtaaaa acactcaaat taaaactact    600

ccatattata tttttaaaaa atatcaatac tggaaacgag caataggaag taatgtatct    660

ttacttccac atcaaaaaaa atcatatgat tatgagtggg gtacagaaga aaatcaaaaa    720

acaactatta ttaatacagt aggatttcaa attaatgtag attcaggaat gaagtttgag    780

gtaccagaag taggaggagg tacagaagaa ataaaaacac aattaaatga agaattaaaa    840

gttgaatata gcactgacac caaaataatg aaaaaatatc aagaacactc agagatagat    900

aatccaacta atcaaacaac gaattctata ggatttctta cttttacttc tttagaatta    960

tatcgatata acggttcgga aattcgtata atgagaatgg aaacttcaga taatgatact   1020

tatactctga cctcttatcc aaatcataga gaagcattat tacttctcac aaatcattct   1080

tatcaagaag taagccgaat tccagcacac tggcggccgt tactagtgga tccgagctcg   1140

gtaccaagct tggcgtaatc atggtcatag stgtttcctg tgtgaaattg ttatccgctc   1200

acaattccac acaacatacg agccggaagc ataaagtgta aagcctgggg tgcctaatga   1260

gtgagctaac tcacattaat tgcgttgcgc tcactgcccg ctttccagtc gggaaacctg   1320

tcgtgccagc tgcattaatg aatcggccaa cgcgcgggga gaggcggttt gcgtattggg   1380

cgctcttccg cttcctcgct cactgactcg                                    1410
```

<210> SEQ ID NO 82
<211> LENGTH: 462
<212> TYPE: PRT
<213> ORGANISM: Bacillus thuringiensis
<220> FEATURE:
<221> NAME/KEY: MISC_FEATURE
<222> LOCATION: (389)
<223> OTHER INFORMATION: Xaa may be any naturally-occurring amino acid

<400> SEQUENCE: 82

```
Met Leu Asp Thr Asn Lys Ile Tyr Glu Ile Ser Asn His Ala Asn Gly
  1               5                  10                  15

Leu Tyr Thr Ser Thr Tyr Leu Ser Leu Asp Asp Ser Gly Val Ser Leu
             20                  25                  30

Met Gly Gln Asn Asp Glu Asp Ile Asp Glu Tyr Asn Leu Lys Trp Phe
         35                  40                  45

Leu Phe Pro Ile Asp Asn Asn Gln Tyr Ile Ile Thr Ser Tyr Gly Ala
     50                  55                  60

Asn Asn Cys Lys Val Trp Asn Val Lys Asn Asp Lys Val Asn Val Ser
 65                  70                  75                  80

Thr Tyr Ser Pro Thr Asn Ser Val Gln Lys Trp Gln Ile Lys Ala Lys
                 85                  90                  95

Asn Ser Ser Tyr Ile Ile Gln Ser Glu Asn Gly Lys Val Leu Thr Ala
            100                 105                 110

Gly Ile Gly Gln Ser Leu Gly Ile Val Arg Leu Thr Asp Glu Ser Ser
```

```
        115                 120                 125

Glu Ser Ser Asn Gln Gln Trp Asn Leu Ile Pro Val Gln Thr Ile Ser
    130                 135                 140

Leu Pro Gln Lys Pro Lys Ile Asp Lys Lys Leu Lys Asp His Pro Glu
145                 150                 155                 160

Tyr Ser Glu Thr Gly Asn Ile Ala Thr Gly Thr Ile Pro Gln Leu Met
                165                 170                 175

Gly Trp Thr Leu Val Pro Cys Ile Met Val Asn Asp Pro Lys Ile Gly
            180                 185                 190

Lys Asn Thr Gln Ile Lys Thr Thr Pro Tyr Tyr Ile Phe Lys Lys Tyr
        195                 200                 205

Gln Tyr Trp Lys Arg Ala Ile Gly Ser Asn Val Ser Leu Leu Pro His
    210                 215                 220

Gln Lys Lys Ser Tyr Asp Tyr Glu Trp Gly Thr Glu Glu Asn Gln Lys
225                 230                 235                 240

Thr Thr Ile Ile Asn Thr Val Gly Phe Gln Ile Asn Val Asp Ser Gly
                245                 250                 255

Met Lys Phe Glu Val Pro Glu Val Gly Gly Gly Thr Glu Glu Ile Lys
            260                 265                 270

Thr Gln Leu Asn Glu Glu Leu Lys Val Glu Tyr Ser Thr Asp Thr Lys
        275                 280                 285

Ile Met Lys Lys Tyr Gln Glu His Ser Glu Ile Asp Asn Pro Thr Asn
    290                 295                 300

Gln Thr Thr Asn Ser Ile Gly Phe Leu Thr Phe Thr Ser Leu Glu Leu
305                 310                 315                 320

Tyr Arg Tyr Asn Gly Ser Glu Ile Arg Ile Met Arg Met Glu Thr Ser
                325                 330                 335

Asp Asn Asp Thr Tyr Thr Leu Thr Ser Tyr Pro Asn His Arg Glu Ala
            340                 345                 350

Leu Leu Leu Leu Thr Asn His Ser Tyr Gln Glu Val Ser Arg Ile Pro
        355                 360                 365

Ala His Trp Arg Pro Leu Leu Val Asp Pro Ser Ser Val Pro Ser Leu
    370                 375                 380

Ala Ser Trp Ser Xaa Phe Pro Val Asn Cys Tyr Pro Leu Thr Ile Pro
385                 390                 395                 400

His Asn Ile Arg Ala Gly Ser Ile Lys Cys Lys Ala Trp Gly Ala Val
                405                 410                 415

Ser Leu Thr Leu Ile Ala Leu Arg Ser Leu Pro Ala Phe Gln Ser Gly
            420                 425                 430

Asn Leu Ser Cys Gln Leu His Ile Gly Gln Arg Ala Gly Arg Gly Gly
        435                 440                 445

Leu Arg Ile Gly Arg Ser Ser Ala Ser Ser Leu Thr Asp Ser
    450                 455                 460
```

<210> SEQ ID NO 83
<211> LENGTH: 340
<212> TYPE: DNA
<213> ORGANISM: Bacillus thuringiensis

<400> SEQUENCE: 83

```
tgtcagcacg tgaagtacat attgatgtaa ataataagac aggtcataca ttacaattag      60

aagataaaac aaaacttgat ggtggtagat ggcgaacatc acctacaaat gttgctaatg     120

atcaaattaa aacatttgta gcagaatcaa atggttttat gacaggtaca gaaggtacta     180
```

-continued

```
tatattatag tataaatgga gaagcagaaa ttagtttata ttttgacaat ccttttgcag    240

gttctaataa atatgatgga cattccaata aatctcaata tgaaattatt acccaaggag    300

gatcaggaaa tcaatctcat gtgacatata ctattcaaac                          340
```

<210> SEQ ID NO 84
<211> LENGTH: 112
<212> TYPE: PRT
<213> ORGANISM: Bacillus thuringiensis

<400> SEQUENCE: 84

```
Ser Ala Arg Glu Val His Ile Asp Val Asn Asn Lys Thr Gly His Thr
  1               5                  10                  15

Leu Gln Leu Glu Asp Lys Thr Lys Leu Asp Gly Gly Arg Trp Arg Thr
             20                  25                  30

Ser Pro Thr Asn Val Ala Asn Asp Gln Ile Lys Thr Phe Val Ala Glu
         35                  40                  45

Ser Asn Gly Phe Met Thr Gly Thr Glu Gly Thr Ile Tyr Tyr Ser Ile
     50                  55                  60

Asn Gly Glu Ala Glu Ile Ser Leu Tyr Phe Asp Asn Pro Phe Ala Gly
 65                  70                  75                  80

Ser Asn Lys Tyr Asp Gly His Ser Asn Lys Ser Gln Tyr Glu Ile Ile
                 85                  90                  95

Thr Gln Gly Gly Ser Gly Asn Gln Ser His Val Thr Tyr Thr Ile Gln
            100                 105                 110
```

<210> SEQ ID NO 85
<211> LENGTH: 1114
<212> TYPE: DNA
<213> ORGANISM: Bacillus thuringiensis

<400> SEQUENCE: 85

```
atgttagata ctaataaagt ttatgaaata agcaatcatg ctaatggact atatgcagca     60

acttatttaa gtttagatga ttcaggtgtt agtttaatga ataaaaatga tgatgatatt    120

gatgattata acttaaaatg gtttttattt cctattgatg atgatcaata tattattaca    180

agctatgcag caaataattg taaagtttgg aatgttaata atgataaaat aaatgtttcg    240

acttattctt caacaaattc aatacaaaaa tggcaaataa aagctaatgg ttcttcatat    300

gtaatacaaa gtgataatgg aaaagtctta acagcaggaa ccggtcaagc tcttggattg    360

atacgtttaa ctgatgaatc ctcaaataat cccaatcaac aatggaattt aacttctgta    420

caaacaattc aacttccacg aaaacctata atagatacaa aattaaaaga ttatcccaaa    480

tattcaccaa ctggaaatat agataatgga acatctcctc aattaatggg atggacatta    540

gtaccttgta ttatggtaaa tgatccaaat atagataaaa atactcaaat taaaactact    600

ccatattata ttttaaaaaa atatcaatat tggcaacgag cagtaggaag taatgtagct    660

ttacgtccac atgaaaaaaa atcatatact tatgaatggg gcacagaaat agatcaaaaa    720

acaacaatta taaatacatt aggatttcaa atcaatatag attcaggaat gaaatttgat    780

ataccagaag taggtggagg tacagatgaa ataaaaacac aactaaatga agaattaaaa    840

atagaatata gtcatgaaac taaaataatg gaaaaatatc aagaacaatc tgaaatagat    900

aatccaactg atcaatcaat gaattctata ggatttctta ctattacttc cttagaatta    960

tatagatata atggctcaga aattcgtata atgcaaattc aaacctcaga taatgatact   1020

tataatgtta cttcttatcc aaatcatcaa caagctttat tacttcttac aaatcattca   1080
```

```
tatgaagaag ttgaagaaat aacaagggcg aatt                         1114


<210> SEQ ID NO 86
<211> LENGTH: 371
<212> TYPE: PRT
<213> ORGANISM: Bacillus thuringiensis

<400> SEQUENCE: 86

Met Leu Asp Thr Asn Lys Val Tyr Glu Ile Ser Asn His Ala Asn Gly
  1               5                  10                  15

Leu Tyr Ala Ala Thr Tyr Leu Ser Leu Asp Asp Ser Gly Val Ser Leu
             20                  25                  30

Met Asn Lys Asn Asp Asp Asp Ile Asp Asp Tyr Asn Leu Lys Trp Phe
         35                  40                  45

Leu Phe Pro Ile Asp Asp Asp Gln Tyr Ile Ile Thr Ser Tyr Ala Ala
     50                  55                  60

Asn Asn Cys Lys Val Trp Asn Val Asn Asn Asp Lys Ile Asn Val Ser
 65                  70                  75                  80

Thr Tyr Ser Ser Thr Asn Ser Ile Gln Lys Trp Gln Ile Lys Ala Asn
                 85                  90                  95

Gly Ser Ser Tyr Val Ile Gln Ser Asp Asn Gly Lys Val Leu Thr Ala
            100                 105                 110

Gly Thr Gly Gln Ala Leu Gly Leu Ile Arg Leu Thr Asp Glu Ser Ser
        115                 120                 125

Asn Asn Pro Asn Gln Gln Trp Asn Leu Thr Ser Val Gln Thr Ile Gln
    130                 135                 140

Leu Pro Arg Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Arg Ala Val Gly Ser Asn Val Ala Leu Arg Pro His
    210                 215                 220

Glu Lys Lys Ser Tyr Thr Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser His Glu Thr Lys
        275                 280                 285

Ile Met Glu Lys Tyr Gln Glu Gln Ser Glu Ile Asp Asn Pro Thr Asp
    290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                325                 330                 335

Asp Asn Asp Thr Tyr Asn Val Thr Ser Tyr Pro Asn His Gln Gln Ala
            340                 345                 350

Leu Leu Leu Leu Thr Asn His Ser Tyr Glu Glu Val Glu Glu Ile Thr
        355                 360                 365
```

```
Arg Ala Asn
    370


<210> SEQ ID NO 87
<211> LENGTH: 341
<212> TYPE: DNA
<213> ORGANISM: Bacillus thuringiensis

<400> SEQUENCE: 87

atgtcagctg gcgaagttca tattgaaata aacaataaaa cacgtcatac attacaatta     60

gaggataaaa ctaaacttag cggcggtaga tggcgaacat cacctacaaa tgttgctcgt    120

gatacaatta aaacatttgt agcagaatca catggtttta tgacaggagt agaaggtatt    180

atatatttta gtgtaaacgg agacgcagaa attagtttac attttgacaa tccttatata    240

ggttctaata aatgtgatgg ttcttctgat aaacctgaat atgaagttat tactcaaagc    300

ggatcaggag ataaatctca tgtcacttat acaattcaaa c                        341


<210> SEQ ID NO 88
<211> LENGTH: 113
<212> TYPE: PRT
<213> ORGANISM: Bacillus thuringiensis

<400> SEQUENCE: 88

Met Ser Ala Gly Glu Val His Ile Glu Ile Asn Asn Lys Thr Arg His
  1               5                  10                  15

Thr Leu Gln Leu Glu Asp Lys Thr Lys Leu Ser Gly Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Val Glu Gly Ile Ile Tyr Phe Ser
     50                  55                  60

Val Asn Gly Asp Ala Glu Ile Ser Leu His Phe Asp Asn Pro Tyr Ile
 65                  70                  75                  80

Gly Ser Asn Lys Cys Asp Gly Ser Ser Asp Lys Pro Glu Tyr Glu Val
                 85                  90                  95

Ile Thr Gln Ser Gly Ser Gly Asp Lys Ser His Val Thr Tyr Thr Ile
            100                 105                 110

Gln


<210> SEQ ID NO 89
<211> LENGTH: 1186
<212> TYPE: DNA
<213> ORGANISM: Bacillus thuringiensis

<400> SEQUENCE: 89

atgttagata caaataaagt ttatgaaata agcaatcttg ctaatggatt atatacatca     60

acttatttaa gtcttgatga ttcaggtgtt agtttaatga gtaaaaagga tgaagatatt    120

gatgattaca atttaaaatg gtttttattt cctattgata ataatcaata tattattaca    180

agctatggag ctaataattg taaagtttgg aatgttaaaa atgataaaat aaatgtttca    240

acttattctt caacaaactc tgtacaaaaa tggcaaataa aagctaaaga ttcttcatat    300

ataatacaaa gtgataatgg aaaggtctta acagcaggag taggtcaatc tcttggaata    360

gtacgcctaa ctgatgaatt tccagagaat tctaaccaac aatggaattt aactcctgta    420

caaacaattc aactcccaca aaaacctaaa atagatgaaa aattaaaaga tcatcctgaa    480

tattcagaaa ccggaaatat aaatcctaaa acaactcctc aattaatggg atggacatta    540
```

```
gtaccttgta ttatggtaaa tgattcaaaa atagataaaa acactcaaat taaaactact    600

ccatattata tttttaaaaa atataaatac tggaatctag caaaaggaag taatgtatct    660

ttacttccac atcaaaaaag atcatatgat tatgaatggg gtacagaaaa aaatcaaaaa    720

acaactatta ttaatacagt aggattgcaa attaatatag attcaggaat gaaatttgaa    780

gtaccagaag taggaggagg tacagaagac ataaaaacac aattaactga agaattaaaa    840

gttgaatata gcactgaaac caaaataatg acgaaatatc aagaacactc agagatagat    900

aatccaacta atcaaccaat gaattctata ggacttctta tttatacttc tttagaatta    960

tatcgatata acggrcagaa attaagataa tggacataga aacttcagat catgatactt   1020

acactcttac ttcttatcca aatcataaag aagcattatt acttctcaca aaccattctt   1080

atgaagaagt agaagaaatt acaagggcga attccagcac actggcggcc gttactagtg   1140

gatccgagct cggtaccaag cttggcgtgt caggtcaaag ggttca                  1186


<210> SEQ ID NO 90
<211> LENGTH: 392
<212> TYPE: PRT
<213> ORGANISM: Bacillus thuringiensis

<400> SEQUENCE: 90

Met Leu Asp Thr Asn Lys Val Tyr Glu Ile Ser Asn Leu Ala Asn Gly
  1               5                  10                  15

Leu Tyr Thr Ser Thr Tyr Leu Ser Leu Asp Asp Ser Gly Val Ser Leu
             20                  25                  30

Met Ser Lys Lys Asp Glu Asp Ile Asp Asp Tyr Asn Leu Lys Trp Phe
         35                  40                  45

Leu Phe Pro Ile Asp Asn Asn Gln Tyr Ile Ile Thr Ser Tyr Gly Ala
     50                  55                  60

Asn Asn Cys Lys Val Trp Asn Val Lys Asn Asp Lys Ile Asn Val Ser
 65                  70                  75                  80

Thr Tyr Ser Ser Thr Asn Ser Val Gln Lys Trp Gln Ile Lys Ala Lys
                 85                  90                  95

Asp Ser Ser Tyr Ile Ile Gln Ser Asp Asn Gly Lys Val Leu Thr Ala
            100                 105                 110

Gly Val Gly Gln Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Lys Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Thr Ile Ile Asn Thr Val Gly Leu Gln Ile Asn Ile Asp Ser Gly
                245                 250                 255
```

```
Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Gln Lys Leu Arg Trp Thr Lys Leu Gln Ile Met
                325                 330                 335

Ile Leu Thr Leu Leu Leu Leu Ile Gln Ile Ile Lys Lys His Tyr Tyr
            340                 345                 350

Phe Ser Gln Thr Ile Leu Met Lys Lys Lys Lys Leu Gln Gly Arg Ile
        355                 360                 365

Pro Ala His Trp Arg Pro Leu Leu Val Asp Pro Ser Ser Val Pro Ser
    370                 375                 380

Leu Ala Cys Gln Val Lys Gly Phe
385                 390


<210> SEQ ID NO 91
<211> LENGTH: 341
<212> TYPE: DNA
<213> ORGANISM: Bacillus thuringiensis

<400> SEQUENCE: 91

atgtcagcag ccgaagtaca tattgaaata ataaatcata caggtcatac cttacaaatg      60

gataaaagaa ctagacttgc acatggtgaa tggattatta cacccgtgaa tgttccaaat     120

aattcttctg atttatttca agcaggttct gatggagttt tgacaggagt agaaggaata     180

ataatttata ctataaatgg agaaatagaa attaccttac attttgacaa tccttatgca     240

ggttctaata aatattctgg acgttctagt gatgatgatt ataaagttat aactgaagca     300

agagcagaac atagagctaa taatcatgat catgtaactt a                          341


<210> SEQ ID NO 92
<211> LENGTH: 113
<212> TYPE: PRT
<213> ORGANISM: Bacillus thuringiensis

<400> SEQUENCE: 92

Met Ser Ala Ala Glu Val His Ile Glu Ile Ile Asn His Thr Gly His
  1               5                  10                  15

Thr Leu Gln Met Asp Lys Arg Thr Arg Leu Ala His Gly Glu Trp Ile
            20                  25                  30

Ile Thr Pro Val Asn Val Pro Asn Asn Ser Ser Asp Leu Phe Gln Ala
        35                  40                  45

Gly Ser Asp Gly Val Leu Thr Gly Val Glu Gly Ile Ile Ile Tyr Thr
     50                  55                  60

Ile Asn Gly Glu Ile Glu Ile Thr Leu His Phe Asp Asn Pro Tyr Ala
 65                  70                  75                  80

Gly Ser Asn Lys Tyr Ser Gly Arg Ser Ser Asp Asp Asp Tyr Lys Val
                 85                  90                  95

Ile Thr Glu Ala Arg Ala Glu His Arg Ala Asn Asn His Asp His Val
            100                 105                 110

Thr
```

<210> SEQ ID NO 93
<211> LENGTH: 341
<212> TYPE: DNA
<213> ORGANISM: Bacillus thuringiensis

<400> SEQUENCE: 93

```
atgtcagatc gcgaagtaca tattgaaata ataaatcata caggtcatac cttacaaatg      60

gataaaagaa ctagacttgc acatggtgaa tggattatta cacccgtgaa tgttccaaat     120

aattcttctg atttatttca agcaggttct gatggagttt tgacaggagt agaaggaata     180

ataatttata ctataaatgg agaaatagaa attaccttac attttgacaa tccttatgca     240

ggttctaata aatattctgg acgttctagt gatgatgatt ataaagttat aactgaagca     300

agagcagaac atagagctaa taatcatgat catgtaactt a                         341
```

<210> SEQ ID NO 94
<211> LENGTH: 113
<212> TYPE: PRT
<213> ORGANISM: Bacillus thuringiensis

<400> SEQUENCE: 94

```
Met Ser Asp Arg Glu Val His Ile Glu Ile Ile Asn His Thr Gly His
  1               5                  10                  15

Thr Leu Gln Met Asp Lys Arg Thr Arg Leu Ala His Gly Glu Trp Ile
             20                  25                  30

Ile Thr Pro Val Asn Val Pro Asn Asn Ser Ser Asp Leu Phe Gln Ala
         35                  40                  45

Gly Ser Asp Gly Val Leu Thr Gly Val Glu Gly Ile Ile Ile Tyr Thr
     50                  55                  60

Ile Asn Gly Glu Ile Glu Ile Thr Leu His Phe Asp Asn Pro Tyr Ala
 65                  70                  75                  80

Gly Ser Asn Lys Tyr Ser Gly Arg Ser Ser Asp Asp Asp Tyr Lys Val
                 85                  90                  95

Ile Thr Glu Ala Arg Ala Glu His Arg Ala Asn Asn His Asp His Val
            100                 105                 110

Thr
```

<210> SEQ ID NO 95
<211> LENGTH: 353
<212> TYPE: DNA
<213> ORGANISM: Bacillus thuringiensis

<400> SEQUENCE: 95

```
atgtcagcac gtgaagtaca tattgaaata ataaatcata caggtcatac cttacaaatg      60

gataaaagaa ctagacttgc acatggtgaa tggattatta cacccgtgaa tgttccaaat     120

aattcttctg atttatttca agcaggttct gatggagttt tgacaggagt agaaggaata     180

ataatttata ctataaatgg agaaatagaa attaccttac attttgacaa tccttatgca     240

ggttctaata aatattctgg acgttctagt gatgatgatt ataaagttat aactgaagca     300

agagcagaac atagagctaa taatcatgat catgtaacat atacgattca aac            353
```

<210> SEQ ID NO 96
<211> LENGTH: 117
<212> TYPE: PRT
<213> ORGANISM: Bacillus thuringiensis

<400> SEQUENCE: 96

```
Met Ser Ala Arg Glu Val His Ile Glu Ile Ile Asn His Thr Gly His
```

-continued

```
  1               5                  10                  15

Thr Leu Gln Met Asp Lys Arg Thr Arg Leu Ala His Gly Glu Trp Ile
            20                  25                  30

Ile Thr Pro Val Asn Val Pro Asn Asn Ser Ser Asp Leu Phe Gln Ala
        35                  40                  45

Gly Ser Asp Gly Val Leu Thr Gly Val Glu Gly Ile Ile Ile Tyr Thr
    50                  55                  60

Ile Asn Gly Glu Ile Glu Ile Thr Leu His Phe Asp Asn Pro Tyr Ala
 65                  70                  75                  80

Gly Ser Asn Lys Tyr Ser Gly Arg Ser Ser Asp Asp Asp Tyr Lys Val
                85                  90                  95

Ile Thr Glu Ala Arg Ala Glu His Arg Ala Asn Asn His Asp His Val
            100                 105                 110

Thr Tyr Thr Ile Gln
        115


<210> SEQ ID NO 97
<211> LENGTH: 353
<212> TYPE: DNA
<213> ORGANISM: Bacillus thuringiensis

<400> SEQUENCE: 97

atgtcagctc gtgaagtaca tattgaaata ataaatcata caggtcatac cttacaaatg      60

gataaaagaa ctagacttgc acatggtgaa tggattatta cacccgtgaa tgttccaaat     120

aattcttctg atttatttca agcaggttct gatggagttt tgacaggagt agaaggaata     180

ataatttata ctataaatgg agaaatagaa attaccttac attttgacaa tccttatgca     240

ggttctaata aatattctgg acgttctagt gatgatgatt ataaagttat aactgaagca     300

agagcagaac atagagctaa taatcatgat catgtgacat atacaattca aac            353


<210> SEQ ID NO 98
<211> LENGTH: 117
<212> TYPE: PRT
<213> ORGANISM: Bacillus thuringiensis

<400> SEQUENCE: 98

Met Ser Ala Arg Glu Val His Ile Glu Ile Ile Asn His Thr Gly His
  1               5                  10                  15

Thr Leu Gln Met Asp Lys Arg Thr Arg Leu Ala His Gly Glu Trp Ile
            20                  25                  30

Ile Thr Pro Val Asn Val Pro Asn Asn Ser Ser Asp Leu Phe Gln Ala
        35                  40                  45

Gly Ser Asp Gly Val Leu Thr Gly Val Glu Gly Ile Ile Ile Tyr Thr
    50                  55                  60

Ile Asn Gly Glu Ile Glu Ile Thr Leu His Phe Asp Asn Pro Tyr Ala
 65                  70                  75                  80

Gly Ser Asn Lys Tyr Ser Gly Arg Ser Ser Asp Asp Asp Tyr Lys Val
                85                  90                  95

Ile Thr Glu Ala Arg Ala Glu His Arg Ala Asn Asn His Asp His Val
            100                 105                 110

Thr Tyr Thr Ile Gln
        115


<210> SEQ ID NO 99
<211> LENGTH: 353
<212> TYPE: DNA
```

<213> ORGANISM: Bacillus thuringiensis

<400> SEQUENCE: 99

```
atgtcaggtc gcgaagttca tattgaaata ataaatcata caggtcatac cttacaaatg     60

gataaaagaa ctagacttgc acatggtgaa tggattatta cacccgtgaa tgttccaaat    120

aattcttctg atttatttca agcaggttct gatggagttt tgacaggagt agaaggaata    180

ataatttata ctataaatgg agaaatagaa attaccttac attttgacaa tccttatgca    240

ggttctaata aatattctgg acgttctagt gatgatgatt ataaagttat aactgaagca    300

agagcagaac atagagctaa taatcatgat catgtaacat atacgattca aac           353
```

<210> SEQ ID NO 100
<211> LENGTH: 117
<212> TYPE: PRT
<213> ORGANISM: Bacillus thuringiensis

<400> SEQUENCE: 100

```
Met Ser Gly Arg Glu Val His Ile Glu Ile Ile Asn His Thr Gly His
  1               5                  10                  15

Thr Leu Gln Met Asp Lys Arg Thr Arg Leu Ala His Gly Glu Trp Ile
             20                  25                  30

Ile Thr Pro Val Asn Val Pro Asn Asn Ser Ser Asp Leu Phe Gln Ala
         35                  40                  45

Gly Ser Asp Gly Val Leu Thr Gly Val Glu Gly Ile Ile Ile Tyr Thr
     50                  55                  60

Ile Asn Gly Glu Ile Glu Ile Thr Leu His Phe Asp Asn Pro Tyr Ala
 65                  70                  75                  80

Gly Ser Asn Lys Tyr Ser Gly Arg Ser Ser Asp Asp Asp Tyr Lys Val
                 85                  90                  95

Ile Thr Glu Ala Arg Ala Glu His Arg Ala Asn Asn His Asp His Val
            100                 105                 110

Thr Tyr Thr Ile Gln
        115
```

<210> SEQ ID NO 101
<211> LENGTH: 353
<212> TYPE: DNA
<213> ORGANISM: Bacillus thuringiensis

<400> SEQUENCE: 101

```
atgtcagctc gtgaagtaca tattgaaata ataaatcata caggtcatac cttacaaatg     60

gataaaagaa ctagacttgc acatggtgaa tggattatta cacccgtgaa tgttccaaat    120

aattcttctg atttatttca agcaggttct gatggagttt tgacaggagt agaaggaata    180

ataatttata ctataaatgg agaaatagaa attaccttac attttgacaa tccttatgca    240

ggttctaata aatattctgg acgttctagt gatgatgatt ataaagttat aactgaagca    300

agagcagaac atagagctaa taatcatgat catgttacgt atacaattca aac           353
```

<210> SEQ ID NO 102
<211> LENGTH: 117
<212> TYPE: PRT
<213> ORGANISM: Bacillus thuringiensis

<400> SEQUENCE: 102

```
Met Ser Ala Arg Glu Val His Ile Glu Ile Ile Asn His Thr Gly His
  1               5                  10                  15
```

```
Thr Leu Gln Met Asp Lys Arg Thr Arg Leu Ala His Gly Glu Trp Ile
            20                  25                  30

Ile Thr Pro Val Asn Val Pro Asn Asn Ser Ser Asp Leu Phe Gln Ala
        35                  40                  45

Gly Ser Asp Gly Val Leu Thr Gly Val Glu Gly Ile Ile Ile Tyr Thr
    50                  55                  60

Ile Asn Gly Glu Ile Glu Ile Thr Leu His Phe Asp Asn Pro Tyr Ala
65                  70                  75                  80

Gly Ser Asn Lys Tyr Ser Gly Arg Ser Ser Asp Asp Asp Tyr Lys Val
                85                  90                  95

Ile Thr Glu Ala Arg Ala Glu His Arg Ala Asn Asn His Asp His Val
            100                 105                 110

Thr Tyr Thr Ile Gln
        115


<210> SEQ ID NO 103
<211> LENGTH: 353
<212> TYPE: DNA
<213> ORGANISM: Bacillus thuringiensis

<400> SEQUENCE: 103

atgtcaggtc gcgaagtaga tattgaaata ataaatcata caggtcatac cttacaaatg      60

gataaaagaa ctagacttgc acatggtgaa tggattatta cacccgtgaa tgttccaaat     120

aattcttctg atttatttca agcaggttct gatggagttt tgacaggagt agaaggaata     180

ataatttata ctataaatgg agaaatagaa attaccttac attttgacaa tccttatgca     240

ggttctaata aatattctgg acgttctagt gatgatgatt ataaagttat aactgaagcg     300

agagcagaac atagagctaa taatcatgat catgtaacat atactattca gac           353


<210> SEQ ID NO 104
<211> LENGTH: 117
<212> TYPE: PRT
<213> ORGANISM: Bacillus thuringiensis

<400> SEQUENCE: 104

Met Ser Gly Arg Glu Val Asp Ile Glu Ile Ile Asn His Thr Gly His
1               5                   10                  15

Thr Leu Gln Met Asp Lys Arg Thr Arg Leu Ala His Gly Glu Trp Ile
            20                  25                  30

Ile Thr Pro Val Asn Val Pro Asn Asn Ser Ser Asp Leu Phe Gln Ala
        35                  40                  45

Gly Ser Asp Gly Val Leu Thr Gly Val Glu Gly Ile Ile Ile Tyr Thr
    50                  55                  60

Ile Asn Gly Glu Ile Glu Ile Thr Leu His Phe Asp Asn Pro Tyr Ala
65                  70                  75                  80

Gly Ser Asn Lys Tyr Ser Gly Arg Ser Ser Asp Asp Asp Tyr Lys Val
                85                  90                  95

Ile Thr Glu Ala Arg Ala Glu His Arg Ala Asn Asn His Asp His Val
            100                 105                 110

Thr Tyr Thr Ile Gln
        115


<210> SEQ ID NO 105
<211> LENGTH: 353
<212> TYPE: DNA
<213> ORGANISM: Bacillus thuringiensis
```

<400> SEQUENCE: 105
atgtcagcac gtgaagtaca tattgaaata ataaatcata caggtcatac cttacaaatg 60
gataaaagaa ctagacttgc acatggtgaa tggattatta cacccgtgaa tgttccaaat 120
aattcttctg atttatttca agcaggttct gatggagttt tgacaggagt agaaggaata 180
ataatttata ctataaatgg agaaatagaa attaccttac attttgacaa tccttatgca 240
ggttctaata aatattctgg acgttctagt gatgatgatt ataaagttat aactgaagca 300
agagcagaac atagagctaa taatcatgat catgtaacat ataccattca aac 353

<210> SEQ ID NO 106
<211> LENGTH: 117
<212> TYPE: PRT
<213> ORGANISM: Unknown
<220> FEATURE:
<223> OTHER INFORMATION: Description of Unknown Organism:protein

<400> SEQUENCE: 106

Met Ser Ala Arg Glu Val His Ile Glu Ile Ile Asn His Thr Gly His
1 5 10 15

Thr Leu Gln Met Asp Lys Arg Thr Arg Leu Ala His Gly Glu Trp Ile
20 25 30

Ile Thr Pro Val Asn Val Pro Asn Asn Ser Ser Asp Leu Phe Gln Ala
35 40 45

Gly Ser Asp Gly Val Leu Thr Gly Val Glu Gly Ile Ile Ile Tyr Thr
50 55 60

Ile Asn Gly Glu Ile Glu Ile Thr Leu His Phe Asp Asn Pro Tyr Ala
65 70 75 80

Gly Ser Asn Lys Tyr Ser Gly Arg Ser Ser Asp Asp Asp Tyr Lys Val
85 90 95

Ile Thr Glu Ala Arg Ala Glu His Arg Ala Asn Asn His Asp His Val
100 105 110

Thr Tyr Thr Ile Gln
115

<210> SEQ ID NO 107
<211> LENGTH: 341
<212> TYPE: DNA
<213> ORGANISM: Bacillus thuringiensis

<400> SEQUENCE: 107
atgtcaggtc gcgaagttca tattgatgta aataataaga caggtcatac attacaatta 60
gaagataaaa caagacttga tggtggtaga tggcgaacat cacctacaaa tgttgctaat 120
gatcaaatta aaacatttgt agcagaatca catggtttta tgacaggtac agaaggtact 180
atatattata gtataaatgg agaagcagaa attagtttat attttgacaa tccttattca 240
ggttctaata aatatgatgg gcattccaat aaaaatcaat atgaagttat tacccaagga 300
ggatcaggaa atcaatctca tctgacgtat acaattcaaa c 341

<210> SEQ ID NO 108
<211> LENGTH: 113
<212> TYPE: PRT
<213> ORGANISM: Bacillus thuringiensis

<400> SEQUENCE: 108

Met Ser Gly Arg Glu Val His Ile Asp Val Asn Asn Lys Thr Gly His
1 5 10 15

-continued

```
Thr Leu Gln Leu Glu Asp Lys Thr Arg Leu Asp Gly Gly Arg Trp Arg
            20                  25                  30

Thr Ser Pro Thr Asn Val Ala Asn Asp Gln Ile Lys Thr Phe Val Ala
        35                  40                  45

Glu Ser His Gly Phe Met Thr Gly Thr Glu Gly Thr Ile Tyr Tyr Ser
    50                  55                  60

Ile Asn Gly Glu Ala Glu Ile Ser Leu Tyr Phe Asp Asn Pro Tyr Ser
65                  70                  75                  80

Gly Ser Asn Lys Tyr Asp Gly His Ser Asn Lys Asn Gln Tyr Glu Val
                85                  90                  95

Ile Thr Gln Gly Gly Ser Gly Asn Gln Ser His Leu Thr Tyr Thr Ile
            100                 105                 110

Gln


<210> SEQ ID NO 109
<211> LENGTH: 1114
<212> TYPE: DNA
<213> ORGANISM: Bacillus thuringiensis

<400> SEQUENCE: 109

atgttagata ctaataaagt atatgaaata agtaattatg ctaatggatt acatgcagca     60

acttatttaa gtttagatga ttcaggtgtt agtttaatga ataaaaatga tgatgatatt    120

gatgactata atttaaggtg gtttttattt cctattgatg ataatcaata tattattaca    180

agctacgcag cgaataattg taaggtttgg aatgttaata atgataaaat aaatgtttca    240

acttattctt caacaaactc gatacagaaa tggcaaataa aagctaatgc ttcttcgtat    300

gtaatacaaa gtaataatgg gaaagttcta acagcaggaa ccggtcaatc tcttggatta    360

atacgtttaa cggatgaatc accagataat cccaatcaac aatggaattt aactcctgta    420

caaacaattc aactcccacc aaaacctaca atagatacaa agttaaaaga ttaccccaaa    480

tattcacaaa ctggcaatat agacaaggga acacctcctc aattaatggg atggacatta    540

ataccttgta ttatggtaaa tgatccaaat atagataaaa acactcaaat caaaactact    600

ccatattata ttttaaaaaa atatcaatat tggcaacaag cagtaggaag taatgtagct    660

ttacgtccgc atgaaaaaaa atcatatgct tatgagtggg gtacagaaat agatcaaaaa    720

acaactatca ttaatacatt aggatttcag attaatatag attcgggaat ggaatttgat    780

ataccagaag taggtggagg tacagatgaa ataaaaaacac aattaaacga agaattaaaa    840

atagaatata gccgtgaaac caaaataatg gaaaaatatc aggaacaatc agagatagat    900

aatccaactg atcaatcaat gaattctata ggattcctca ctattacttc tttagaatta    960

tatcgatata atggttcgga aattagtgta atgaaaattc aaacttcaga taatgatact   1020

tacaatgtga cctcttatcc agatcatcaa caagctctat tacttcttac aaatcattca   1080

tatgaacaag tacaagaaat aacaagggcg aatt                               1114


<210> SEQ ID NO 110
<211> LENGTH: 371
<212> TYPE: PRT
<213> ORGANISM: Bacillus thuringiensis

<400> SEQUENCE: 110

Met Leu Asp Thr Asn Lys Val Tyr Glu Ile Ser Asn Tyr Ala Asn Gly
  1               5                  10                  15

Leu His Ala Ala Thr Tyr Leu Ser Leu Asp Asp Ser Gly Val Ser Leu
            20                  25                  30
```

-continued

```
Met Asn Lys Asn Asp Asp Asp Ile Asp Asp Tyr Asn Leu Arg Trp Phe
        35                  40                  45

Leu Phe Pro Ile Asp Asp Asn Gln Tyr Ile Ile Thr Ser Tyr Ala Ala
    50                  55                  60

Asn Asn Cys Lys Val Trp Asn Val Asn Asn Asp Lys Ile Asn Val Ser
65                  70                  75                  80

Thr Tyr Ser Ser Thr Asn Ser Ile Gln Lys Trp Gln Ile Lys Ala Asn
                85                  90                  95

Ala Ser Ser Tyr Val Ile Gln Ser Asn Asn Gly Lys Val Leu Thr Ala
            100                 105                 110

Gly Thr Gly Gln Ser Leu Gly Leu Ile Arg Leu Thr Asp Glu Ser Pro
        115                 120                 125

Asp Asn Pro Asn Gln Gln Trp Asn Leu Thr Pro Val Gln Thr Ile Gln
    130                 135                 140

Leu Pro Pro Lys Pro Thr Ile Asp Thr Lys Leu Lys Asp Tyr Pro Lys
145                 150                 155                 160

Tyr Ser Gln Thr Gly Asn Ile Asp Lys Gly Thr Pro Pro Gln Leu Met
                165                 170                 175

Gly Trp Thr Leu Ile Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Gln Ala Val Gly Ser Asn Val Ala Leu Arg Pro His
    210                 215                 220

Glu Lys Lys Ser Tyr Ala Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Glu Phe Asp Ile Pro Glu Val Gly Gly Gly Thr Asp Glu Ile Lys
            260                 265                 270

Thr Gln Leu Asn Glu Glu Leu Lys Ile Glu Tyr Ser Arg Glu Thr Lys
        275                 280                 285

Ile Met Glu Lys Tyr Gln Glu Gln Ser Glu Ile Asp Asn Pro Thr Asp
    290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Ser Val Met Lys Ile Gln Thr Ser
                325                 330                 335

Asp Asn Asp Thr Tyr Asn Val Thr Ser Tyr Pro Asp His Gln Gln Ala
            340                 345                 350

Leu Leu Leu Leu Thr Asn His Ser Tyr Glu Gln Val Gln Glu Ile Thr
        355                 360                 365

Arg Ala Asn
    370
```

```
<210> SEQ ID NO 111
<211> LENGTH: 341
<212> TYPE: DNA
<213> ORGANISM: Bacillus thuringiensis

<400> SEQUENCE: 111

atgtcagctc gtgaagtaca tattgaaata aacaataaaa cacgtcatac attacaatta      60

gaggataaaa ctaaacttag cggcggtaga tggcgaacat cacctacaaa tgttgctcgt     120
```

-continued

```
gatacaatta aaacatttgt agcagaatca catggtttta tgacaggagt agaaggtatt    180

atatatttta gtgtaaacgg agacgcagaa attagtttac attttgacaa tccttatata    240

ggttctaata aatgtgatgg ttcttctgat aaacctgaat atgaagttat tactcaaagc    300

ggatcaggag ataaatctca tgttacatat acaattcaga c                        341
```

```
<210> SEQ ID NO 112
<211> LENGTH: 113
<212> TYPE: PRT
<213> ORGANISM: Bacillus thuringiensis

<400> SEQUENCE: 112

Met Ser Ala Arg Glu Val His Ile Glu Ile Asn Asn Lys Thr Arg His
  1               5                  10                  15

Thr Leu Gln Leu Glu Asp Lys Thr Lys Leu Ser Gly Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Val Glu Gly Ile Ile Tyr Phe Ser
     50                  55                  60

Val Asn Gly Asp Ala Glu Ile Ser Leu His Phe Asp Asn Pro Tyr Ile
 65                  70                  75                  80

Gly Ser Asn Lys Cys Asp Gly Ser Ser Asp Lys Pro Glu Tyr Glu Val
                 85                  90                  95

Ile Thr Gln Ser Gly Ser Gly Asp Lys Ser His Val Thr Tyr Thr Ile
            100                 105                 110

Gln
```

```
<210> SEQ ID NO 113
<211> LENGTH: 360
<212> TYPE: DNA
<213> ORGANISM: Bacillus thuringiensis

<400> SEQUENCE: 113

atgtcagctc gcgaagtaca cattgaaata aacaataaaa cacgtcatac attacaatta     60

gaggataaaa ctaaacttag cggcggtaga tggcgaacat cacctacaaa tgttgctcgt    120

gatacaatta aaacatttgt agcagaatca catggtttta tgacaggagt agaaggtatt    180

atatatttta gtgtaaacgg agacgcagaa attagtttac attttgacaa tccttatata    240

ggttctaata aatgtgatgg ttcttctgat aaacctgaat atgaagttat tactcaaagc    300

ggatcaggag ataaatctca tgtgacatat actattcaga cagtatcttt acgattataa    360
```

```
<210> SEQ ID NO 114
<211> LENGTH: 119
<212> TYPE: PRT
<213> ORGANISM: Bacillus thuringiensis

<400> SEQUENCE: 114

Met Ser Ala Arg Glu Val His Ile Glu Ile Asn Asn Lys Thr Arg His
  1               5                  10                  15

Thr Leu Gln Leu Glu Asp Lys Thr Lys Leu Ser Gly Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Val Glu Gly Ile Ile Tyr Phe Ser
     50                  55                  60
```

-continued

```
Val Asn Gly Asp Ala Glu Ile Ser Leu His Phe Asp Asn Pro Tyr Ile
 65                  70                  75                  80

Gly Ser Asn Lys Cys Asp Gly Ser Ser Asp Lys Pro Glu Tyr Glu Val
                 85                  90                  95

Ile Thr Gln Ser Gly Ser Gly Asp Lys Ser His Val Thr Tyr Thr Ile
            100                 105                 110

Gln Thr Val Ser Leu Arg Leu
        115
```

<210> SEQ ID NO 115
<211> LENGTH: 1158
<212> TYPE: DNA
<213> ORGANISM: Bacillus thuringiensis

<400> SEQUENCE: 115

```
atgttagata ctaataaagt ttatgaaata agcaatcttg ctaatggatt atatacatca     60

acttatttaa gtcttgatga ttcaggtgtt agtttaatga gtaaaaagga tgaagatatt    120

gatgattaca atttaaaatg gtttttattt cctattgata ataatcaata tattattaca    180

agctatggag ctaataattg taaagtttgg aatgttaaaa atgataaaat aaatgtttca    240

acttattctt caacaaactc tgtacaaaaa tggcaaataa aagctaaaga ttcttcatat    300

ataatacaaa gtgataatgg aaaggtctta acagcaggag taggtgaatc tcttggaata    360

gtacgcctaa ctgatgaatt tccagagaat tctaaccaac aatggaattt aactcctgta    420

caaacaattc aactcccaca aaaacctaaa atagatgaaa aattaaaaga tcatcctgaa    480

tattcagaaa ccggaaatat aaatcctaaa acaactcctc aattaatggg atggacatta    540

gtaccttgta ttatggtaaa tgattcagga atagataaaa acactcaaat taaaactact    600

ccatattata tttttaaaaa atataaatac tggaatctag caaaaggaag taatgtatct    660

ttacttccac atcaaaaaag atcatatgat tatgaatggg gtacagaaaa aaatcaaaaa    720

acatctatta ttaatacagt aggattgcaa attaatatag attcaggaat gaaatttgaa    780

gtaccagaag taggaggagg tacagaagac ataaaaacac aattaactga agaattaaaa    840

gttgaatata gcactgaaac caaaataatg acgaaatatc aagaacactc agagatagat    900

aatccaacta atcaaccaat gaattctata ggacttctta tttatacttc tttagaatta    960

tatcgatata acggtacaga aattaagata atggacatag aaacttcaga tcatgatact   1020

tacactctta cttcttatcc aaatcataaa gaagcattat tacttctcac aaaccattcg   1080

tatgaagaag tagaagaaat aacaaaaata cctaagcata cacttataaa attgaaaaaa   1140

cattatttta aaaaataa                                                  1158
```

<210> SEQ ID NO 116
<211> LENGTH: 385
<212> TYPE: PRT
<213> ORGANISM: Bacillus thuringiensis

<400> SEQUENCE: 116

```
Met Leu Asp Thr Asn Lys Val Tyr Glu Ile Ser Asn Leu Ala Asn Gly
  1               5                  10                  15

Leu Tyr Thr Ser Thr Tyr Leu Ser Leu Asp Asp Ser Gly Val Ser Leu
             20                  25                  30

Met Ser Lys Lys Asp Glu Asp Ile Asp Asp Tyr Asn Leu Lys Trp Phe
         35                  40                  45

Leu Phe Pro Ile Asp Asn Asn Gln Tyr Ile Ile Thr Ser Tyr Gly Ala
     50                  55                  60
```

-continued

```
Asn Asn Cys Lys Val Trp Asn Val Lys Asn Asp Lys Ile Asn Val Ser
 65                  70                  75                  80

Thr Tyr Ser Ser Thr Asn Ser Val Gln Lys Trp Gln Ile Lys Ala Lys
                85                  90                  95

Asp Ser Ser Tyr Ile Ile Gln Ser Asp Asn Gly Lys Val Leu Thr Ala
            100                 105                 110

Gly Val Gly Glu Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Gly Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Ser Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350

Leu Leu Leu Leu Thr Asn His Ser Tyr Glu Glu Val Glu Glu Ile Thr
        355                 360                 365

Lys Ile Pro Lys His Thr Leu Ile Lys Leu Lys Lys His Tyr Phe Lys
    370                 375                 380

Lys
385
```

<210> SEQ ID NO 117
<211> LENGTH: 341
<212> TYPE: DNA
<213> ORGANISM: Bacillus thuringiensis

<400> SEQUENCE: 117

```
atgtcagcac gccaacttca tattgatgta aataataaga caggtcatac attacaatta      60

gaagataaaa caaaacttga tggtggtaga tggcgaacat cacctacaaa tgttgctaat     120

gatcaaatta aaacatttgt agcagaatca catggtttta tgacaggtac agaaggtact     180

atatattata gtataaatgg agaagcagaa attagtttat attttgacaa tccttattca     240
```

-continued

```
ggttctaata aatatgatgg gcattctaat aaaaatcaat atgaagttat tacccaagga    300

ggatcaggaa atcaatctca tgtgacttat acgattcaca c                        341


<210> SEQ ID NO 118
<211> LENGTH: 113
<212> TYPE: PRT
<213> ORGANISM: Bacillus thuringiensis

<400> SEQUENCE: 118

Met Ser Ala Arg Gln Leu His Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Phe Val Ala
         35                  40                  45

Glu Ser His Gly Phe Met Thr Gly Thr Glu Gly Thr Ile Tyr Tyr Ser
     50                  55                  60

Ile Asn Gly Glu Ala Glu Ile Ser Leu Tyr Phe Asp Asn Pro Tyr Ser
 65                  70                  75                  80

Gly Ser Asn Lys Tyr Asp Gly His Ser Asn Lys Asn Gln Tyr Glu Val
                 85                  90                  95

Ile Thr Gln Gly Gly Ser Gly Asn Gln Ser His Val Thr Tyr Thr Ile
            100                 105                 110

His


<210> SEQ ID NO 119
<211> LENGTH: 341
<212> TYPE: DNA
<213> ORGANISM: Bacillus thuringiensis

<400> SEQUENCE: 119

atgtcaggtc gtgaagttca tattgatgta aataataaga caggtcatac attacaatta     60

gaagataaaa caaaacttga tggtggtaga tggcgaacat cacctacaaa tgttgctaat    120

gatcaaatta aaacatttgt agcagaatca catggtttta tgacaggtac agaaggtact    180

atatattata gtataaatgg agaagcagaa attagtttat attttgataa tccttattca    240

ggttctaata aatatgatgg gcattccaat aaacctcaat atgaagttac tacccaagga    300

ggatcaggaa atcaatctca tgtaacgtat actattcaaa c                        341


<210> SEQ ID NO 120
<211> LENGTH: 113
<212> TYPE: PRT
<213> ORGANISM: Bacillus thuringiensis

<400> SEQUENCE: 120

Met Ser Gly Arg Glu Val His Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Phe Val Ala
         35                  40                  45

Glu Ser His Gly Phe Met Thr Gly Thr Glu Gly Thr Ile Tyr Tyr Ser
     50                  55                  60

Ile Asn Gly Glu Ala Glu Ile Ser Leu Tyr Phe Asp Asn Pro Tyr Ser
 65                  70                  75                  80
```

-continued

```
Gly Ser Asn Lys Tyr Asp Gly His Ser Asn Lys Pro Gln Tyr Glu Val
                85                  90                  95

Thr Thr Gln Gly Gly Ser Gly Asn Gln Ser His Val Thr Tyr Thr Ile
            100                 105                 110

Gln


<210> SEQ ID NO 121
<211> LENGTH: 341
<212> TYPE: DNA
<213> ORGANISM: Bacillus thuringiensis

<400> SEQUENCE: 121

atgtcaggtc gcgaagttga cattgatgta aataataaga caggtcatac attacaatta     60

gaagataaaa caaaacttga tggtggtaga tggcgaacat cacctacaaa tgttgctaat    120

gatcaaatta aaacatttgt agcagaatca catggtttta tgacaggtac agaaggtact    180

atatattata gtataaatgg agaagcagaa attagtttat attttgataa tccttattca    240

ggttctaata aatatgatgg gcattccaat aaacctcaat atgaagttac tacccaagga    300

ggatcaggaa atcaatctca tgtcacatat acgattcaaa c                        341


<210> SEQ ID NO 122
<211> LENGTH: 113
<212> TYPE: PRT
<213> ORGANISM: Bacillus thuringiensis

<400> SEQUENCE: 122

Met Ser Gly Arg Glu Val Asp Ile Asp Val Asn Asn Lys Thr Gly His
  1               5                  10                  15

Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
        35                  40                  45

Glu Ser His Gly Phe Met Thr Gly Thr Glu Gly Thr Ile Tyr Tyr Ser
    50                  55                  60

Ile Asn Gly Glu Ala Glu Ile Ser Leu Tyr Phe Asp Asn Pro Tyr Ser
 65                  70                  75                  80

Gly Ser Asn Lys Tyr Asp Gly His Ser Asn Lys Pro Gln Tyr Glu Val
                85                  90                  95

Thr Thr Gln Gly Gly Ser Gly Asn Gln Ser His Val Thr Tyr Thr Ile
            100                 105                 110

Gln


<210> SEQ ID NO 123
<211> LENGTH: 341
<212> TYPE: DNA
<213> ORGANISM: Bacillus thuringiensis

<400> SEQUENCE: 123

atgtcagcac gtgaagtaga tattgatgta aataataaga caggtcatac attacaatta     60

gaagataaaa caaaacttga tggtggtaga tggcgaacat cacctacaaa tgttgctaat    120

gatcaaatta aaacatttgt agcagaatca catggtttta tgacaggtac agaaggtact    180

atatattata gtataaatgg agaagcagaa attagtttat attttgataa tccttattca    240

ggttctaata aatatgatgg gcattccaat aaacctcaat atgaagttac tacccaagga    300

ggatcaggaa atcaatctca tgtaacgtat acgattcaaa c                        341
```

<210> SEQ ID NO 124
<211> LENGTH: 113
<212> TYPE: PRT
<213> ORGANISM: Bacillus thuringiensis

<400> SEQUENCE: 124

```
Met Ser Ala Arg Glu Val Asp Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Phe Val Ala
         35                  40                  45

Glu Ser His Gly Phe Met Thr Gly Thr Glu Gly Thr Ile Tyr Tyr Ser
     50                  55                  60

Ile Asn Gly Glu Ala Glu Ile Ser Leu Tyr Phe Asp Asn Pro Tyr Ser
 65                  70                  75                  80

Gly Ser Asn Lys Tyr Asp Gly His Ser Asn Lys Pro Gln Tyr Glu Val
                 85                  90                  95

Thr Thr Gln Gly Gly Ser Gly Asn Gln Ser His Val Thr Tyr Thr Ile
            100                 105                 110

Gln
```

<210> SEQ ID NO 125
<211> LENGTH: 1103
<212> TYPE: DNA
<213> ORGANISM: Bacillus thuringiensis

<400> SEQUENCE: 125

```
atgttagata ctaataaagt ttatgaaata agtaatcatg ctaatggact atatgcagca     60

acttatttaa gtttagatga ttcaggtgtt agtttaatga ataaaaatga tgatgatatt    120

gatgattata acttaaaatg gtttttattt cctattgatg atgatcaata tattattaca    180

agctatgcag caaataattg taaagtttgg aatgttaata atgataaaat aaatgtttcg    240

acttattctt caacaaattc aatacaaaaa tggcaaataa aagctaatgg ttcttcatat    300

gtaatacaaa gtgataatgg aaaagtctta acagcaggaa ccggtcaagc tcttggattg    360

atacgtttaa ctgatgaatc ctcaaataat cccaatcaac aatggaattt aacttctgta    420

caaacaattc aacttccaca aaaacctata atagatacaa aattaaaaga ttatcccaaa    480

tattcaccaa ctggaaatat agataatgga acatctcctc aattaatggg atggacatta    540

gtaccttgta ttatggtaaa tgatccaaat atagataaaa atactcaaat taaaactact    600

ccatattata ttttaaaaaa atatcaatat tggcaacgag cagtaggaag taatgtagct    660

ttacgtccac atgaagaaaa atcatatact tatgaatggg gaacagaaat agatcaaaaa    720

acaacaatca taaatacatt aggatttcaa atcaatatag attcaggaat gaaatttgat    780

ataccagaag taggtggagg tacagatgaa ataaaaacac aactaaatga agaattaaaa    840

atagaatata gtcgtgaaac taaaataatg gaaaaatatc aagaacaatc tgaaatagat    900

aatccaactg atcaaccaat gaattctata ggatttctta ctattacttc tttagaatta    960

tatagatata atggctcaga aattcgtata atgcaaattc aaacctcaga taatgatact   1020

tataatgtta cttcttatcc agatcatcaa caagctttat tacttcttac aaatcattca   1080

tatgaagaac ttgaagaaat tag                                            1103
```

<210> SEQ ID NO 126

<211> LENGTH: 367
<212> TYPE: PRT
<213> ORGANISM: Bacillus thuringiensis

<400> SEQUENCE: 126

```
Met Leu Asp Thr Asn Lys Val Tyr Glu Ile Ser Asn His Ala Asn Gly
  1               5                  10                  15

Leu Tyr Ala Ala Thr Tyr Leu Ser Leu Asp Asp Ser Gly Val Ser Leu
             20                  25                  30

Met Asn Lys Asn Asp Asp Asp Ile Asp Asp Tyr Asn Leu Lys Trp Phe
         35                  40                  45

Leu Phe Pro Ile Asp Asp Asp Gln Tyr Ile Ile Thr Ser Tyr Ala Ala
     50                  55                  60

Asn Asn Cys Lys Val Trp Asn Val Asn Asn Asp Lys Ile Asn Val Ser
 65                  70                  75                  80

Thr Tyr Ser Ser Thr Asn Ser Ile Gln Lys Trp Gln Ile Lys Ala Asn
                 85                  90                  95

Gly Ser Ser Tyr Val Ile Gln Ser Asp Asn Gly Lys Val Leu Thr Ala
            100                 105                 110

Gly Thr Gly Gln Ala Leu Gly Leu Ile Arg Leu Thr Asp Glu Ser Ser
        115                 120                 125

Asn Asn Pro Asn Gln Gln Trp Asn Leu Thr Ser Val Gln Thr Ile Gln
    130                 135                 140

Leu Pro Gln Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Arg Ala Val Gly Ser Asn Val Ala Leu Arg Pro His
    210                 215                 220

Glu Glu Lys Ser Tyr Thr Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser Arg Glu Thr Lys
        275                 280                 285

Ile Met Glu Lys Tyr Gln Glu Gln Ser Glu Ile Asp Asn Pro Thr Asp
    290                 295                 300

Gln Pro Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                325                 330                 335

Asp Asn Asp Thr Tyr Asn Val Thr Ser Tyr Pro Asp His Gln Gln Ala
            340                 345                 350

Leu Leu Leu Leu Thr Asn His Ser Tyr Glu Glu Leu Glu Glu Ile
        355                 360                 365
```

<210> SEQ ID NO 127
<211> LENGTH: 369
<212> TYPE: DNA

<213> ORGANISM: Artificial Sequence
<220> FEATURE:
<223> OTHER INFORMATION: Polynucleotide sequence for gene designated 149B1-15-PO, optimized for expression in Zea mays

<400> SEQUENCE: 127

```
atgtccgccc gcgaggtgca catcgacgtg aacaacaaga ccggccacac cctccagctg     60

gaggacaaga ccaagctcga cggcggcagg tggcgcacct ccccgaccaa cgtggccaac    120

gaccagatca agaccttcgt ggccgaatcc aacggcttca tgaccggcac cgagggcacc    180

atctactact ccatcaacgg cgaggccgag atcagcctct acttcgacaa cccgttcgcc    240

ggctccaaca aatacgacgg ccactccaac aagtcccagt acgagatcat cacccagggc    300

ggctccggca accagtccca cgtgacctac accatccaga ccacctcctc ccgctacggc    360

cacaagtcc                                                             369
```

<210> SEQ ID NO 128
<211> LENGTH: 1149
<212> TYPE: DNA
<213> ORGANISM: Artificial Sequence
<220> FEATURE:
<223> OTHER INFORMATION: Polynucleotide sequence for gene designated 149B1-45-PO, optimized for expression in Zea mays

<400> SEQUENCE: 128

```
atgctcgaca ccaacaaggt gtacgagatc agcaaccacg ccaacggcct ctacgccgcc     60

acctacctct ccctcgacga ctccggcgtg tccctcatga acaagaacga cgacgacatc    120

gacgactaca acctcaagtg gttcctcttc ccgatcgacg acgaccagta catcatcacc    180

tcctacgccg ccaacaactg caaggtgtgg aacgtgaaca acgacaagat caacgtgtcc    240

acctactcct ccaccaactc catccagaag tggcagatca aggccaacgg ctcctcctac    300

gtgatccagt ccgacaacgg caaggtgctc accgccggca ccggccaggc cctcggcctc    360

atccgcctca ccgacgagtc ctccaacaac ccgaaccagc aatggaacct gacgtccgtg    420

cagaccatcc agctcccgca gaagccgatc atcgacacca agctcaagga ctacccgaag    480

tactccccga ccggcaacat cgacaacggc acctccccgc agctcatggg ctggaccctc    540

gtgccgtgca tcatggtgaa cgacccgaac atcgacaaga acacccagat caagaccacc    600

ccgtactaca tcctcaagaa gtaccagtac tggcagaggg ccgtgggctc caacgtcgcg    660

ctccgcccgc acgagaagaa gtcctacacc tacgagtggg gcaccgagat cgaccagaag    720

accaccatca tcaacaccct cggcttccag atcaacatcg acagcggcat gaagttcgac    780

atcccggagg tgggcggcgg taccgacgag atcaagaccc agctcaacga ggagctcaag    840

atcgagtact cccacgagac gaagatcatg gagaagtacc aggagcagtc cgagatcgac    900

aacccgaccg accagtccat gaactccatc ggcttcctca ccatcacctc cctggagctc    960

taccgctaca acggctccga gatccgcatc atgcagatcc agacctccga caacgacacc   1020

tacaacgtga cctcctaccc gaaccaccag caggccctgc tgctgctgac caaccactcc   1080

tacgaggagg tggaggagat caccaacatc ccgaagtcca ccctcaagaa gctcaagaag   1140

tactacttc                                                            1149
```

<210> SEQ ID NO 129
<211> LENGTH: 357
<212> TYPE: DNA
<213> ORGANISM: Artificial Sequence
<220> FEATURE:
<223> OTHER INFORMATION: Polynucleotide sequence for gene designated -continued

```
      80JJ1-15-PO7, optimized for expression in maize

<400> SEQUENCE: 129

atgtccgccc gcgaggtgca catcgagatc aacaacaaga cccgccacac cctccagctc     60

gaggacaaga ccaagctctc cggcggcagg tggcgcacct ccccgaccaa cgtggcccgc    120

gacaccatca agacgttcgt ggcggagtcc cacggcttca tgaccggcgt cgagggcatc    180

atctacttct ccgtgaacgg cgacgccgag atctccctcc acttcgacaa cccgtacatc    240

ggctccaaca agtccgacgg ctcctccgac aagcccgagt acgaggtgat cacccagtcc    300

ggctccggcg acaagtccca cgtgacctac accatccaga ccgtgtccct ccgcctc       357


<210> SEQ ID NO 130
<211> LENGTH: 119
<212> TYPE: PRT
<213> ORGANISM: Artificial Sequence
<220> FEATURE:
<223> OTHER INFORMATION: Amino acid sequence for toxin encoded by gene
      designated 80JJ1-15-PO7

<400> SEQUENCE: 130

Met Ser Ala Arg Glu Val His Ile Glu Ile Asn Asn Lys Thr Arg His
  1               5                  10                  15

Thr Leu Gln Leu Glu Asp Lys Thr Lys Leu Ser Gly Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Val Glu Gly Ile Ile Tyr Phe Ser
     50                  55                  60

Val Asn Gly Asp Ala Glu Ile Ser Leu His Phe Asp Asn Pro Tyr Ile
 65                  70                  75                  80

Gly Ser Asn Lys Ser Asp Gly Ser Ser Asp Lys Pro Glu Tyr Glu Val
                 85                  90                  95

Ile Thr Gln Ser Gly Ser Gly Asp Lys Ser His Val Thr Tyr Thr Ile
            100                 105                 110

Gln Thr Val Ser Leu Arg Leu
        115
```